United States Patent
Bathe et al.

(10) Patent No.: US 8,293,514 B2
(45) Date of Patent: Oct. 23, 2012

(54) ALLELES OF THE REL GENE FROM CORYNEFORM BACTERIA

(75) Inventors: Brigitte Bathe, Salzkotten (DE); Caroline Kreutzer, Oerlinghausen (DE); Georg Thierbach, Bielefeld (DE)

(73) Assignee: Evonik Degussa GmbH, Duesseldorf (DE)

( * ) Notice: Subject to any disclaimer, the term of this patent is extended or adjusted under 35 U.S.C. 154(b) by 355 days.

(21) Appl. No.: 12/781,230

(22) Filed: May 17, 2010

(65) Prior Publication Data

US 2010/0311147 A1  Dec. 9, 2010

Related U.S. Application Data

(62) Division of application No. 11/873,073, filed on Oct. 16, 2007, now Pat. No. 7,754,446.

(30) Foreign Application Priority Data

Oct. 17, 2006  (DE) .......................... 10 2006 048 882

(51) Int. Cl.
   *C12N 9/12*  (2006.01)
(52) U.S. Cl. ....................................... 435/194
(58) Field of Classification Search .................. None
   See application file for complete search history.

(56) References Cited

U.S. PATENT DOCUMENTS

| | | | |
|---|---|---|---|
| 6,017,555 | A  | 1/2000 | Stevens et al. |
| 6,200,785 | B1 | 3/2001 | Kreutzer et al. |
| 6,696,561 | B1 | 2/2004 | Pompejus et al. |

FOREIGN PATENT DOCUMENTS

| | | |
|---|---|---|
| EP | 1 486 570 | 12/2004 |
| WO | WO 02/07183 | 1/2002 |
| WO | WO 2004/054381 | 7/2004 |

OTHER PUBLICATIONS

GenBank Acc# AAC35494 Mar. 15, 2001; from Wehmeier et al, Microbiology 144 (Pt 7), 1853-1862 (1998).*
Andreas et al, Journal of Bacteriology, 2005, 187(13) pp. 4671-4682 abstract only—DATABASE UniProt [Online], Aug. 2, 2005, "GTP pyrophosphokinase (EC <A HREF="http://srs.ebi.ac.uk/srsbin/cgi-bin/wgetz?[enzyme-ECNumber:2.7.6.5]+e">2.7.6.5</A>." XPOO2476693.
Wendrich et al, Molecular Microbiology, 1997, 26(1), pp. 65-79.
Wehmeier, Microbiology, 1998, 144, (pt. 7) pp. 1853-1862.
Colon et al, Appl. Environ Microbiol. vol. 61(1), (1995) pp. 74-78.
Kalinowski et al, J. Biotechnol. vol. 104(1-3), (2003) pp. 5-25 Review.
Gayle et al, J. Biol. Chem. vol. 268(29), (1993), pp. 22105-22111.
Whisstock et al, Q Rev. Biophys. vol. 36(3), (2003), pp. 307-340 Review.

* cited by examiner

*Primary Examiner* — Sheridan Swope
(74) *Attorney, Agent, or Firm* — Oblon, Spivak, McClelland, Maier & Neustadt, L.L.P.

(57) ABSTRACT

An isolated mutant of a coryneform bacterium comprising a gene coding for a polypeptide having GTP-pyrophosphate kinase activity, wherein said polypeptide comprises an amino acid sequence in which one of the proteinogenic amino acids other than L-proline is present in position 38 or a corresponding or comparable position. In addition, an isolated polynucleotide encoding a polypeptide having GTP-pyrophosphate kinase enzyme activity, a vector comprising the isolated polynucleotide, a recombinant microorganism comprising the vector, and a process for preparing the recombinant coryneform bacterium is described. A method for over-expressing a GTP-pyrophosphate kinase, a method of preparing an L-amino acid, an L-lysine comprising and L-tryptophan comprising feed is also described.

16 Claims, 1 Drawing Sheet

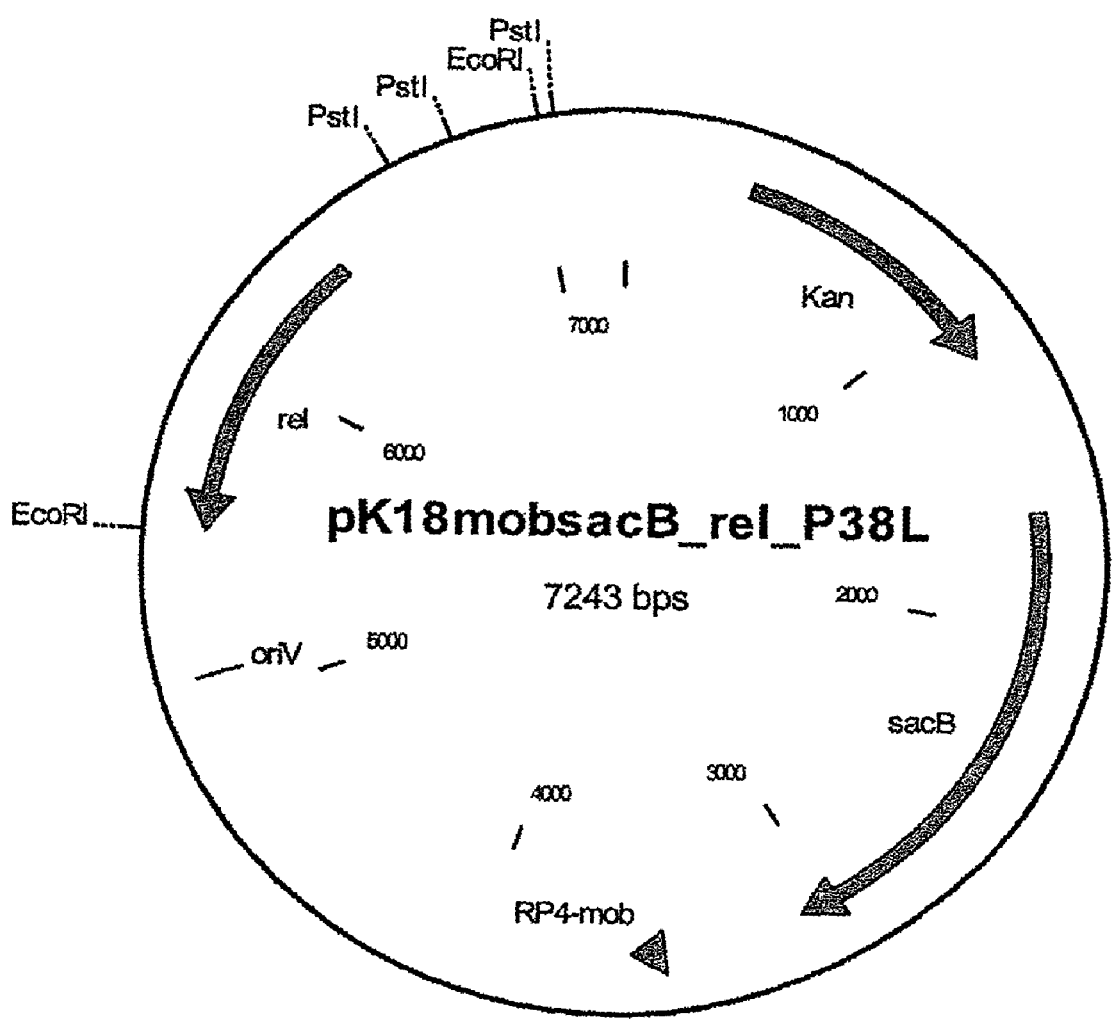

SEQUENCE LISTING

<160> NUMBER OF SEQ ID NOS: 27

<210> SEQ ID NO 1
<211> LENGTH: 2283
<212> TYPE: DNA
<213> ORGANISM: Corynebacterium glutamicum
<220> FEATURE:
<221> NAME/KEY: CDS
<222> LOCATION: (1)..(2280)
<220> FEATURE:
<221> NAME/KEY: misc_feature
<222> LOCATION: (785)..(785)
<223> OTHER INFORMATION: Guanine

<400> SEQUENCE: 1

| | | | | | | | | | | | | | | | | |
|---|---|---|---|---|---|---|---|---|---|---|---|---|---|---|---|---|
| atg | agt | ctg | gag | cgc | aac | aca | caa | aaa | tct | tcc | atg | ggt | gtg | cga | agc | 48 |
| Met | Ser | Leu | Glu | Arg | Asn | Thr | Gln | Lys | Ser | Ser | Met | Gly | Val | Arg | Ser | |
| 1 | | | | 5 | | | | | 10 | | | | | 15 | | |
| atg | tca | gcc | agg | ctt | gcc | cgc | agc | ctc | aca | gga | aac | cgc | gtt | cgc | acc | 96 |
| Met | Ser | Ala | Arg | Leu | Ala | Arg | Ser | Leu | Thr | Gly | Asn | Arg | Val | Arg | Thr | |
| | | | 20 | | | | | 25 | | | | | 30 | | | |
| aac | cct | gtg | ctg | gat | ccg | ctg | ctg | agc | atc | cac | cgg | caa | ttt | cac | cca | 144 |
| Asn | Pro | Val | Leu | Asp | Pro | Leu | Leu | Ser | Ile | His | Arg | Gln | Phe | His | Pro | |
| | | | | 35 | | | | | 40 | | | | | 45 | | |
| cgc | gcc | gac | gta | caa | gtg | ttg | gaa | cgt | gca | tat | gac | acc | gcg | gaa | cgt | 192 |
| Arg | Ala | Asp | Val | Gln | Val | Leu | Glu | Arg | Ala | Tyr | Asp | Thr | Ala | Glu | Arg | |
| | 50 | | | | | 55 | | | | | 60 | | | | | |
| ctt | cat | gat | ggt | gtg | att | cga | aaa | tcg | ggc | gat | ccg | tat | att | acc | cac | 240 |
| Leu | His | Asp | Gly | Val | Ile | Arg | Lys | Ser | Gly | Asp | Pro | Tyr | Ile | Thr | His | |
| 65 | | | | | 70 | | | | | 75 | | | | | 80 | |
| ccg | ttg | gct | gtc | gcc | acc | atc | gcc | gcg | gaa | atc | ggc | atg | gac | acc | acc | 288 |
| Pro | Leu | Ala | Val | Ala | Thr | Ile | Ala | Ala | Glu | Ile | Gly | Met | Asp | Thr | Thr | |
| | | | | 85 | | | | | 90 | | | | | 95 | | |
| acg | ctc | gtc | gca | gcc | ttg | ttg | cat | gac | acg | gtg | gaa | gac | acc | gac | tac | 336 |
| Thr | Leu | Val | Ala | Ala | Leu | Leu | His | Asp | Thr | Val | Glu | Asp | Thr | Asp | Tyr | |
| | | | 100 | | | | | 105 | | | | | 110 | | | |
| tct | ttg | gac | gat | ctc | acc | cga | gat | ttc | gga | gaa | gaa | gtt | gcc | agg | ctt | 384 |
| Ser | Leu | Asp | Asp | Leu | Thr | Arg | Asp | Phe | Gly | Glu | Glu | Val | Ala | Arg | Leu | |
| | | | | 115 | | | | | 120 | | | | | 125 | | |
| gtc | gac | ggt | gtc | acc | aag | ctc | gac | aaa | gtc | gca | cta | ggt | gct | gcc | gcg | 432 |
| Val | Asp | Gly | Val | Thr | Lys | Leu | Asp | Lys | Val | Ala | Leu | Gly | Ala | Ala | Ala | |
| | 130 | | | | | 135 | | | | | 140 | | | | | |
| gag | gcc | gaa | acg | att | cgc | aaa | atg | atc | gtc | gcc | atg | agc | cag | gac | ccc | 480 |
| Glu | Ala | Glu | Thr | Ile | Arg | Lys | Met | Ile | Val | Ala | Met | Ser | Gln | Asp | Pro | |
| 145 | | | | | 150 | | | | | 155 | | | | | 160 | |
| cgc | gtg | ctg | gtg | att | aaa | gtg | gcc | gac | cgt | ttg | cac | aat | atg | cgc | acc | 528 |
| Arg | Val | Leu | Val | Ile | Lys | Val | Ala | Asp | Arg | Leu | His | Asn | Met | Arg | Thr | |
| | | | | 165 | | | | | 170 | | | | | 175 | | |
| atg | cgg | ttc | ctg | ccg | ccg | gaa | aag | caa | gct | aaa | aaa | gca | cgc | caa | acc | 576 |
| Met | Arg | Phe | Leu | Pro | Pro | Glu | Lys | Gln | Ala | Lys | Lys | Ala | Arg | Gln | Thr | |
| | | | 180 | | | | | 185 | | | | | 190 | | | |
| ctt | gaa | gtg | att | gct | cct | ttg | gca | cac | cgc | ctg | ggc | atg | gcc | agc | gtg | 624 |
| Leu | Glu | Val | Ile | Ala | Pro | Leu | Ala | His | Arg | Leu | Gly | Met | Ala | Ser | Val | |
| | | | | 195 | | | | | 200 | | | | | 205 | | |
| aaa | tgg | gaa | ttg | gaa | gat | cta | tcc | ttt | gcc | att | ttg | tac | ccc | aag | aag | 672 |
| Lys | Trp | Glu | Leu | Glu | Asp | Leu | Ser | Phe | Ala | Ile | Leu | Tyr | Pro | Lys | Lys | |
| | 210 | | | | | 215 | | | | | 220 | | | | | |
| tac | gaa | gag | atc | gtg | cgt | ctt | gtt | gcc | gac | cgc | gcg | ccc | tct | aga | gac | 720 |
| Tyr | Glu | Glu | Ile | Val | Arg | Leu | Val | Ala | Asp | Arg | Ala | Pro | Ser | Arg | Asp | |
| 225 | | | | | 230 | | | | | 235 | | | | | 240 | |
| cgg | tac | ctc | aaa | gaa | att | att | gat | caa | gtc | acc | ggt | ggc | ttg | cgc | gaa | 768 |

| | | | | | | | | | | | | | | |
|---|---|---|---|---|---|---|---|---|---|---|---|---|---|---|
| Arg | Tyr | Leu | Lys | Glu | Ile | Ile | Asp | Gln | Val | Thr | Gly | Gly | Leu | Arg | Glu |
| | | | 245 | | | | | 250 | | | | 255 | | |

```
aac aac atc gcg gca gga gtg ctt ggt cga cca aag cac tac tgg tct    816
Asn Asn Ile Ala Ala Gly Val Leu Gly Arg Pro Lys His Tyr Trp Ser
            260                 265                 270 atc tat caa aag atg atc gtt cgc ggt cgt gat ttt gac gat att ttt    864
Ile Tyr Gln Lys Met Ile Val Arg Gly Arg Asp Phe Asp Asp Ile Phe
        275                 280                 285 gat ctt gtt ggc atc cgc atc ctg gta gac aac gtg aac aac tgt tac    912
Asp Leu Val Gly Ile Arg Ile Leu Val Asp Asn Val Asn Asn Cys Tyr
    290                 295                 300 gcc gcc atc ggt gtc gtg cac tcc ctg ttc aat gct ctg cct ggc cga    960
Ala Ala Ile Gly Val Val His Ser Leu Phe Asn Ala Leu Pro Gly Arg
305                 310                 315                 320 ttc aaa gac tat att tca gcc ccg cgc ttc ggt gtc tac caa tcc ctg   1008
Phe Lys Asp Tyr Ile Ser Ala Pro Arg Phe Gly Val Tyr Gln Ser Leu
                325                 330                 335 cac acc acc gtg atg gga cct ggc ggt aag cct ctg gaa gtt cag gca   1056
His Thr Thr Val Met Gly Pro Gly Gly Lys Pro Leu Glu Val Gln Ala
            340                 345                 350 cgt acc cac gac atg cac tac aac gcc gaa ttc ggc att gca gcg cac   1104
Arg Thr His Asp Met His Tyr Asn Ala Glu Phe Gly Ile Ala Ala His
        355                 360                 365 tgg cga tac aaa gaa acc aaa ggc agc cac agt ggc gag caa gcc gaa   1152
Trp Arg Tyr Lys Glu Thr Lys Gly Ser His Ser Gly Glu Gln Ala Glu
    370                 375                 380 gtg gat caa atg gcg tgg atg cgc caa ctt ctg gac tgg caa aaa gaa   1200
Val Asp Gln Met Ala Trp Met Arg Gln Leu Leu Asp Trp Gln Lys Glu
385                 390                 395                 400 gca gcc gac ccc aac gag ttc ctg gac agc ctg cgc tac gat ctg act   1248
Ala Ala Asp Pro Asn Glu Phe Leu Asp Ser Leu Arg Tyr Asp Leu Thr
                405                 410                 415 tcc aag cag atc ttc gtg ttc aca ccc aaa ggt gat gtg gtc aac ctg   1296
Ser Lys Gln Ile Phe Val Phe Thr Pro Lys Gly Asp Val Val Asn Leu
            420                 425                 430 ccg gtg aac tcc acc ccg gtg gac ttc gcc tac gcg gtg cac acc gaa   1344
Pro Val Asn Ser Thr Pro Val Asp Phe Ala Tyr Ala Val His Thr Glu
        435                 440                 445 gtg ggg cac cgc tgc atc ggc gcc aaa atc aac ggc aaa ctg gtc gct   1392
Val Gly His Arg Cys Ile Gly Ala Lys Ile Asn Gly Lys Leu Val Ala
    450                 455                 460 ttg gaa acg aaa ctc aaa tcc ggc gat cgt gtt gaa gtc ttt acc tcc   1440
Leu Glu Thr Lys Leu Lys Ser Gly Asp Arg Val Glu Val Phe Thr Ser
465                 470                 475                 480 aag gac caa aac gct ggc cca agt agg gga tgg caa gaa ttt gtt gtc   1488
Lys Asp Gln Asn Ala Gly Pro Ser Arg Gly Trp Gln Glu Phe Val Val
                485                 490                 495 tca cct cgt gca aag gcc aag att cgc cag tgg ttt gcc aag gaa cga   1536
Ser Pro Arg Ala Lys Ala Lys Ile Arg Gln Trp Phe Ala Lys Glu Arg
            500                 505                 510 cgc gaa gaa tac cta gaa gcc gga cgc gat gcg ctg gca gca gtt att   1584
Arg Glu Glu Tyr Leu Glu Ala Gly Arg Asp Ala Leu Ala Ala Val Ile
        515                 520                 525 cag cgt ggc ggc ctg cca atg cac cgc ttg ttc acc gcg tcc tcc atg   1632
Gln Arg Gly Gly Leu Pro Met His Arg Leu Phe Thr Ala Ser Ser Met
    530                 535                 540 aag acg gtg gca aca gag ctg cac tac cca gat gta gat gcg ctc tac   1680
Lys Thr Val Ala Thr Glu Leu His Tyr Pro Asp Val Asp Ala Leu Tyr
545                 550                 555                 560 aca gcc atc ggc tcc ggt tct gta tct gcg caa cac gta gtc aac cgt   1728
Thr Ala Ile Gly Ser Gly Ser Val Ser Ala Gln His Val Val Asn Arg
```

```
                                      -continued

Thr Ala Ile Gly Ser Gly Ser Val Ser Ala Gln His Val Val Asn Arg
                565                 570                 575 ctc atg gct atc ttt ggt gac gaa gaa gat gcc gaa gac gca ttg gtt      1776
Leu Met Ala Ile Phe Gly Asp Glu Glu Asp Ala Glu Asp Ala Leu Val
            580                 585                 590 gca cgc acc cca ttc agc gag ctg gtc aac tcc cgt gcc acc acg gaa      1824
Ala Arg Thr Pro Phe Ser Glu Leu Val Asn Ser Arg Ala Thr Thr Glu
        595                 600                 605 agc agc acc ggc atc ctg gtc gaa ggc agc cca gat gtc atg gct aag      1872
Ser Ser Thr Gly Ile Leu Val Glu Gly Ser Pro Asp Val Met Ala Lys
    610                 615                 620 ctc gct aaa tgc tgt atg cca gtg cca gga gat gaa atc ttt gga ttc      1920
Leu Ala Lys Cys Cys Met Pro Val Pro Gly Asp Glu Ile Phe Gly Phe
625                 630                 635                 640 gtc acc cgt ggt ggc ggt gtc tcc gta cac cga aca gac tgc acg aat      1968
Val Thr Arg Gly Gly Gly Val Ser Val His Arg Thr Asp Cys Thr Asn
                645                 650                 655 gtg gaa aag ctc aaa gaa gag cca gaa cgc att gtc tcc gtc tcc tgg      2016
Val Glu Lys Leu Lys Glu Glu Pro Glu Arg Ile Val Ser Val Ser Trp
            660                 665                 670 gct tcg gaa ggt caa ggt tca gta ttc tct gcc aca ctg cag ctt gaa      2064
Ala Ser Glu Gly Gln Gly Ser Val Phe Ser Ala Thr Leu Gln Leu Glu
        675                 680                 685 gca ctt gat cgc gca ggc ctg ctc ttt gag ctc acc cgc gta atc aac      2112
Ala Leu Asp Arg Ala Gly Leu Leu Phe Glu Leu Thr Arg Val Ile Asn
    690                 695                 700 gaa caa aag gtc tcc gtt acc gca atg aac tcc cat tgc tca gaa gac      2160
Glu Gln Lys Val Ser Val Thr Ala Met Asn Ser His Cys Ser Glu Asp
705                 710                 715                 720 cgc gta gcc acc gtg cgc ttc acc ttt gcg gtc tct gac acc aag cag      2208
Arg Val Ala Thr Val Arg Phe Thr Phe Ala Val Ser Asp Thr Lys Gln
                725                 730                 735 ttg gga tcc ctg atg aca cag ctg cgc aat gcc gaa gga gtg ttt gat      2256
Leu Gly Ser Leu Met Thr Gln Leu Arg Asn Ala Glu Gly Val Phe Asp
            740                 745                 750 gtc tac cga gtg acc tcg ggt ggc tag                                  2283
Val Tyr Arg Val Thr Ser Gly Gly
        755                 760

<210> SEQ ID NO 2
<211> LENGTH: 760
<212> TYPE: PRT
<213> ORGANISM: Corynebacterium glutamicum

<400> SEQUENCE: 2

Met Ser Leu Glu Arg Asn Thr Gln Lys Ser Ser Met Gly Val Arg Ser
1               5                   10                  15

Met Ser Ala Arg Leu Ala Arg Ser Leu Thr Gly Asn Arg Val Arg Thr
            20                  25                  30

Asn Pro Val Leu Asp Pro Leu Leu Ser Ile His Arg Gln Phe His Pro
        35                  40                  45

Arg Ala Asp Val Gln Val Leu Glu Arg Ala Tyr Asp Thr Ala Glu Arg
    50                  55                  60

Leu His Asp Gly Val Ile Arg Lys Ser Gly Asp Pro Tyr Ile Thr His
65                  70                  75                  80

Pro Leu Ala Val Ala Thr Ile Ala Ala Glu Ile Gly Met Asp Thr Thr
                85                  90                  95

Thr Leu Val Ala Ala Leu Leu His Asp Thr Val Glu Asp Thr Asp Tyr
            100                 105                 110
```

```
Ser Leu Asp Asp Leu Thr Arg Asp Phe Gly Glu Val Ala Arg Leu
        115                 120                 125

Val Asp Gly Val Thr Lys Leu Asp Lys Val Ala Leu Gly Ala Ala Ala
130                 135                 140

Glu Ala Glu Thr Ile Arg Lys Met Ile Val Ala Met Ser Gln Asp Pro
145                 150                 155                 160

Arg Val Leu Val Ile Lys Val Ala Asp Arg Leu His Asn Met Arg Thr
                165                 170                 175

Met Arg Phe Leu Pro Pro Glu Lys Gln Ala Lys Ala Arg Gln Thr
            180                 185                 190

Leu Glu Val Ile Ala Pro Leu Ala His Arg Leu Gly Met Ala Ser Val
            195                 200                 205

Lys Trp Glu Leu Glu Asp Leu Ser Phe Ala Ile Leu Tyr Pro Lys Lys
210                 215                 220

Tyr Glu Glu Ile Val Arg Leu Val Ala Asp Arg Ala Pro Ser Arg Asp
225                 230                 235                 240

Arg Tyr Leu Lys Glu Ile Ile Asp Gln Val Thr Gly Gly Leu Arg Glu
                245                 250                 255

Asn Asn Ile Ala Ala Gly Val Leu Gly Arg Pro Lys His Tyr Trp Ser
            260                 265                 270

Ile Tyr Gln Lys Met Ile Val Arg Gly Arg Asp Phe Asp Asp Ile Phe
    275                 280                 285

Asp Leu Val Gly Ile Arg Ile Leu Val Asp Asn Val Asn Asn Cys Tyr
    290                 295                 300

Ala Ala Ile Gly Val Val His Ser Leu Phe Asn Ala Leu Pro Gly Arg
305                 310                 315                 320

Phe Lys Asp Tyr Ile Ser Ala Pro Arg Phe Gly Val Tyr Gln Ser Leu
                325                 330                 335

His Thr Thr Val Met Gly Pro Gly Lys Pro Leu Glu Val Gln Ala
            340                 345                 350

Arg Thr His Asp Met His Tyr Asn Ala Glu Phe Gly Ile Ala Ala His
            355                 360                 365

Trp Arg Tyr Lys Glu Thr Lys Gly Ser His Ser Gly Gln Ala Glu
    370                 375                 380

Val Asp Gln Met Ala Trp Met Arg Gln Leu Leu Asp Trp Gln Lys Glu
385                 390                 395                 400

Ala Ala Asp Pro Asn Glu Phe Leu Asp Ser Leu Arg Tyr Asp Leu Thr
                405                 410                 415

Ser Lys Gln Ile Phe Val Phe Thr Pro Lys Gly Asp Val Val Asn Leu
            420                 425                 430

Pro Val Asn Ser Thr Pro Val Asp Phe Ala Tyr Ala Val His Thr Glu
            435                 440                 445

Val Gly His Arg Cys Ile Gly Ala Lys Ile Asn Gly Lys Leu Val Ala
450                 455                 460

Leu Glu Thr Lys Leu Lys Ser Gly Asp Arg Val Glu Val Phe Thr Ser
465                 470                 475                 480

Lys Asp Gln Asn Ala Gly Pro Ser Arg Gly Trp Gln Glu Phe Val Val
                485                 490                 495

Ser Pro Arg Ala Lys Ala Lys Ile Arg Gln Trp Phe Ala Lys Glu Arg
            500                 505                 510

Arg Glu Glu Tyr Leu Glu Ala Gly Arg Asp Ala Leu Ala Ala Val Ile
            515                 520                 525

Gln Arg Gly Gly Leu Pro Met His Arg Leu Phe Thr Ala Ser Ser Met
530                 535                 540
```

```
Lys Thr Val Ala Thr Glu Leu His Tyr Pro Asp Val Asp Ala Leu Tyr
545                 550                 555                 560

Thr Ala Ile Gly Ser Gly Ser Val Ser Ala Gln His Val Val Asn Arg
            565                 570                 575

Leu Met Ala Ile Phe Gly Asp Glu Glu Asp Ala Glu Asp Ala Leu Val
        580                 585                 590

Ala Arg Thr Pro Phe Ser Glu Leu Val Asn Ser Arg Ala Thr Thr Glu
    595                 600                 605

Ser Ser Thr Gly Ile Leu Val Glu Gly Ser Pro Asp Val Met Ala Lys
    610                 615                 620

Leu Ala Lys Cys Cys Met Pro Val Pro Gly Asp Glu Ile Phe Gly Phe
625                 630                 635                 640

Val Thr Arg Gly Gly Gly Val Ser Val His Arg Thr Asp Cys Thr Asn
            645                 650                 655

Val Glu Lys Leu Lys Glu Glu Pro Glu Arg Ile Val Ser Val Ser Trp
        660                 665                 670

Ala Ser Glu Gly Gln Gly Ser Val Phe Ser Ala Thr Leu Gln Leu Glu
    675                 680                 685

Ala Leu Asp Arg Ala Gly Leu Leu Phe Glu Leu Thr Arg Val Ile Asn
    690                 695                 700

Glu Gln Lys Val Ser Val Thr Ala Met Asn Ser His Cys Ser Glu Asp
705                 710                 715                 720

Arg Val Ala Thr Val Arg Phe Thr Phe Ala Val Ser Asp Thr Lys Gln
            725                 730                 735

Leu Gly Ser Leu Met Thr Gln Leu Arg Asn Ala Glu Gly Val Phe Asp
        740                 745                 750

Val Tyr Arg Val Thr Ser Gly Gly
    755                 760

<210> SEQ ID NO 3
<211> LENGTH: 3800
<212> TYPE: DNA
<213> ORGANISM: Corynebacterium glutamicum
<220> FEATURE:
<221> NAME/KEY: misc_feature
<222> LOCATION: (751)..(3033)
<223> OTHER INFORMATION: rel wild-type gene
<220> FEATURE:
<221> NAME/KEY: misc_feature
<222> LOCATION: (1535)..(1535)
<223> OTHER INFORMATION: Guanine

<400> SEQUENCE: 3
aggcgcaact gaagaacaat tgtgggctga agtcccatca attccactag cagcgcaacc      60
ccgagtgttt gtgatagatc gcacagtcgg taacgttgtt gttaatacag acctagccgg     120
tatcggatgg aacatgaccg ttggtccaga agtgaggaat aagtagtgag cgaacaagct     180
ctaagcacct tcgacagggc acgtgaggcc ctggacaaga aaacccgata tgtgcaggat     240
ttcccagaaa agggtgtgct ttttgaagac ctcaccccgg tgttgggcga tgcagaatca     300
tttgtggccg tggtggacgc catggctgaa gctgcagaaa aactgaatgc agaaatcatc     360
ggtggcttgg atgcgcgagg attcctcctc ggatctgctg tcgcttacaa actcggccta     420
ggtgtgctgc tatccgcaa gaagggaaag ctcccccac ctgtggtgac ccaggagtat      480
gaacttgaat acggcactgc agcactcgag ctgcccagtg aaggaatcga cattgctggt     540
aaaaacatcg ttttgatcga cgatgtgctg caaccggcg gcaccttggg cgctgcacgt     600
aaactaattg aatcgtgtga cggacatgtt tccggatatg ttcttgccat tgaggtccca     660
```

| | |
|---|---|
| ggcctcggcg gtagggataa tcttggtgat aggcccgtca ttgtggtcag agatcctcag | 720 |
| tagaaggatc gaaagaaagg cggcaggaaa atgagtctgg agcgcaacac acaaaaatct | 780 |
| tccatgggtg tgcgaagcat gtcagccagg cttgcccgca gcctcacagg aaaccgcgtt | 840 |
| cgcaccaacc ctgtgctgga tccgctgctg agcatccacc ggcaatttca cccacgcgcc | 900 |
| gacgtacaag tgttggaacg tgcatatgac accgcggaac gtcttcatga tggtgtgatt | 960 |
| cgaaaatcgg gcgatccgta tattacccac ccgttggctg tcgccaccat cgccgcggaa | 1020 |
| atcggcatgg acaccaccac gctcgtcgca gccttgttgc atgacacggt ggaagacacc | 1080 |
| gactactctt tggacgatct cacccgagat ttcggagaag aagttgccag gcttgtcgac | 1140 |
| ggtgtcacca agctcgacaa agtcgcacta ggtgctgccg cggaggccga acgattcgc | 1200 |
| aaaatgatcg tcgccatgag ccaggacccc cgcgtgctgg tgattaaagt ggccgaccgt | 1260 |
| ttgcacaata tgcgcaccat gcggttcctg ccgccggaaa agcaagctaa aaaagcacgc | 1320 |
| caaacccttg aagtgattgc tcctttggca caccgcctgg gcatggccag cgtgaaatgg | 1380 |
| gaattggaag atctatcctt tgccattttg taccccaaga agtacgaaga gatcgtgcgt | 1440 |
| cttgttgccg accgcgcgcc ctctagagac cggtacctca agaaattat tgatcaagtc | 1500 |
| accggtggct tgcgcgaaaa caacatcgcg gcaggagtgc ttggtcgacc aaagcactac | 1560 |
| tggtctatct atcaaaagat gatcgttcgc ggtcgtgatt ttgacgatat ttttgatctt | 1620 |
| gttggcatcc gcatcctggt agacaacgtg aacaactgtt acgccgccat cggtgtcgtg | 1680 |
| cactccctgt tcaatgctct gcctggccga ttcaaagact atatttcagc cccgcgcttc | 1740 |
| ggtgtctacc aatccctgca caccaccgtg atgggacctg gcggtaagcc tctggaagtt | 1800 |
| caggcacgta cccacgacat gcactacaac gccgaattcg gcattgcagc gcactggcga | 1860 |
| tacaaagaaa ccaaaggcag ccacagtggc gagcaagccg aagtggatca aatggcgtgg | 1920 |
| atgcgccaac ttctggactg gcaaaaagaa gcagccgacc caacgagtt cctggacagc | 1980 |
| ctgcgctacg atctgacttc caagcagatc ttcgtgttca cacccaaagg tgatgtggtc | 2040 |
| aacctgccgg tgaactccac cccggtggac ttcgcctacg cggtgcacac cgaagtgggg | 2100 |
| caccgctgca tcggcgccaa aatcaacggc aaactggtcg ctttggaaac gaaactcaaa | 2160 |
| tccggcgatc gtgttgaagt ctttacctcc aaggaccaaa acgctggccc aagtagggga | 2220 |
| tggcaagaat ttgttgtctc acctcgtgca aaggccaaga ttcgccagtg gtttgccaag | 2280 |
| gaacgacgcg aagaatacct agaagccgga cgcgatgcgc tggcagcagt tattcagcgt | 2340 |
| ggcggcctgc caatgcaccg cttgttcacc gcgtcctcca tgaagacggt ggcaacagag | 2400 |
| ctgcactacc cagatgtaga tgcgctctac acagccatcg gctccggttc tgtatctgcg | 2460 |
| caacacgtag tcaaccgtct catggctatc tttggtgacg aagaagatgc cgaagacgca | 2520 |
| ttggttgcac gcacccccatt cagcgagctg gtcaactccc gtgccaccac ggaaagcagc | 2580 |
| accggcatcc tggtcgaagg cagcccagat gtcatggcta agctcgctaa atgctgtatg | 2640 |
| ccagtgccag gagatgaaat ctttggattc gtcacccgtg gtggcggtgt ctccgtacac | 2700 |
| cgaacagact gcacgaatgt ggaaaagctc aagaagagc cagaacgcat tgtctccgtc | 2760 |
| tcctgggctt cggaaggtca aggttcagta ttctctgcca cactgcagct tgaagcactt | 2820 |
| gatcgcgcag gcctgctctt tgagctcacc cgcgtaatca cgaacaaaa ggtctccgtt | 2880 |
| accgcaatga actcccattg ctcagaagac cgcgtagcca ccgtgcgctt cacctttgcg | 2940 |
| gtctctgaca ccaagcagtt gggatcctg atgacacagc tgcgcaatgc cgaaggagtg | 3000 |
| tttgatgtct accgagtgac ctcgggtggc tagaggcctt tagattgtga aaaagccttg | 3060 |

```
ggcttcaacc accgtgtgtt gacacggttt tggggttgga tttaacgctg gaaattttac    3120
tgcaatgaac gctggaaagc agtagcgaag gtcaaaccag cgctgaggac gccaacgatg    3180
ccagtaataa cgacgacgta atccaaaatg gtgtcagagt caatgtcaga agatccgttg    3240
gtgctaccgt ttcttcttct acggtgtcag ccacgtacac aacctgtgct ggtgcgactt    3300
cttcagcctg tgcaggaacg gagatggagg ttgctgccat tgcagcagct gtgccgagtg    3360
cgacgagggg agtacgagaa aatagcttca ttgctaaacc ccttaggttt aaatattcga    3420
atacgaaagt tactttatgt gcactttcac cattgtgcaa ctatatgtgc aggtcaaagc    3480
tgatattttg ctaagaaaag tgcaaagcga ttcgagctga cgcgcagccc atatcgtcaa    3540
aaaatccttt gtgaatggtg attcacaaag gattagtcgc gtaaggcgga aattacttca    3600
ggaaggaatc cagcttggta ctgaaggtta aatggtggt tagtgcaccg atgactgctg    3660
tgatgatctt gatccagttt tcgatgttgt cagtgtcgga agaaccgctg gaaggctctt    3720
cgctggacgg gtcttcgttg aaatcaaagt taacgtaaac ttctgcttca acgcctgctt    3780
cgttcttggc aatgatcttt                                                3800

<210> SEQ ID NO 4
<211> LENGTH: 760
<212> TYPE: PRT
<213> ORGANISM: Corynebacterium glutamicum

<400> SEQUENCE: 4

Met Ser Leu Glu Arg Asn Thr Gln Lys Ser Met Gly Val Arg Ser
1               5                   10                  15

Met Ser Ala Arg Leu Ala Arg Ser Leu Thr Gly Asn Arg Val Arg Thr
            20                  25                  30

Asn Pro Val Leu Asp Pro Leu Leu Ser Ile His Arg Gln Phe His Pro
        35                  40                  45

Arg Ala Asp Val Gln Val Leu Glu Arg Ala Tyr Asp Thr Ala Glu Arg
    50                  55                  60

Leu His Asp Gly Val Ile Arg Lys Ser Gly Asp Pro Tyr Ile Thr His
65                  70                  75                  80

Pro Leu Ala Val Ala Thr Ile Ala Ala Glu Ile Gly Met Asp Thr Thr
                85                  90                  95

Thr Leu Val Ala Ala Leu Leu His Asp Thr Val Glu Asp Thr Asp Tyr
            100                 105                 110

Ser Leu Asp Asp Leu Thr Arg Asp Phe Gly Glu Glu Val Ala Arg Leu
        115                 120                 125

Val Asp Gly Val Thr Lys Leu Asp Lys Val Ala Leu Gly Ala Ala Ala
    130                 135                 140

Glu Ala Glu Thr Ile Arg Lys Met Ile Val Ala Met Ser Gln Asp Pro
145                 150                 155                 160

Arg Val Leu Val Ile Lys Val Ala Asp Arg Leu His Asn Met Arg Thr
                165                 170                 175

Met Arg Phe Leu Pro Pro Glu Lys Gln Ala Lys Ala Arg Gln Thr
            180                 185                 190

Leu Glu Val Ile Ala Pro Leu Ala His Arg Leu Gly Met Ala Ser Val
        195                 200                 205

Lys Trp Glu Leu Glu Asp Leu Ser Phe Ala Ile Leu Tyr Pro Lys Lys
    210                 215                 220

Tyr Glu Glu Ile Val Arg Leu Val Ala Asp Arg Ala Pro Ser Arg Asp
225                 230                 235                 240
```

-continued

```
Arg Tyr Leu Lys Glu Ile Ile Asp Gln Val Thr Gly Leu Arg Glu
            245                 250                 255
Asn Asn Ile Ala Ala Gly Val Leu Gly Arg Pro Lys His Tyr Trp Ser
        260                 265                 270
Ile Tyr Gln Lys Met Ile Val Arg Gly Arg Asp Phe Asp Ile Phe
    275                 280                 285
Asp Leu Val Gly Ile Arg Ile Leu Val Asp Asn Val Asn Asn Cys Tyr
290                 295                 300
Ala Ala Ile Gly Val Val His Ser Leu Phe Asn Ala Leu Pro Gly Arg
305                 310                 315                 320
Phe Lys Asp Tyr Ile Ser Ala Pro Arg Phe Gly Val Tyr Gln Ser Leu
                325                 330                 335
His Thr Thr Val Met Gly Pro Gly Lys Pro Leu Glu Val Gln Ala
            340                 345                 350
Arg Thr His Asp Met His Tyr Asn Ala Glu Phe Gly Ile Ala Ala His
        355                 360                 365
Trp Arg Tyr Lys Glu Thr Lys Gly Ser His Ser Gly Glu Gln Ala Glu
    370                 375                 380
Val Asp Gln Met Ala Trp Met Arg Gln Leu Leu Asp Trp Gln Lys Glu
385                 390                 395                 400
Ala Ala Asp Pro Asn Glu Phe Leu Asp Ser Leu Arg Tyr Asp Leu Thr
                405                 410                 415
Ser Lys Gln Ile Phe Val Phe Thr Pro Lys Gly Asp Val Val Asn Leu
            420                 425                 430
Pro Val Asn Ser Thr Pro Val Asp Phe Ala Tyr Ala Val His Thr Glu
        435                 440                 445
Val Gly His Arg Cys Ile Gly Ala Lys Ile Asn Gly Lys Leu Val Ala
    450                 455                 460
Leu Glu Thr Lys Leu Lys Ser Gly Asp Arg Val Glu Val Phe Thr Ser
465                 470                 475                 480
Lys Asp Gln Asn Ala Gly Pro Ser Arg Gly Trp Gln Glu Phe Val Val
                485                 490                 495
Ser Pro Arg Ala Lys Ala Lys Ile Arg Gln Trp Phe Ala Lys Glu Arg
            500                 505                 510
Arg Glu Glu Tyr Leu Glu Ala Gly Arg Asp Ala Leu Ala Ala Val Ile
        515                 520                 525
Gln Arg Gly Gly Leu Pro Met His Arg Leu Phe Thr Ala Ser Ser Met
    530                 535                 540
Lys Thr Val Ala Thr Glu Leu His Tyr Pro Asp Val Asp Ala Leu Tyr
545                 550                 555                 560
Thr Ala Ile Gly Ser Gly Ser Val Ser Ala Gln His Val Val Asn Arg
                565                 570                 575
Leu Met Ala Ile Phe Gly Asp Glu Glu Asp Ala Glu Asp Ala Leu Val
            580                 585                 590
Ala Arg Thr Pro Phe Ser Glu Leu Val Asn Ser Arg Ala Thr Thr Glu
        595                 600                 605
Ser Ser Thr Gly Ile Leu Val Glu Gly Ser Pro Asp Val Met Ala Lys
    610                 615                 620
Leu Ala Lys Cys Cys Met Pro Val Pro Gly Asp Glu Ile Phe Gly Phe
625                 630                 635                 640
Val Thr Arg Gly Gly Gly Val Ser Val His Arg Thr Asp Cys Thr Asn
                645                 650                 655
Val Glu Lys Leu Lys Glu Glu Pro Glu Arg Ile Val Ser Val Ser Trp
            660                 665                 670
```

-continued

```
Ala Ser Glu Gly Gln Gly Ser Val Phe Ser Ala Thr Leu Gln Leu Glu
        675                 680                 685
Ala Leu Asp Arg Ala Gly Leu Leu Phe Glu Leu Thr Arg Val Ile Asn
        690                 695                 700
Glu Gln Lys Val Ser Val Thr Ala Met Asn Ser His Cys Ser Glu Asp
705                 710                 715                 720
Arg Val Ala Thr Val Arg Phe Thr Phe Ala Val Ser Asp Thr Lys Gln
                725                 730                 735
Leu Gly Ser Leu Met Thr Gln Leu Arg Asn Ala Glu Gly Val Phe Asp
                740                 745                 750
Val Tyr Arg Val Thr Ser Gly Gly
                755                 760

<210> SEQ ID NO 5
<211> LENGTH: 2283
<212> TYPE: DNA
<213> ORGANISM: Corynebacterium glutamicum
<220> FEATURE:
<221> NAME/KEY: CDS
<222> LOCATION: (1)..(2280)
<223> OTHER INFORMATION: rel allele
<220> FEATURE:
<221> NAME/KEY: misc_feature
<222> LOCATION: (113)..(113)
<223> OTHER INFORMATION: C - > T transition
<220> FEATURE:
<221> NAME/KEY: misc_feature
<222> LOCATION: (785)..(785)
<223> OTHER INFORMATION: Guanine

<400> SEQUENCE: 5 atg agt ctg gag cgc aac aca caa aaa tct tcc atg ggt gtg cga agc    48
Met Ser Leu Glu Arg Asn Thr Gln Lys Ser Ser Met Gly Val Arg Ser
1               5                   10                  15 atg tca gcc agg ctt gcc cgc agc ctc aca gga aac cgc gtt cgc acc    96
Met Ser Ala Arg Leu Ala Arg Ser Leu Thr Gly Asn Arg Val Arg Thr
                20                  25                  30 aac cct gtg ctg gat ctg ctg ctg agc atc cac cgg caa ttt cac cca   144
Asn Pro Val Leu Asp Leu Leu Leu Ser Ile His Arg Gln Phe His Pro
            35                  40                  45 cgc gcc gac gta caa gtg ttg gaa cgt gca tat gac acc gcg gaa cgt   192
Arg Ala Asp Val Gln Val Leu Glu Arg Ala Tyr Asp Thr Ala Glu Arg
        50                  55                  60 ctt cat gat ggt gtg att cga aaa tcg ggc gat ccg tat att acc cac   240
Leu His Asp Gly Val Ile Arg Lys Ser Gly Asp Pro Tyr Ile Thr His
65                  70                  75                  80 ccg ttg gct gtc gcc acc atc gcc gcg gaa atc ggc atg gac acc acc   288
Pro Leu Ala Val Ala Thr Ile Ala Ala Glu Ile Gly Met Asp Thr Thr
                85                  90                  95 acg ctc gtc gca gcc ttg ttg cat gac acg gtg gaa gac acc gac tac   336
Thr Leu Val Ala Ala Leu Leu His Asp Thr Val Glu Asp Thr Asp Tyr
                100                 105                 110 tct ttg gac gat ctc acc cga gat ttc gga gaa gaa gtt gcc agg ctt   384
Ser Leu Asp Asp Leu Thr Arg Asp Phe Gly Glu Glu Val Ala Arg Leu
            115                 120                 125 gtc gac ggt gtc acc aag ctc gac aaa gtc gca cta ggt gct gcc gcg   432
Val Asp Gly Val Thr Lys Leu Asp Lys Val Ala Leu Gly Ala Ala Ala
        130                 135                 140 gag gcc gaa acg att cgc aaa atg atc gtc gcc atg agc cag gac ccc   480
Glu Ala Glu Thr Ile Arg Lys Met Ile Val Ala Met Ser Gln Asp Pro
145                 150                 155                 160 cgc gtg ctg gtg att aaa gtg gcc gac cgt ttg cac aat atg cgc acc   528
```

-continued

```
                Arg Val Leu Val Ile Lys Val Ala Asp Arg Leu His Asn Met Arg Thr
                                165                 170                 175 atg cgg ttc ctg ccg ccg gaa aag caa gct aaa aaa gca cgc caa acc            576
Met Arg Phe Leu Pro Pro Glu Lys Gln Ala Lys Lys Ala Arg Gln Thr
            180                 185                 190 ctt gaa gtg att gct cct ttg gca cac cgc ctg ggc atg gcc agc gtg            624
Leu Glu Val Ile Ala Pro Leu Ala His Arg Leu Gly Met Ala Ser Val
        195                 200                 205 aaa tgg gaa ttg gaa gat cta tcc ttt gcc att ttg tac ccc aag aag            672
Lys Trp Glu Leu Glu Asp Leu Ser Phe Ala Ile Leu Tyr Pro Lys Lys
    210                 215                 220 tac gaa gag atc gtg cgt ctt gtt gcc gac cgc gcg ccc tct aga gac            720
Tyr Glu Glu Ile Val Arg Leu Val Ala Asp Arg Ala Pro Ser Arg Asp
225                 230                 235                 240 cgg tac ctc aaa gaa att att gat caa gtc acc ggt ggc ttg cgc gaa            768
Arg Tyr Leu Lys Glu Ile Ile Asp Gln Val Thr Gly Gly Leu Arg Glu
                245                 250                 255 aac aac atc gcg gca gga gtg ctt ggt cga cca aag cac tac tgg tct            816
Asn Asn Ile Ala Ala Gly Val Leu Gly Arg Pro Lys His Tyr Trp Ser
            260                 265                 270 atc tat caa aag atg atc gtt cgc ggt cgt gat ttt gac gat att ttt            864
Ile Tyr Gln Lys Met Ile Val Arg Gly Arg Asp Phe Asp Asp Ile Phe
        275                 280                 285 gat ctt gtt ggc atc cgc atc ctg gta gac aac gtg aac aac tgt tac            912
Asp Leu Val Gly Ile Arg Ile Leu Val Asp Asn Val Asn Asn Cys Tyr
    290                 295                 300 gcc gcc atc ggt gtc gtg cac tcc ctg ttc aat gct ctg cct ggc cga            960
Ala Ala Ile Gly Val Val His Ser Leu Phe Asn Ala Leu Pro Gly Arg
305                 310                 315                 320 ttc aaa gac tat att tca gcc ccg cgc ttc ggt gtc tac caa tcc ctg           1008
Phe Lys Asp Tyr Ile Ser Ala Pro Arg Phe Gly Val Tyr Gln Ser Leu
                325                 330                 335 cac acc acc gtg atg gga cct ggc ggt aag cct ctg gaa gtt cag gca           1056
His Thr Thr Val Met Gly Pro Gly Gly Lys Pro Leu Glu Val Gln Ala
            340                 345                 350 cgt acc cac gac atg cac tac aac gcc gaa ttc ggc att gca gcg cac           1104
Arg Thr His Asp Met His Tyr Asn Ala Glu Phe Gly Ile Ala Ala His
        355                 360                 365 tgg cga tac aaa gaa acc aaa ggc agc cac agt ggc gag caa gcc gaa           1152
Trp Arg Tyr Lys Glu Thr Lys Gly Ser His Ser Gly Glu Gln Ala Glu
    370                 375                 380 gtg gat caa atg gcg tgg atg cgc caa ctt ctg gac tgg caa aaa gaa           1200
Val Asp Gln Met Ala Trp Met Arg Gln Leu Leu Asp Trp Gln Lys Glu
385                 390                 395                 400 gca gcc gac ccc aac gag ttc ctg gac agc ctg cgc tac gat ctg act           1248
Ala Ala Asp Pro Asn Glu Phe Leu Asp Ser Leu Arg Tyr Asp Leu Thr
                405                 410                 415 tcc aag cag atc ttc gtg ttc aca ccc aaa ggt gat gtg gtc aac ctg           1296
Ser Lys Gln Ile Phe Val Phe Thr Pro Lys Gly Asp Val Val Asn Leu
            420                 425                 430 ccg gtg aac tcc acc ccg gtg gac ttc gcc tac gcg gtg cac acc gaa           1344
Pro Val Asn Ser Thr Pro Val Asp Phe Ala Tyr Ala Val His Thr Glu
        435                 440                 445 gtg ggg cac cgc tgc atc ggc gcc aaa atc aac ggc aaa ctg gtc gct           1392
Val Gly His Arg Cys Ile Gly Ala Lys Ile Asn Gly Lys Leu Val Ala
    450                 455                 460 ttg gaa acg aaa ctc aaa tcc ggc gat cgt gtt gaa gtc ttt acc tcc           1440
Leu Glu Thr Lys Leu Lys Ser Gly Asp Arg Val Glu Val Phe Thr Ser
465                 470                 475                 480 aag gac caa aac gct ggc cca agt agg gga tgg caa gaa ttt gtt gtc           1488
```

| | | | | | | | | | | | | | | | |
|---|---|---|---|---|---|---|---|---|---|---|---|---|---|---|---|
| | Lys | Asp | Gln | Asn | Ala | Gly | Pro | Ser | Arg | Gly | Trp | Gln | Glu | Phe | Val | Val |
| | | | | 485 | | | | | 490 | | | | | 495 | |

```
tca cct cgt gca aag gcc aag att cgc cag tgg ttt gcc aag gaa cga      1536
Ser Pro Arg Ala Lys Ala Lys Ile Arg Gln Trp Phe Ala Lys Glu Arg
        500             505                 510 cgc gaa gaa tac cta gaa gcc gga cgc gat gcg ctg gca gca gtt att      1584
Arg Glu Glu Tyr Leu Glu Ala Gly Arg Asp Ala Leu Ala Ala Val Ile
            515                 520                 525 cag cgt ggc ggc ctg cca atg cac cgc ttg ttc acc gcg tcc tcc atg      1632
Gln Arg Gly Gly Leu Pro Met His Arg Leu Phe Thr Ala Ser Ser Met
530                 535                 540 aag acg gtg gca aca gag ctg cac tac cca gat gta gat gcg ctc tac      1680
Lys Thr Val Ala Thr Glu Leu His Tyr Pro Asp Val Asp Ala Leu Tyr
545                 550                 555                 560 aca gcc atc ggc tcc ggt tct gta tct gcg caa cac gta gtc aac cgt      1728
Thr Ala Ile Gly Ser Gly Ser Val Ser Ala Gln His Val Val Asn Arg
                565                 570                 575 ctc atg gct atc ttt ggt gac gaa gaa gat gcc gaa gac gca ttg gtt      1776
Leu Met Ala Ile Phe Gly Asp Glu Glu Asp Ala Glu Asp Ala Leu Val
            580                 585                 590 gca cgc acc cca ttc agc gag ctg gtc aac tcc cgt gcc acc acg gaa      1824
Ala Arg Thr Pro Phe Ser Glu Leu Val Asn Ser Arg Ala Thr Thr Glu
        595                 600                 605 agc agc acc ggc atc ctg gtc gaa ggc agc cca gat gtc atg gct aag      1872
Ser Ser Thr Gly Ile Leu Val Glu Gly Ser Pro Asp Val Met Ala Lys
610                 615                 620 ctc gct aaa tgc tgt atg cca gtg cca gga gat gaa atc ttt gga ttc      1920
Leu Ala Lys Cys Cys Met Pro Val Pro Gly Asp Glu Ile Phe Gly Phe
625                 630                 635                 640 gtc acc cgt ggt ggc ggt gtc tcc gta cac cga aca gac tgc acg aat      1968
Val Thr Arg Gly Gly Gly Val Ser Val His Arg Thr Asp Cys Thr Asn
                645                 650                 655 gtg gaa aag ctc aaa gaa gag cca gaa cgc att gtc tcc gtc tcc tgg      2016
Val Glu Lys Leu Lys Glu Glu Pro Glu Arg Ile Val Ser Val Ser Trp
            660                 665                 670 gct tcg gaa ggt caa ggt tca gta ttc tct gcc aca ctg cag ctt gaa      2064
Ala Ser Glu Gly Gln Gly Ser Val Phe Ser Ala Thr Leu Gln Leu Glu
        675                 680                 685 gca ctt gat cgc gca ggc ctg ctc ttt gag ctc acc cgc gta atc aac      2112
Ala Leu Asp Arg Ala Gly Leu Leu Phe Glu Leu Thr Arg Val Ile Asn
690                 695                 700 gaa caa aag gtc tcc gtt acc gca atg aac tcc cat tgc tca gaa gac      2160
Glu Gln Lys Val Ser Val Thr Ala Met Asn Ser His Cys Ser Glu Asp
705                 710                 715                 720 cgc gta gcc acc gtg cgc ttc acc ttt gcg gtc tct gac acc aag cag      2208
Arg Val Ala Thr Val Arg Phe Thr Phe Ala Val Ser Asp Thr Lys Gln
                725                 730                 735 ttg gga tcc ctg atg aca cag ctg cgc aat gcc gaa gga gtg ttt gat      2256
Leu Gly Ser Leu Met Thr Gln Leu Arg Asn Ala Glu Gly Val Phe Asp
            740                 745                 750 gtc tac cga gtg acc tcg ggt ggc tag                                   2283
Val Tyr Arg Val Thr Ser Gly Gly
        755                 760

<210> SEQ ID NO 6
<211> LENGTH: 760
<212> TYPE: PRT
<213> ORGANISM: Corynebacterium glutamicum

<400> SEQUENCE: 6

Met Ser Leu Glu Arg Asn Thr Gln Lys Ser Ser Met Gly Val Arg Ser
```

-continued

```
1               5               10              15
Met Ser Ala Arg Leu Ala Arg Ser Leu Thr Gly Asn Arg Val Arg Thr
                20              25              30

Asn Pro Val Leu Asp Leu Leu Leu Ser Ile His Arg Gln Phe His Pro
            35              40              45

Arg Ala Asp Val Gln Val Leu Glu Arg Ala Tyr Asp Thr Ala Glu Arg
        50              55              60

Leu His Asp Gly Val Ile Arg Lys Ser Gly Asp Pro Tyr Ile Thr His
65              70              75              80

Pro Leu Ala Val Ala Thr Ile Ala Ala Glu Ile Gly Met Asp Thr Thr
                85              90              95

Thr Leu Val Ala Ala Leu Leu His Asp Thr Val Glu Asp Thr Asp Tyr
            100             105             110

Ser Leu Asp Asp Leu Thr Arg Asp Phe Gly Glu Val Ala Arg Leu
        115             120             125

Val Asp Gly Val Thr Lys Leu Asp Lys Val Ala Leu Gly Ala Ala Ala
    130             135             140

Glu Ala Glu Thr Ile Arg Lys Met Ile Val Ala Met Ser Gln Asp Pro
145             150             155             160

Arg Val Leu Val Ile Lys Val Ala Asp Arg Leu His Asn Met Arg Thr
                165             170             175

Met Arg Phe Leu Pro Pro Glu Lys Gln Ala Lys Lys Ala Arg Gln Thr
            180             185             190

Leu Glu Val Ile Ala Pro Leu Ala His Arg Leu Gly Met Ala Ser Val
        195             200             205

Lys Trp Glu Leu Glu Asp Leu Ser Phe Ala Ile Leu Tyr Pro Lys Lys
210             215             220

Tyr Glu Glu Ile Val Arg Leu Val Ala Asp Arg Ala Pro Ser Arg Asp
225             230             235             240

Arg Tyr Leu Lys Glu Ile Ile Asp Gln Val Thr Gly Gly Leu Arg Glu
                245             250             255

Asn Asn Ile Ala Ala Gly Val Leu Gly Arg Pro Lys His Tyr Trp Ser
            260             265             270

Ile Tyr Gln Lys Met Ile Val Arg Gly Arg Asp Phe Asp Asp Ile Phe
        275             280             285

Asp Leu Val Gly Ile Arg Ile Leu Val Asp Asn Val Asn Asn Cys Tyr
    290             295             300

Ala Ala Ile Gly Val Val His Ser Leu Phe Asn Ala Leu Pro Gly Arg
305             310             315             320

Phe Lys Asp Tyr Ile Ser Ala Pro Arg Phe Gly Val Tyr Gln Ser Leu
                325             330             335

His Thr Thr Val Met Gly Pro Gly Gly Lys Pro Leu Glu Val Gln Ala
            340             345             350

Arg Thr His Asp Met His Tyr Asn Ala Glu Phe Gly Ile Ala Ala His
        355             360             365

Trp Arg Tyr Lys Glu Thr Lys Gly Ser His Ser Gly Glu Gln Ala Glu
    370             375             380

Val Asp Gln Met Ala Trp Met Arg Gln Leu Leu Asp Trp Gln Lys Glu
385             390             395             400

Ala Ala Asp Pro Asn Glu Phe Leu Asp Ser Leu Arg Tyr Asp Leu Thr
                405             410             415

Ser Lys Gln Ile Phe Val Phe Thr Pro Lys Gly Asp Val Val Asn Leu
            420             425             430
```

-continued

```
Pro Val Asn Ser Thr Pro Val Asp Phe Ala Tyr Ala Val His Thr Glu
        435                 440                 445

Val Gly His Arg Cys Ile Gly Ala Lys Ile Asn Gly Lys Leu Val Ala
    450                 455                 460

Leu Glu Thr Lys Leu Lys Ser Gly Asp Arg Val Glu Val Phe Thr Ser
465                 470                 475                 480

Lys Asp Gln Asn Ala Gly Pro Ser Arg Gly Trp Gln Glu Phe Val Val
                485                 490                 495

Ser Pro Arg Ala Lys Ala Lys Ile Arg Gln Trp Phe Ala Lys Glu Arg
            500                 505                 510

Arg Glu Glu Tyr Leu Glu Ala Gly Arg Asp Ala Leu Ala Ala Val Ile
        515                 520                 525

Gln Arg Gly Gly Leu Pro Met His Arg Leu Phe Thr Ala Ser Ser Met
    530                 535                 540

Lys Thr Val Ala Thr Glu Leu His Tyr Pro Asp Val Asp Ala Leu Tyr
545                 550                 555                 560

Thr Ala Ile Gly Ser Gly Ser Val Ser Ala Gln His Val Val Asn Arg
                565                 570                 575

Leu Met Ala Ile Phe Gly Asp Glu Glu Asp Ala Glu Asp Ala Leu Val
            580                 585                 590

Ala Arg Thr Pro Phe Ser Glu Leu Val Asn Ser Arg Ala Thr Thr Glu
        595                 600                 605

Ser Ser Thr Gly Ile Leu Val Glu Gly Ser Pro Asp Val Met Ala Lys
    610                 615                 620

Leu Ala Lys Cys Cys Met Pro Val Pro Gly Asp Glu Ile Phe Gly Phe
625                 630                 635                 640

Val Thr Arg Gly Gly Gly Val Ser Val His Arg Thr Asp Cys Thr Asn
                645                 650                 655

Val Glu Lys Leu Lys Glu Glu Pro Glu Arg Ile Val Ser Val Ser Trp
            660                 665                 670

Ala Ser Glu Gly Gln Gly Ser Val Phe Ser Ala Thr Leu Gln Leu Glu
        675                 680                 685

Ala Leu Asp Arg Ala Gly Leu Leu Phe Glu Leu Thr Arg Val Ile Asn
    690                 695                 700

Glu Gln Lys Val Ser Val Thr Ala Met Asn Ser His Cys Ser Glu Asp
705                 710                 715                 720

Arg Val Ala Thr Val Arg Phe Thr Phe Ala Val Ser Asp Thr Lys Gln
                725                 730                 735

Leu Gly Ser Leu Met Thr Gln Leu Arg Asn Ala Glu Gly Val Phe Asp
            740                 745                 750

Val Tyr Arg Val Thr Ser Gly Gly
        755                 760

<210> SEQ ID NO 7
<211> LENGTH: 3800
<212> TYPE: DNA
<213> ORGANISM: Corynebacterium glutamicum
<220> FEATURE:
<221> NAME/KEY: misc_feature
<222> LOCATION: (751)..(3033)
<223> OTHER INFORMATION: rel allele
<220> FEATURE:
<221> NAME/KEY: misc_feature
<222> LOCATION: (863)..(863)
<223> OTHER INFORMATION: C - > T transition
<220> FEATURE:
<221> NAME/KEY: misc_feature
<222> LOCATION: (1535)..(1535)
<223> OTHER INFORMATION: Guanine
```

<400> SEQUENCE: 7

```
aggcgcaact gaagaacaat tgtgggctga agtcccatca attccactag cagcgcaacc    60
ccgagtgttt gtgatagatc gcacagtcgg taacgttgtt gttaatacag acctagccgg   120
tatcggatgg aacatgaccg ttggtccaga agtgaggaat aagtagtgag cgaacaagct   180
ctaagcacct tcgacagggc acgtgaggcc ctggacaaga aacccgata tgtgcaggat    240
ttcccagaaa agggtgtgct ttttgaagac ctcaccccgg tgttgggcga tgcagaatca   300
tttgtggccg tggtgacgc catggctgaa gctgcagaaa aactgaatgc agaaatcatc    360
ggtggcttgg atgcgcgagg attcctcctc ggatctgctg tcgcttacaa actcggccta   420
ggtgtgctgg ctatccgcaa gaagggaaag ctccccccac ctgtggtgac ccaggagtat   480
gaacttgaat acggcactgc agcactcgag ctgcccagta aggaatcga cattgctggt    540
aaaaacatcg ttttgatcga cgatgtgctg gcaaccggcg gcaccttggg cgctgcacgt   600
aaactaattg aatcgtgtga cggacatgtt tccggatatg ttcttgccat tgaggtccca   660
ggcctcggcg gtagggataa tcttggtgat aggcccgtca ttgtggtcag agatcctcag   720
tagaaggatc gaaagaaagg cggcaggaaa atgagtctgg agcgcaacac acaaaaatct   780
tccatgggtg tgcgaagcat gtcagccagg cttgcccgca gcctcacagg aaaccgcgtt   840
cgcaccaacc ctgtgctgga tctgctgctg agcatccacc ggcaatttca cccacgcgcc   900
gacgtacaag tgttggaacg tgcatatgac accgcggaac gtcttcatga tggtgtgatt   960
cgaaaatcgg gcgatccgta tattacccac ccgttggctg tcgccaccat cgccgcggaa  1020
atcggcatgg acaccaccac gctcgtcgca gccttgttgc atgacacggt ggaagacacc  1080
gactactctt tggacgatct cacccgagat ttcgagaag aagttgccag gcttgtcgac  1140
ggtgtcacca agctcgacaa agtcgcacta ggtgctgccg cggaggccga acgattcgc   1200
aaaatgatcg tcgccatgag ccaggacccc cgcgtgctgg tgattaaagt ggccgaccgt  1260
ttgcacaata tgcgcaccat gcggttcctg ccgccggaaa agcaagctaa aaaagcacgc  1320
caaacccttg aagtgattgc tcctttggca caccgcctgg gcatggccag cgtgaaatgg  1380
gaattggaag atctatcctt tgccattttg taccccaaga agtacgaaga gatcgtgcgt  1440
cttgttgccg accgcgcgcc ctctagagac cggtacctca agaaattat tgatcaagtc  1500
accggtggct tgcgcgaaaa caacatcgcg gcaggagtgc ttggtcgacc aaagcactac  1560
tggtctatct atcaaaagat gatcgttcgc ggtcgtgatt ttgacgatat ttttgatctt  1620
gttggcatcc gcatcctggt agacaacgtg aacaactgtt acgccgccat cggtgtcgtg  1680
cactccctgt tcaatgctct gcctggccga ttcaaagact atatttcagc cccgcgcttc  1740
ggtgtctacc aatccctgca caccaccgtg atgggacctg gcggtaagcc tctggaagtt  1800
caggcacgta cccacgacat gcactacaac gccgaattcg gcattgcagc gcactggcga  1860
tacaaagaaa ccaaaggcag ccacagtggc gagcaagccg aagtggatca aatggcgtgg  1920
atgcgccaac ttctggactg gcaaaaagaa gcagccgacc ccaacgagtt cctggacagc  1980
ctgcgctacg atctgacttc caagcagatc ttcgtgttca cacccaaagg tgatgtggtc  2040
aacctgccgg tgaactccac cccggtggac ttcgcctacg cggtgcacac cgaagtgggg  2100
caccgctgca tcggcgccaa aatcaacggc aaactggtcg ctttggaaac gaaactcaaa  2160
tccggcgatc gtgttgaagt cttttacctcc aaggaccaaa acgctggccc aagtagggga  2220
tggcaagaat ttgttgtctc acctcgtgca aaggccaaga ttcgccagtg gtttgccaag  2280
gaacgacgcg aagaatacct agaagccgga cgcgatgcgc tggcagcagt tattcagcgt  2340
```

```
ggcggcctgc caatgcaccg cttgttcacc gcgtcctcca tgaagacggt ggcaacagag      2400
ctgcactacc cagatgtaga tgcgctctac acagccatcg gctccggttc tgtatctgcg      2460
caacacgtag tcaaccgtct catggctatc tttggtgacg aagaagatgc cgaagacgca      2520
ttggttgcac gcaccccatt cagcgagctg gtcaactccc gtgccaccac ggaaagcagc      2580
accggcatcc tggtcgaagg cagcccagat gtcatggcta agctcgctaa atgctgtatg      2640
ccagtgccag gagatgaaat cttggattc gtcacccgtg gtggcggtgt ctccgtacac       2700
cgaacagact gcacgaatgt ggaaaagctc aaagaagagc cagaacgcat tgtctccgtc      2760
tcctgggctt cggaaggtca aggttcagta ttctctgcca cactgcagct tgaagcactt      2820
gatcgcgcag gcctgctctt tgagctcacc cgcgtaatca cgaacaaaa ggtctccgtt       2880 accgcaatga actcccattg ctcagaagac cgcgtagcca ccgtgcgctt cacctttgcg      2940
gtctctgaca ccaagcagtt gggatccctg atgacacagc tgcgcaatgc cgaaggagtg      3000
tttgatgtct accgagtgac ctcgggtggc tagaggcctt tagattgtga aaaagccttg      3060
ggcttcaacc accgtgtgtt gacacggttt tggggttgga tttaacgctg gaaattttac      3120
tgcaatgaac gctggaaagc agtagcgaag gtcaaaccag cgctgaggac gccaacgatg      3180
ccagtaataa cgacgacgta atccaaaatg gtgtcagagt caatgtcaga agatccgttg      3240
gtgctaccgt ttcttcttct acggtgtcag ccacgtacac aacctgtgct ggtgcgactt      3300
cttcagcctg tgcaggaacg gagatggagg ttgctgccat tgcagcagct gtgccgagtg      3360
cgacgagggg agtacgagaa aatagcttca ttgctaaacc ccttaggttt aaatattcga      3420
atacgaaagt tactttatgt gcactttcac cattgtgcaa ctatatgtgc aggtcaaagc      3480
tgatattttg ctaagaaaag tgcaaagcga ttcgagctga cgcgcagccc atatcgtcaa      3540
aaaatccttt gtgaatggtg attcacaaag gattagtcgc gtaaggcgga aattacttca      3600
ggaaggaatc cagcttggta ctgaaggtta aatggtggt tagtgcaccg atgactgctg       3660
tgatgatctt gatccagttt tcgatgttgt cagtgtcgga agaaccgctg gaaggctctt      3720
cgctggacgg gtcttcgttg aaatcaaagt taacgtaaac ttctgcttca acgcctgctt      3780
cgttcttggc aatgatcttt                                                  3800

<210> SEQ ID NO 8
<211> LENGTH: 760
<212> TYPE: PRT
<213> ORGANISM: Corynebacterium glutamicum

<400> SEQUENCE: 8

Met Ser Leu Glu Arg Asn Thr Gln Lys Ser Ser Met Gly Val Arg Ser
1               5                   10                  15

Met Ser Ala Arg Leu Ala Arg Ser Leu Thr Gly Asn Arg Val Arg Thr
            20                  25                  30

Asn Pro Val Leu Asp Leu Leu Ser Ile His Arg Gln Phe His Pro
        35                  40                  45

Arg Ala Asp Val Gln Val Leu Glu Arg Ala Tyr Asp Thr Ala Glu Arg
    50                  55                  60

Leu His Asp Gly Val Ile Arg Lys Ser Gly Asp Pro Tyr Ile Thr His
65                  70                  75                  80

Pro Leu Ala Val Ala Thr Ile Ala Ala Glu Ile Gly Met Asp Thr Thr
                85                  90                  95

Thr Leu Val Ala Ala Leu Leu His Asp Thr Val Glu Asp Thr Asp Tyr
            100                 105                 110
```

```
Ser Leu Asp Asp Leu Thr Arg Asp Phe Gly Glu Glu Val Ala Arg Leu
    115                 120                 125

Val Asp Gly Val Thr Lys Leu Asp Lys Val Ala Leu Gly Ala Ala Ala
130                 135                 140

Glu Ala Glu Thr Ile Arg Lys Met Ile Val Ala Met Ser Gln Asp Pro
145                 150                 155                 160

Arg Val Leu Val Ile Lys Val Ala Asp Arg Leu His Asn Met Arg Thr
                165                 170                 175

Met Arg Phe Leu Pro Pro Glu Lys Gln Ala Lys Lys Ala Arg Gln Thr
            180                 185                 190

Leu Glu Val Ile Ala Pro Leu Ala His Arg Leu Gly Met Ala Ser Val
        195                 200                 205

Lys Trp Glu Leu Glu Asp Leu Ser Phe Ala Ile Leu Tyr Pro Lys Lys
210                 215                 220

Tyr Glu Glu Ile Val Arg Leu Val Ala Asp Arg Ala Pro Ser Arg Asp
225                 230                 235                 240

Arg Tyr Leu Lys Glu Ile Ile Asp Gln Val Thr Gly Gly Leu Arg Glu
                245                 250                 255

Asn Asn Ile Ala Ala Gly Val Leu Gly Arg Pro Lys His Tyr Trp Ser
            260                 265                 270

Ile Tyr Gln Lys Met Ile Val Arg Gly Arg Asp Phe Asp Asp Ile Phe
        275                 280                 285

Asp Leu Val Gly Ile Arg Ile Leu Val Asp Asn Val Asn Asn Cys Tyr
290                 295                 300

Ala Ala Ile Gly Val Val His Ser Leu Phe Asn Ala Leu Pro Gly Arg
305                 310                 315                 320

Phe Lys Asp Tyr Ile Ser Ala Pro Arg Phe Gly Val Tyr Gln Ser Leu
                325                 330                 335

His Thr Thr Val Met Gly Pro Gly Lys Pro Leu Glu Val Gln Ala
            340                 345                 350

Arg Thr His Asp Met His Tyr Asn Ala Glu Phe Gly Ile Ala Ala His
        355                 360                 365

Trp Arg Tyr Lys Glu Thr Lys Gly Ser His Ser Gly Gln Ala Glu
370                 375                 380

Val Asp Gln Met Ala Trp Met Arg Gln Leu Leu Asp Trp Gln Lys Glu
385                 390                 395                 400

Ala Ala Asp Pro Asn Glu Phe Leu Asp Ser Leu Arg Tyr Asp Leu Thr
                405                 410                 415

Ser Lys Gln Ile Phe Val Phe Thr Pro Lys Gly Asp Val Val Asn Leu
            420                 425                 430

Pro Val Asn Ser Thr Pro Val Asp Phe Ala Tyr Ala Val His Thr Glu
        435                 440                 445

Val Gly His Arg Cys Ile Gly Ala Lys Ile Asn Gly Lys Leu Val Ala
450                 455                 460

Leu Glu Thr Lys Leu Lys Ser Gly Asp Arg Val Glu Val Phe Thr Ser
465                 470                 475                 480

Lys Asp Gln Asn Ala Gly Pro Ser Arg Gly Trp Gln Glu Phe Val Val
                485                 490                 495

Ser Pro Arg Ala Lys Ala Lys Ile Arg Gln Trp Phe Ala Lys Glu Arg
            500                 505                 510

Arg Glu Glu Tyr Leu Glu Ala Gly Arg Asp Ala Leu Ala Ala Val Ile
        515                 520                 525

Gln Arg Gly Gly Leu Pro Met His Arg Leu Phe Thr Ala Ser Ser Met
530                 535                 540
```

```
Lys Thr Val Ala Thr Glu Leu His Tyr Pro Asp Val Asp Ala Leu Tyr
545                 550                 555                 560

Thr Ala Ile Gly Ser Gly Ser Val Ser Ala Gln His Val Val Asn Arg
            565                 570                 575

Leu Met Ala Ile Phe Gly Asp Glu Glu Asp Ala Glu Asp Ala Leu Val
                580                 585                 590

Ala Arg Thr Pro Phe Ser Glu Leu Val Asn Ser Arg Ala Thr Thr Glu
            595                 600                 605

Ser Ser Thr Gly Ile Leu Val Glu Gly Ser Pro Asp Val Met Ala Lys
        610                 615                 620

Leu Ala Lys Cys Cys Met Pro Val Pro Gly Asp Glu Ile Phe Gly Phe
625                 630                 635                 640

Val Thr Arg Gly Gly Gly Val Ser Val His Arg Thr Asp Cys Thr Asn
                645                 650                 655

Val Glu Lys Leu Lys Glu Glu Pro Glu Arg Ile Val Ser Val Ser Trp
            660                 665                 670

Ala Ser Glu Gly Gln Gly Ser Val Phe Ser Ala Thr Leu Gln Leu Glu
        675                 680                 685

Ala Leu Asp Arg Ala Gly Leu Leu Phe Glu Leu Thr Arg Val Ile Asn
    690                 695                 700

Glu Gln Lys Val Ser Val Thr Ala Met Asn Ser His Cys Ser Glu Asp
705                 710                 715                 720

Arg Val Ala Thr Val Arg Phe Thr Phe Ala Val Ser Asp Thr Lys Gln
                725                 730                 735

Leu Gly Ser Leu Met Thr Gln Leu Arg Asn Ala Glu Gly Val Phe Asp
            740                 745                 750

Val Tyr Arg Val Thr Ser Gly Gly
        755                 760

<210> SEQ ID NO 9
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild-type gene

<400> SEQUENCE: 9 gtg gcc ctg gtc gta cag aaa tat ggc ggt tcc tcg ctt gag agt gcg      48
Val Ala Leu Val Val Gln Lys Tyr Gly Gly Ser Ser Leu Glu Ser Ala
1               5                  10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
```

-continued

| | | | | | | | | | | | | |
|---|---|---|---|---|---|---|---|---|---|---|---|---|
| Gly | Ser | Gln | Ala | Gly | Val | Leu | Thr | Thr | Glu | Arg | His | Gly | Asn | Ala | Arg |
| | | | 100 | | | | | 105 | | | | 110 | | | |

| att | gtt | gat | gtc | act | cca | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly |
| | | | 115 | | | | | 120 | | | | 125 | | | |

| aag | atc | tgc | att | gtt | gct | ggt | ttc | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg |
| | | 130 | | | | | 135 | | | | | 140 | | | |

| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala |
| 145 | | | | | 150 | | | | | 155 | | | | | 160 |

| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val |
| | | | | 165 | | | | | 170 | | | | | 175 | |

| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys |
| | | | 180 | | | | | 185 | | | | | 190 | | |

| ctg | gaa | aag | ctc | agc | ttc | gaa | gaa | atg | ctg | gaa | ctt | gct | gct | gtt | ggc | 624 |
| Leu | Glu | Lys | Leu | Ser | Phe | Glu | Glu | Met | Leu | Glu | Leu | Ala | Ala | Val | Gly |
| | | | 195 | | | | | 200 | | | | | 205 | | |

| tcc | aag | att | ttg | gtg | ctg | cgc | agt | gtt | gaa | tac | gct | cgt | gca | ttc | aat | 672 |
| Ser | Lys | Ile | Leu | Val | Leu | Arg | Ser | Val | Glu | Tyr | Ala | Arg | Ala | Phe | Asn |
| | 210 | | | | | 215 | | | | | 220 | | | | |

| gtg | cca | ctt | cgc | gta | cgc | tcg | tct | tat | agt | aat | gat | ccc | ggc | act | ttg | 720 |
| Val | Pro | Leu | Arg | Val | Arg | Ser | Ser | Tyr | Ser | Asn | Asp | Pro | Gly | Thr | Leu |
| 225 | | | | | 230 | | | | | 235 | | | | | 240 |

| att | gcc | ggc | tct | atg | gag | gat | att | cct | gtg | gaa | gaa | gca | gtc | ctt | acc | 768 |
| Ile | Ala | Gly | Ser | Met | Glu | Asp | Ile | Pro | Val | Glu | Glu | Ala | Val | Leu | Thr |
| | | | | 245 | | | | | 250 | | | | | 255 | |

| ggt | gtc | gca | acc | gac | aag | tcc | gaa | gcc | aaa | gta | acc | gtt | ctg | ggt | att | 816 |
| Gly | Val | Ala | Thr | Asp | Lys | Ser | Glu | Ala | Lys | Val | Thr | Val | Leu | Gly | Ile |
| | | | 260 | | | | | 265 | | | | | 270 | | |

| tcc | gat | aag | cca | ggc | gag | gct | gcg | aag | gtt | ttc | cgt | gcg | ttg | gct | gat | 864 |
| Ser | Asp | Lys | Pro | Gly | Glu | Ala | Ala | Lys | Val | Phe | Arg | Ala | Leu | Ala | Asp |
| | | 275 | | | | | 280 | | | | | 285 | | | |

| gca | gaa | atc | aac | att | gac | atg | gtt | ctg | cag | aac | gtc | tct | tct | gta | gaa | 912 |
| Ala | Glu | Ile | Asn | Ile | Asp | Met | Val | Leu | Gln | Asn | Val | Ser | Ser | Val | Glu |
| | 290 | | | | | 295 | | | | | 300 | | | | |

| gac | ggc | acc | acc | gac | atc | acc | ttc | acc | tgc | cct | cgt | tcc | gac | ggc | cgc | 960 |
| Asp | Gly | Thr | Thr | Asp | Ile | Thr | Phe | Thr | Cys | Pro | Arg | Ser | Asp | Gly | Arg |
| 305 | | | | | 310 | | | | | 315 | | | | | 320 |

| cgc | gcg | atg | gag | atc | ttg | aag | aag | ctt | cag | gtt | cag | ggc | aac | tgg | acc | 1008 |
| Arg | Ala | Met | Glu | Ile | Leu | Lys | Lys | Leu | Gln | Val | Gln | Gly | Asn | Trp | Thr |
| | | | | 325 | | | | | 330 | | | | | 335 | |

| aat | gtg | ctt | tac | gac | gac | cag | gtc | ggc | aaa | gtc | tcc | ctc | gtg | ggt | gct | 1056 |
| Asn | Val | Leu | Tyr | Asp | Asp | Gln | Val | Gly | Lys | Val | Ser | Leu | Val | Gly | Ala |
| | | | 340 | | | | | 345 | | | | | 350 | | |

| ggc | atg | aag | tct | cac | cca | ggt | gtt | acc | gca | gag | ttc | atg | gaa | gct | ctg | 1104 |
| Gly | Met | Lys | Ser | His | Pro | Gly | Val | Thr | Ala | Glu | Phe | Met | Glu | Ala | Leu |
| | | 355 | | | | | 360 | | | | | 365 | | | |

| cgc | gat | gtc | aac | gtg | aac | atc | gaa | ttg | att | tcc | acc | tct | gag | att | cgt | 1152 |
| Arg | Asp | Val | Asn | Val | Asn | Ile | Glu | Leu | Ile | Ser | Thr | Ser | Glu | Ile | Arg |
| | 370 | | | | | 375 | | | | | 380 | | | | |

| att | tcc | gtg | ctg | atc | cgt | gaa | gat | gat | ctg | gat | gct | gct | gca | cgt | gca | 1200 |
| Ile | Ser | Val | Leu | Ile | Arg | Glu | Asp | Asp | Leu | Asp | Ala | Ala | Ala | Arg | Ala |
| 385 | | | | | 390 | | | | | 395 | | | | | 400 |

| ttg | cat | gag | cag | ttc | cag | ctg | ggc | ggc | gaa | gac | gaa | gcc | gtc | gtt | tat | 1248 |
| Leu | His | Glu | Gln | Phe | Gln | Leu | Gly | Gly | Glu | Asp | Glu | Ala | Val | Val | Tyr |
| | | | | 405 | | | | | 410 | | | | | 415 | |

| gca | ggc | acc | gga | cgc | | | | | | | | | | | | 1263 |
| Ala | Gly | Thr | Gly | Arg | | | | | | | | | | | | |

Ala Gly Thr Gly Arg
            420

<210> SEQ ID NO 10
<211> LENGTH: 421
<212> TYPE: PRT
<213> ORGANISM: Corynebacterium glutamicum

<400> SEQUENCE: 10

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

```
Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 11
<211> LENGTH: 117
<212> TYPE: DNA
<213> ORGANISM: Corynebacterium glutamicum
<220> FEATURE:
<221> NAME/KEY: CDS
<222> LOCATION: (1)..(117)
<220> FEATURE:
<221> NAME/KEY: misc_feature
<222> LOCATION: (20)..(20)
<223> OTHER INFORMATION: The 'Xaa' at location 20 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (58)..(60)
<223> OTHER INFORMATION: n is a, c, g, or t

<400> SEQUENCE: 11 gcc agg ctt gcc cgc agc ctc aca gga aac cgc gtt cgc acc aac cct      48
Ala Arg Leu Ala Arg Ser Leu Thr Gly Asn Arg Val Arg Thr Asn Pro
1               5                   10                  15 gtg ctg gat nnn ctg ctg agc atc cac cgg caa ttt cac cca cgc gcc      96
Val Leu Asp Xaa Leu Leu Ser Ile His Arg Gln Phe His Pro Arg Ala
                20                  25                  30 gac gta caa gtg ttg gaa cgt                                         117
Asp Val Gln Val Leu Glu Arg
        35

<210> SEQ ID NO 12
<211> LENGTH: 39
<212> TYPE: PRT
<213> ORGANISM: Corynebacterium glutamicum
<220> FEATURE:
<221> NAME/KEY: misc_feature
<222> LOCATION: (20)..(20)
<223> OTHER INFORMATION: The 'Xaa' at location 20 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 12

Ala Arg Leu Ala Arg Ser Leu Thr Gly Asn Arg Val Arg Thr Asn Pro
1               5                   10                  15

Val Leu Asp Xaa Leu Leu Ser Ile His Arg Gln Phe His Pro Arg Ala
                20                  25                  30

Asp Val Gln Val Leu Glu Arg
        35

<210> SEQ ID NO 13
<211> LENGTH: 117
<212> TYPE: DNA
<213> ORGANISM: Corynebacterium glutamicum
<220> FEATURE:
<221> NAME/KEY: CDS
<222> LOCATION: (1)..(117)

<400> SEQUENCE: 13 gcc agg ctt gcc cgc agc ctc aca gga aac cgc gtt cgc acc aac cct      48
```

```
Ala Arg Leu Ala Arg Ser Leu Thr Gly Asn Arg Val Arg Thr Asn Pro
1               5                   10                  15 gtg ctg gat ctg ctg agc atc cac cgg caa ttt cac cca cgc gcc         96
Val Leu Asp Leu Leu Ser Ile His Arg Gln Phe His Pro Arg Ala
            20                  25                  30 gac gta caa gtg ttg gaa cgt                                         117
Asp Val Gln Val Leu Glu Arg
        35
```

<210> SEQ ID NO 14
<211> LENGTH: 39
<212> TYPE: PRT
<213> ORGANISM: Corynebacterium glutamicum

<400> SEQUENCE: 14

```
Ala Arg Leu Ala Arg Ser Leu Thr Gly Asn Arg Val Arg Thr Asn Pro
1               5                   10                  15

Val Leu Asp Leu Leu Ser Ile His Arg Gln Phe His Pro Arg Ala
            20                  25                  30

Asp Val Gln Val Leu Glu Arg
        35
```

<210> SEQ ID NO 15
<211> LENGTH: 1530
<212> TYPE: DNA
<213> ORGANISM: Corynebacterium glutamicum
<220> FEATURE:
<221> NAME/KEY: misc_feature
<222> LOCATION: (1)..(2)
<220> FEATURE:
<221> NAME/KEY: misc_feature
<222> LOCATION: (3)..(8)
<223> OTHER INFORMATION: EcoRI restriction cleavage site
<220> FEATURE:
<221> NAME/KEY: misc_feature
<222> LOCATION: (639)..(1520)
<223> OTHER INFORMATION: coding frame
<220> FEATURE:
<221> NAME/KEY: mutation
<222> LOCATION: (751)..(751)
<220> FEATURE:
<221> NAME/KEY: misc_feature
<222> LOCATION: (1423)..(1423)
<223> OTHER INFORMATION: Guanine
<220> FEATURE:
<221> NAME/KEY: misc_feature
<222> LOCATION: (1523)..(1528)
<223> OTHER INFORMATION: EcoRI restriction cleavage site
<220> FEATURE:
<221> NAME/KEY: misc_feature
<222> LOCATION: (1529)..(1530)

<400> SEQUENCE: 15

```
gcgaattcta tcggatggaa catgaccgtt ggtccagaag tgaggaataa gtagtgagcg    60
aacaagctct aagcaccttc gacagggcac gtgaggccct ggacaagaaa acccgatatg   120
tgcaggattt cccagaaaag ggtgtgcttt ttgaagacct caccccggtg ttgggcgatg   180
cagaatcatt tgtggccgtg gtggacgcca tggctgaagc tgcagaaaaa ctgaatgcag   240
aaatcatcgg tggcttggat gcgcgaggat tcctcctcgg atctgctgtc gcttacaaac   300
tcggcctagg tgtgctggct atccgcaaga agggaaagct ccccccacct gtggtgaccc   360
aggagtatga acttgaatac ggcactgcag cactcgagct gcccagtgaa ggaatcgaca   420
ttgctggtaa aaacatcgtt ttgatcgacg atgtgctggc aaccggcggc accttgggcg   480
ctgcacgtaa actaattgaa tcgtgtgacg gacatgtttc cggatatgtt cttgccattg   540
aggtcccagg cctcggcggt aggataatc ttggtgatag gcccgtcatt gtggtcagag   600
```

```
atcctcagta gaaggatcga aagaaaggcg gcaggaaaat gagtctggag cgcaacacac      660
aaaaatcttc catgggtgtg cgaagcatgt cagccaggct tgcccgcagc ctcacaggaa      720
accgcgttcg caccaaccct gtgctggatc tgctgctgag catccaccgg caatttcacc      780
cacgcgccga cgtacaagtg ttggaacgtg catatgacac cgcggaacgt cttcatgatg      840
gtgtgattcg aaaatcgggc gatccgtata ttacccaccc gttggctgtc gccaccatcg      900
ccgcggaaat cggcatggac accaccacgc tcgtcgcagc cttgttgcat gacacggtgg      960
aagacaccga ctactctttg gacgatctca cccgagattt cggagaagaa gttgccaggc     1020
ttgtcgacgg tgtcaccaag ctcgacaaag tcgcactagg tgctgccgcg gaggccgaaa     1080
cgattcgcaa aatgatcgtc gccatgagcc aggaccccg cgtgctggtg attaaagtgg      1140
ccgaccgttt gcacaatatg cgcaccatgc ggttcctgcc gccggaaaag caagctaaaa     1200
aagcacgcca acccttgaa gtgattgctc ctttggcaca ccgcctgggc atggccagcg      1260
tgaaatggga attggaagat ctatcctttg ccattttgta ccccaagaag tacgaagaga     1320
tcgtgcgtct tgttgccgac cgcgcgccct ctagagaccg gtacctcaaa gaaattattg     1380
atcaagtcac cggtggcttg cgcgaaaaca acatcgcggc aggagtgctt ggtcgaccaa     1440
agcactactg gtctatctat caaaagatga tcgttcgcgg tcgtgatttt gacgatattt     1500
ttgatcttgt tggcatccgc atgaattcgc                                      1530
```

<210> SEQ ID NO 16
<211> LENGTH: 294
<212> TYPE: PRT
<213> ORGANISM: Corynebacterium glutamicum

<400> SEQUENCE: 16

```
Met Ser Leu Glu Arg Asn Thr Gln Lys Ser Met Gly Val Arg Ser
1               5                   10                  15

Met Ser Ala Arg Leu Ala Arg Ser Leu Thr Gly Asn Arg Val Arg Thr
            20                  25                  30

Asn Pro Val Leu Asp Leu Leu Leu Ser Ile His Arg Gln Phe His Pro
        35                  40                  45

Arg Ala Asp Val Gln Val Leu Glu Arg Ala Tyr Asp Thr Ala Glu Arg
    50                  55                  60

Leu His Asp Gly Val Ile Arg Lys Ser Gly Asp Pro Tyr Ile Thr His
65                  70                  75                  80

Pro Leu Ala Val Ala Thr Ile Ala Ala Glu Ile Gly Met Asp Thr Thr
                85                  90                  95

Thr Leu Val Ala Ala Leu Leu His Asp Thr Val Glu Asp Thr Asp Tyr
            100                 105                 110

Ser Leu Asp Asp Leu Thr Arg Asp Phe Gly Glu Glu Val Ala Arg Leu
        115                 120                 125

Val Asp Gly Val Thr Lys Leu Asp Lys Val Ala Leu Gly Ala Ala Ala
    130                 135                 140

Glu Ala Glu Thr Ile Arg Lys Met Ile Val Ala Met Ser Gln Asp Pro
145                 150                 155                 160

Arg Val Leu Val Ile Lys Val Ala Asp Arg Leu His Asn Met Arg Thr
                165                 170                 175

Met Arg Phe Leu Pro Pro Glu Lys Gln Ala Lys Lys Ala Arg Gln Thr
            180                 185                 190

Leu Glu Val Ile Ala Pro Leu Ala His Arg Leu Gly Met Ala Ser Val
        195                 200                 205
```

-continued

```
Lys Trp Glu Leu Glu Asp Leu Ser Phe Ala Ile Leu Tyr Pro Lys Lys
    210                 215                 220

Tyr Glu Glu Ile Val Arg Leu Val Ala Asp Arg Ala Pro Ser Arg Asp
225                 230                 235                 240

Arg Tyr Leu Lys Glu Ile Ile Asp Gln Val Thr Gly Gly Leu Arg Glu
                245                 250                 255

Asn Asn Ile Ala Ala Gly Val Leu Gly Arg Pro Lys His Tyr Trp Ser
            260                 265                 270

Ile Tyr Gln Lys Met Ile Val Arg Gly Arg Asp Phe Asp Asp Ile Phe
        275                 280                 285

Asp Leu Val Gly Ile Arg
    290
```

<210> SEQ ID NO 17
<211> LENGTH: 1311
<212> TYPE: DNA
<213> ORGANISM: Corynebacterium glutamicum
<220> FEATURE:
<221> NAME/KEY: CDS
<222> LOCATION: (1)..(1308)
<223> OTHER INFORMATION: ilvA wild-type gene

<400> SEQUENCE: 17

```
atg agt gaa aca tac gtg tct gag aaa agt cca gga gtg atg gct agc      48
Met Ser Glu Thr Tyr Val Ser Glu Lys Ser Pro Gly Val Met Ala Ser
1               5                   10                  15 gga gcg gag ctg att cgt gcc gcc gac att caa acg gcg cag gca cga      96
Gly Ala Glu Leu Ile Arg Ala Ala Asp Ile Gln Thr Ala Gln Ala Arg
                20                  25                  30 att tcc tcc gtc att gca cca act cca ttg cag tat tgc cct cgt ctt     144
Ile Ser Ser Val Ile Ala Pro Thr Pro Leu Gln Tyr Cys Pro Arg Leu
            35                  40                  45 tct gag gaa acc gga gcg gaa atc tac ctt aag cgt gag gat ctg cag     192
Ser Glu Glu Thr Gly Ala Glu Ile Tyr Leu Lys Arg Glu Asp Leu Gln
        50                  55                  60 gat gtt cgt tcc tac aag atc cgc ggt gcg ctg aac tct gga gcg cag     240
Asp Val Arg Ser Tyr Lys Ile Arg Gly Ala Leu Asn Ser Gly Ala Gln
65                  70                  75                  80 ctc acc caa gag cag cgc gat gca ggt atc gtt gcc gca tct gca ggt     288
Leu Thr Gln Glu Gln Arg Asp Ala Gly Ile Val Ala Ala Ser Ala Gly
                85                  90                  95 aac cat gcc cag ggc gtg gcc tat gtg tgc aag tcc ttg ggc gtt cag     336
Asn His Ala Gln Gly Val Ala Tyr Val Cys Lys Ser Leu Gly Val Gln
                100                 105                 110 gga cgc atc tat gtt cct gtg cag act cca aag caa aag cgt gac cgc     384
Gly Arg Ile Tyr Val Pro Val Gln Thr Pro Lys Gln Lys Arg Asp Arg
            115                 120                 125 atc atg gtt cac ggc gga gag ttt gtc tcc ttg gtg gtc act ggc aat     432
Ile Met Val His Gly Gly Glu Phe Val Ser Leu Val Val Thr Gly Asn
        130                 135                 140 aac ttc gac gaa gca tcg gct gca gcg cat gaa gat gca gag cgc acc     480
Asn Phe Asp Glu Ala Ser Ala Ala Ala His Glu Asp Ala Glu Arg Thr
145                 150                 155                 160 ggc gca acg ctg atc gag cct ttc gat gct cgc aac acc gtc atc ggt     528
Gly Ala Thr Leu Ile Glu Pro Phe Asp Ala Arg Asn Thr Val Ile Gly
                165                 170                 175 cag ggc acc gtg gct gct gag atc ttg tcg cag ctg act tcc atg ggc     576
Gln Gly Thr Val Ala Ala Glu Ile Leu Ser Gln Leu Thr Ser Met Gly
            180                 185                 190 aag agt gca gat cac gtg atg gtt cca gtc ggc ggt ggc gga ctt ctt     624
Lys Ser Ala Asp His Val Met Val Pro Val Gly Gly Gly Gly Leu Leu
```

```
                195                 200                 205
gca ggt gtg gtc agc tac atg gct gat atg gca cct cgc act gcg atc      672
Ala Gly Val Val Ser Tyr Met Ala Asp Met Ala Pro Arg Thr Ala Ile
210                 215                 220 gtt ggt atc gaa cca gcg gga gca gca tcc atg cag gct gca ttg cac      720
Val Gly Ile Glu Pro Ala Gly Ala Ala Ser Met Gln Ala Ala Leu His
225                 230                 235                 240 aat ggt gga cca atc act ttg gag act gtt gat ccc ttt gtg gac ggc      768
Asn Gly Gly Pro Ile Thr Leu Glu Thr Val Asp Pro Phe Val Asp Gly
                245                 250                 255 gca gca gtc aaa cgt gtc gga gat ctc aac tac acc atc gtg gag aag      816
Ala Ala Val Lys Arg Val Gly Asp Leu Asn Tyr Thr Ile Val Glu Lys
            260                 265                 270 aac cag ggt cgc gtg cac atg atg agc gcg acc gag ggc gct gtg tgt      864
Asn Gln Gly Arg Val His Met Met Ser Ala Thr Glu Gly Ala Val Cys
        275                 280                 285 act gag atg ctc gat ctt tac caa aac gaa ggc atc atc gcg gag cct      912
Thr Glu Met Leu Asp Leu Tyr Gln Asn Glu Gly Ile Ile Ala Glu Pro
290                 295                 300 gct ggc gcg ctg tct atc gct ggg ttg aag gaa atg tcc ttt gca cct      960
Ala Gly Ala Leu Ser Ile Ala Gly Leu Lys Glu Met Ser Phe Ala Pro
305                 310                 315                 320 ggt tct gtc gtg gtg tgc atc atc tct ggt ggc aac aac gat gtg ctg     1008
Gly Ser Val Val Val Cys Ile Ile Ser Gly Gly Asn Asn Asp Val Leu
                325                 330                 335 cgt tat gcg gaa atc gct gag cgc tcc ttg gtg cac cgc ggt ttg aag     1056
Arg Tyr Ala Glu Ile Ala Glu Arg Ser Leu Val His Arg Gly Leu Lys
            340                 345                 350 cac tac ttc ttg gtg aac ttc ccg caa aag cct ggt cag ttg cgt cac     1104
His Tyr Phe Leu Val Asn Phe Pro Gln Lys Pro Gly Gln Leu Arg His
        355                 360                 365 ttc ctg gaa gat atc ctg gga ccg gat gat gac atc acg ctg ttt gag     1152
Phe Leu Glu Asp Ile Leu Gly Pro Asp Asp Asp Ile Thr Leu Phe Glu
370                 375                 380 tac ctc aag cgc aac aac cgt gag acc ggt act gcg ttg gtg ggt att     1200
Tyr Leu Lys Arg Asn Asn Arg Glu Thr Gly Thr Ala Leu Val Gly Ile
385                 390                 395                 400 cac ttg agt gaa gca tca gga ttg gat tct ttg ctg gaa cgt atg gag     1248
His Leu Ser Glu Ala Ser Gly Leu Asp Ser Leu Leu Glu Arg Met Glu
                405                 410                 415 gaa tcg gca att gat tcc cgt cgc ctc gag ccg ggc acc cct gag tac     1296
Glu Ser Ala Ile Asp Ser Arg Arg Leu Glu Pro Gly Thr Pro Glu Tyr
            420                 425                 430 gaa tac ttg acc taa                                                  1311
Glu Tyr Leu Thr
        435

<210> SEQ ID NO 18
<211> LENGTH: 436
<212> TYPE: PRT
<213> ORGANISM: Corynebacterium glutamicum

<400> SEQUENCE: 18

Met Ser Glu Thr Tyr Val Ser Glu Lys Ser Pro Gly Val Met Ala Ser
1               5                   10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
```

```
                50                  55                  60
Asp Val Arg Ser Tyr Lys Ile Arg Gly Ala Leu Asn Ser Gly Ala Gln
 65                  70                  75                  80

Leu Thr Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
                100                 105                 110

Gly Arg Ile Tyr Val Pro Val Gln Thr Pro Lys Gln Lys Arg Asp Arg
                115                 120                 125

Ile Met Val His Gly Gly Glu Phe Val Ser Leu Val Val Thr Gly Asn
130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
                180                 185                 190

Lys Ser Ala Asp His Val Met Val Pro Val Gly Gly Gly Gly Leu Leu
                195                 200                 205

Ala Gly Val Val Ser Tyr Met Ala Asp Met Ala Pro Arg Thr Ala Ile
                210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
                260                 265                 270

Asn Gln Gly Arg Val His Met Met Ser Ala Thr Glu Gly Ala Val Cys
                275                 280                 285

Thr Glu Met Leu Asp Leu Tyr Gln Asn Glu Gly Ile Ile Ala Glu Pro
                290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
                340                 345                 350

His Tyr Phe Leu Val Asn Phe Pro Gln Lys Pro Gly Gln Leu Arg His
                355                 360                 365

Phe Leu Glu Asp Ile Leu Gly Pro Asp Asp Ile Thr Leu Phe Glu
370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
                420                 425                 430

Glu Tyr Leu Thr
        435

<210> SEQ ID NO 19
<211> LENGTH: 28
<212> TYPE: DNA
<213> ORGANISM: Artificial sequence
<220> FEATURE:
```

-continued

<223> OTHER INFORMATION: Synthetic Primer rel_XL_A1
<220> FEATURE:
<221> NAME/KEY: misc_feature
<222> LOCATION: (1)..(2)
<220> FEATURE:
<221> NAME/KEY: misc_feature
<222> LOCATION: (3)..(8)
<223> OTHER INFORMATION: EcoRI restriction cleavage site

<400> SEQUENCE: 19
gcgaattcta tcggatggaa catgaccg                                28

<210> SEQ ID NO 20
<211> LENGTH: 28
<212> TYPE: DNA
<213> ORGANISM: Artificial sequence
<220> FEATURE:
<223> OTHER INFORMATION: Synthetic  Primer rel_XL_E1
<220> FEATURE:
<221> NAME/KEY: misc_feature
<222> LOCATION: (1)..(2)
<220> FEATURE:
<221> NAME/KEY: misc_feature
<222> LOCATION: (3)..(8)
<223> OTHER INFORMATION: EcoRI restriction cleavage site

<400> SEQUENCE: 20
gcgaattcat gcggatgcca acaagatc                                28

<210> SEQ ID NO 21
<211> LENGTH: 2283
<212> TYPE: DNA
<213> ORGANISM: Corynebacterium glutamicum
<220> FEATURE:
<221> NAME/KEY: CDS
<222> LOCATION: (1)..(2280)
<223> OTHER INFORMATION: rel wild-type gene according to EP 1 108 790
<220> FEATURE:
<221> NAME/KEY: misc_feature
<222> LOCATION: (785)..(785)
<223> OTHER INFORMATION: Adenine

<400> SEQUENCE: 21

```
atg agt ctg gag cgc aac aca caa aaa tct tcc atg ggt gtg cga agc      48
Met Ser Leu Glu Arg Asn Thr Gln Lys Ser Ser Met Gly Val Arg Ser
1               5                   10                  15 atg tca gcc agg ctt gcc cgc agc ctc aca gga aac cgc gtt cgc acc      96
Met Ser Ala Arg Leu Ala Arg Ser Leu Thr Gly Asn Arg Val Arg Thr
            20                  25                  30 aac cct gtg ctg gat ccg ctg ctg agc atc cac cgg caa ttt cac cca     144
Asn Pro Val Leu Asp Pro Leu Leu Ser Ile His Arg Gln Phe His Pro
        35                  40                  45 cgc gcc gac gta caa gtg ttg gaa cgt gca tat gac acc gcg gaa cgt     192
Arg Ala Asp Val Gln Val Leu Glu Arg Ala Tyr Asp Thr Ala Glu Arg
    50                  55                  60 ctt cat gat ggt gtg att cga aaa tcg ggc gat ccg tat att acc cac     240
Leu His Asp Gly Val Ile Arg Lys Ser Gly Asp Pro Tyr Ile Thr His
65                  70                  75                  80 ccg ttg gct gtc gcc acc atc gcc gcg gaa atc ggc atg gac acc acc     288
Pro Leu Ala Val Ala Thr Ile Ala Ala Glu Ile Gly Met Asp Thr Thr
                85                  90                  95 acg ctc gtc gca gcc ttg ttg cat gac acg gtg gaa gac acc gac tac     336
Thr Leu Val Ala Ala Leu Leu His Asp Thr Val Glu Asp Thr Asp Tyr
            100                 105                 110 tct ttg gac gat ctc acc cga gat ttc gga gaa gaa gtt gcc agg ctt     384
Ser Leu Asp Asp Leu Thr Arg Asp Phe Gly Glu Glu Val Ala Arg Leu
        115                 120                 125
```

-continued

| | |
|---|---|
| gtc gac ggt gtc acc aag ctc gac aaa gtc gca cta ggt gct gcc gcg<br>Val Asp Gly Val Thr Lys Leu Asp Lys Val Ala Leu Gly Ala Ala Ala<br>130                   135                   140 | 432 |
| gag gcc gaa acg att cgc aaa atg atc gtc gcc atg agc cag gac ccc<br>Glu Ala Glu Thr Ile Arg Lys Met Ile Val Ala Met Ser Gln Asp Pro<br>145                   150                   155                   160 | 480 |
| cgc gtg ctg gtg att aaa gtg gcc gac cgt ttg cac aat atg cgc acc<br>Arg Val Leu Val Ile Lys Val Ala Asp Arg Leu His Asn Met Arg Thr<br>                   165                   170                   175 | 528 |
| atg cgg ttc ctg ccg ccg gaa aag caa gct aaa aaa gca cgc caa acc<br>Met Arg Phe Leu Pro Pro Glu Lys Gln Ala Lys Lys Ala Arg Gln Thr<br>                   180                   185                   190 | 576 |
| ctt gaa gtg att gct cct ttg gca cac cgc ctg ggc atg gcc agc gtg<br>Leu Glu Val Ile Ala Pro Leu Ala His Arg Leu Gly Met Ala Ser Val<br>          195                   200                   205 | 624 |
| aaa tgg gaa ttg gaa gat cta tcc ttt gcc att ttg tac ccc aag aag<br>Lys Trp Glu Leu Glu Asp Leu Ser Phe Ala Ile Leu Tyr Pro Lys Lys<br>210                   215                   220 | 672 |
| tac gaa gag atc gtg cgt ctt gtt gcc gac cgc gcg ccc tct aga gac<br>Tyr Glu Glu Ile Val Arg Leu Val Ala Asp Arg Ala Pro Ser Arg Asp<br>225                   230                   235                   240 | 720 |
| cgg tac ctc aaa gaa att att gat caa gtc acc ggt ggc ttg cgc gaa<br>Arg Tyr Leu Lys Glu Ile Ile Asp Gln Val Thr Gly Gly Leu Arg Glu<br>                   245                   250                   255 | 768 |
| aac aac atc gcg gca gaa gtg ctt ggt cga cca aag cac tac tgg tct<br>Asn Asn Ile Ala Ala Glu Val Leu Gly Arg Pro Lys His Tyr Trp Ser<br>                   260                   265                   270 | 816 |
| atc tat caa aag atg atc gtt cgc ggt cgt gat ttt gac gat att ttt<br>Ile Tyr Gln Lys Met Ile Val Arg Gly Arg Asp Phe Asp Asp Ile Phe<br>          275                   280                   285 | 864 |
| gat ctt gtt ggc atc cgc atc ctg gta gac aac gtg aac aac tgt tac<br>Asp Leu Val Gly Ile Arg Ile Leu Val Asp Asn Val Asn Asn Cys Tyr<br>290                   295                   300 | 912 |
| gcc gcc atc ggt gtc gtg cac tcc ctg ttc aat gct ctg cct ggc cga<br>Ala Ala Ile Gly Val Val His Ser Leu Phe Asn Ala Leu Pro Gly Arg<br>305                   310                   315                   320 | 960 |
| ttc aaa gac tat att tca gcc ccg cgc ttc ggt gtc tac caa tcc ctg<br>Phe Lys Asp Tyr Ile Ser Ala Pro Arg Phe Gly Val Tyr Gln Ser Leu<br>                   325                   330                   335 | 1008 |
| cac acc acc gtg atg gga cct ggc ggt aag cct ctg gaa gtt cag gca<br>His Thr Thr Val Met Gly Pro Gly Gly Lys Pro Leu Glu Val Gln Ala<br>                   340                   345                   350 | 1056 |
| cgt acc cac gac atg cac tac aac gcc gaa ttc ggc att gca gcg cac<br>Arg Thr His Asp Met His Tyr Asn Ala Glu Phe Gly Ile Ala Ala His<br>          355                   360                   365 | 1104 |
| tgg cga tac aaa gaa acc aaa ggc agc cac agt ggc gag caa gcc gaa<br>Trp Arg Tyr Lys Glu Thr Lys Gly Ser His Ser Gly Glu Gln Ala Glu<br>370                   375                   380 | 1152 |
| gtg gat caa atg gcg tgg atg cgc caa ctt ctg gac tgg caa aaa gaa<br>Val Asp Gln Met Ala Trp Met Arg Gln Leu Leu Asp Trp Gln Lys Glu<br>385                   390                   395                   400 | 1200 |
| gca gcc gac ccc aac gag ttc ctg gac agc ctg cgc tac gat ctg act<br>Ala Ala Asp Pro Asn Glu Phe Leu Asp Ser Leu Arg Tyr Asp Leu Thr<br>                   405                   410                   415 | 1248 |
| tcc aag cag atc ttc gtg ttc aca ccc aaa ggt gat gtg gtc aac ctg<br>Ser Lys Gln Ile Phe Val Phe Thr Pro Lys Gly Asp Val Val Asn Leu<br>                   420                   425                   430 | 1296 |
| ccg gtg aac tcc acc ccg gtg gac ttc gcc tac gcg gtg cac acc gaa<br>Pro Val Asn Ser Thr Pro Val Asp Phe Ala Tyr Ala Val His Thr Glu<br>          435                   440                   445 | 1344 |

```
gtg ggg cac cgc tgc atc ggc gcc aaa atc aac ggc aaa ctg gtc gct    1392
Val Gly His Arg Cys Ile Gly Ala Lys Ile Asn Gly Lys Leu Val Ala
    450                 455                 460 ttg gaa acg aaa ctc aaa tcc ggc gat cgt gtt gaa gtc ttt acc tcc    1440
Leu Glu Thr Lys Leu Lys Ser Gly Asp Arg Val Glu Val Phe Thr Ser
465                 470                 475                 480 aag gac caa aac gct ggc cca agt agg gga tgg caa gaa ttt gtt gtc    1488
Lys Asp Gln Asn Ala Gly Pro Ser Arg Gly Trp Gln Glu Phe Val Val
                485                 490                 495 tca cct cgt gca aag gcc aag att cgc cag tgg ttt gcc aag gaa cga    1536
Ser Pro Arg Ala Lys Ala Lys Ile Arg Gln Trp Phe Ala Lys Glu Arg
            500                 505                 510 cgc gaa gaa tac cta gaa gcc gga cgc gat gcg ctg gca gca gtt att    1584
Arg Glu Glu Tyr Leu Glu Ala Gly Arg Asp Ala Leu Ala Ala Val Ile
        515                 520                 525 cag cgt ggc ggc ctg cca atg cac cgc ttg ttc acc gcg tcc tcc atg    1632
Gln Arg Gly Gly Leu Pro Met His Arg Leu Phe Thr Ala Ser Ser Met
    530                 535                 540 aag acg gtg gca aca gag ctg cac tac cca gat gta gat gcg ctc tac    1680
Lys Thr Val Ala Thr Glu Leu His Tyr Pro Asp Val Asp Ala Leu Tyr
545                 550                 555                 560 aca gcc atc ggc tcc ggt tct gta tct gcg caa cac gta gtc aac cgt    1728
Thr Ala Ile Gly Ser Gly Ser Val Ser Ala Gln His Val Val Asn Arg
                565                 570                 575 ctc atg gct atc ttt ggt gac gaa gaa gat gcc gaa gac gca ttg gtt    1776
Leu Met Ala Ile Phe Gly Asp Glu Glu Asp Ala Glu Asp Ala Leu Val
            580                 585                 590 gca cgc acc cca ttc agc gag ctg gtc aac tcc cgt gcc acc acg gaa    1824
Ala Arg Thr Pro Phe Ser Glu Leu Val Asn Ser Arg Ala Thr Thr Glu
        595                 600                 605 agc agc acc ggc atc ctg gtc gaa ggc agc cca gat gtc atg gct aag    1872
Ser Ser Thr Gly Ile Leu Val Glu Gly Ser Pro Asp Val Met Ala Lys
    610                 615                 620 ctc gct aaa tgc tgt atg cca gtg cca gga gat gaa atc ttt gga ttc    1920
Leu Ala Lys Cys Cys Met Pro Val Pro Gly Asp Glu Ile Phe Gly Phe
625                 630                 635                 640 gtc acc cgt ggt ggc ggt gtc tcc gta cac cga aca gac tgc acg aat    1968
Val Thr Arg Gly Gly Gly Val Ser Val His Arg Thr Asp Cys Thr Asn
                645                 650                 655 gtg gaa aag ctc aaa gaa gag cca gaa cgc att gtc tcc gtc tcc tgg    2016
Val Glu Lys Leu Lys Glu Glu Pro Glu Arg Ile Val Ser Val Ser Trp
            660                 665                 670 gct tcg gaa ggt caa ggt tca gta ttc tct gcc aca ctg cag ctt gaa    2064
Ala Ser Glu Gly Gln Gly Ser Val Phe Ser Ala Thr Leu Gln Leu Glu
        675                 680                 685 gca ctt gat cgc gca ggc ctg ctc ttt gag ctc acc cgc gta atc aac    2112
Ala Leu Asp Arg Ala Gly Leu Leu Phe Glu Leu Thr Arg Val Ile Asn
    690                 695                 700 gaa caa aag gtc tcc gtt acc gca atg aac tcc cat tgc tca gaa gac    2160
Glu Gln Lys Val Ser Val Thr Ala Met Asn Ser His Cys Ser Glu Asp
705                 710                 715                 720 cgc gta gcc acc gtg cgc ttc acc ttt gcg gtc tct gac acc aag cag    2208
Arg Val Ala Thr Val Arg Phe Thr Phe Ala Val Ser Asp Thr Lys Gln
                725                 730                 735 ttg gga tcc ctg atg aca cag ctg cgc aat gcc gaa gga gtg ttt gat    2256
Leu Gly Ser Leu Met Thr Gln Leu Arg Asn Ala Glu Gly Val Phe Asp
            740                 745                 750 gtc tac cga gtg acc tcg ggt ggc tag                                2283
Val Tyr Arg Val Thr Ser Gly Gly
        755                 760
```

<210> SEQ ID NO 22
<211> LENGTH: 760
<212> TYPE: PRT
<213> ORGANISM: Corynebacterium glutamicum

<400> SEQUENCE: 22
```
Met Ser Leu Glu Arg Asn Thr Gln Lys Ser Ser Met Gly Val Arg Ser
1               5                   10                  15

Met Ser Ala Arg Leu Ala Arg Ser Leu Thr Gly Asn Arg Val Arg Thr
            20                  25                  30

Asn Pro Val Leu Asp Pro Leu Leu Ser Ile His Arg Gln Phe His Pro
        35                  40                  45

Arg Ala Asp Val Gln Val Leu Glu Arg Ala Tyr Asp Thr Ala Glu Arg
    50                  55                  60

Leu His Asp Gly Val Ile Arg Lys Ser Gly Asp Pro Tyr Ile Thr His
65                  70                  75                  80

Pro Leu Ala Val Ala Thr Ile Ala Ala Glu Ile Gly Met Asp Thr Thr
                85                  90                  95

Thr Leu Val Ala Ala Leu Leu His Asp Thr Val Glu Asp Thr Asp Tyr
            100                 105                 110

Ser Leu Asp Asp Leu Thr Arg Asp Phe Gly Glu Glu Val Ala Arg Leu
        115                 120                 125

Val Asp Gly Val Thr Lys Leu Asp Lys Val Ala Leu Gly Ala Ala Ala
    130                 135                 140

Glu Ala Glu Thr Ile Arg Lys Met Ile Val Ala Met Ser Gln Asp Pro
145                 150                 155                 160

Arg Val Leu Val Ile Lys Val Ala Asp Arg Leu His Asn Met Arg Thr
                165                 170                 175

Met Arg Phe Leu Pro Pro Glu Lys Gln Ala Lys Lys Ala Arg Gln Thr
            180                 185                 190

Leu Glu Val Ile Ala Pro Leu Ala His Arg Leu Gly Met Ala Ser Val
        195                 200                 205

Lys Trp Glu Leu Glu Asp Leu Ser Phe Ala Ile Leu Tyr Pro Lys Lys
    210                 215                 220

Tyr Glu Glu Ile Val Arg Leu Val Ala Asp Arg Ala Pro Ser Arg Asp
225                 230                 235                 240

Arg Tyr Leu Lys Glu Ile Ile Asp Gln Val Thr Gly Gly Leu Arg Glu
                245                 250                 255

Asn Asn Ile Ala Ala Glu Val Leu Gly Arg Pro Lys His Tyr Trp Ser
            260                 265                 270

Ile Tyr Gln Lys Met Ile Val Arg Gly Arg Asp Phe Asp Asp Ile Phe
        275                 280                 285

Asp Leu Val Gly Ile Arg Ile Leu Val Asp Asn Val Asn Asn Cys Tyr
    290                 295                 300

Ala Ala Ile Gly Val Val His Ser Leu Phe Asn Ala Leu Pro Gly Arg
305                 310                 315                 320

Phe Lys Asp Tyr Ile Ser Ala Pro Arg Phe Gly Val Tyr Gln Ser Leu
                325                 330                 335

His Thr Thr Val Met Gly Pro Gly Gly Lys Pro Leu Glu Val Gln Ala
            340                 345                 350

Arg Thr His Asp Met His Tyr Asn Ala Glu Phe Gly Ile Ala Ala His
        355                 360                 365

Trp Arg Tyr Lys Glu Thr Lys Gly Ser His Ser Gly Glu Gln Ala Glu
    370                 375                 380
```

Val Asp Gln Met Ala Trp Met Arg Gln Leu Leu Asp Trp Gln Lys Glu
385                 390                 395                 400

Ala Ala Asp Pro Asn Glu Phe Leu Asp Ser Leu Arg Tyr Asp Leu Thr
            405                 410                 415

Ser Lys Gln Ile Phe Val Phe Thr Pro Lys Gly Asp Val Val Asn Leu
        420                 425                 430

Pro Val Asn Ser Thr Pro Val Asp Phe Ala Tyr Ala Val His Thr Glu
        435                 440                 445

Val Gly His Arg Cys Ile Gly Ala Lys Ile Asn Gly Lys Leu Val Ala
    450                 455                 460

Leu Glu Thr Lys Leu Lys Ser Gly Asp Arg Val Glu Val Phe Thr Ser
465                 470                 475                 480

Lys Asp Gln Asn Ala Gly Pro Ser Arg Gly Trp Gln Glu Phe Val Val
            485                 490                 495

Ser Pro Arg Ala Lys Ala Lys Ile Arg Gln Trp Phe Ala Lys Glu Arg
        500                 505                 510

Arg Glu Glu Tyr Leu Glu Ala Gly Arg Asp Ala Leu Ala Ala Val Ile
        515                 520                 525

Gln Arg Gly Gly Leu Pro Met His Arg Leu Phe Thr Ala Ser Ser Met
530                 535                 540

Lys Thr Val Ala Thr Glu Leu His Tyr Pro Asp Val Asp Ala Leu Tyr
545                 550                 555                 560

Thr Ala Ile Gly Ser Gly Ser Val Ser Ala Gln His Val Val Asn Arg
            565                 570                 575

Leu Met Ala Ile Phe Gly Asp Glu Glu Asp Ala Glu Asp Ala Leu Val
        580                 585                 590

Ala Arg Thr Pro Phe Ser Glu Leu Val Asn Ser Arg Ala Thr Thr Glu
        595                 600                 605

Ser Ser Thr Gly Ile Leu Val Glu Gly Ser Pro Asp Val Met Ala Lys
    610                 615                 620

Leu Ala Lys Cys Cys Met Pro Val Pro Gly Asp Glu Ile Phe Gly Phe
625                 630                 635                 640

Val Thr Arg Gly Gly Gly Val Ser Val His Arg Thr Asp Cys Thr Asn
            645                 650                 655

Val Glu Lys Leu Lys Glu Glu Pro Glu Arg Ile Val Ser Val Ser Trp
        660                 665                 670

Ala Ser Glu Gly Gln Gly Ser Val Phe Ser Ala Thr Leu Gln Leu Glu
        675                 680                 685

Ala Leu Asp Arg Ala Gly Leu Leu Phe Glu Leu Thr Arg Val Ile Asn
    690                 695                 700

Glu Gln Lys Val Ser Val Thr Ala Met Asn Ser His Cys Ser Glu Asp
705                 710                 715                 720

Arg Val Ala Thr Val Arg Phe Thr Phe Ala Val Ser Asp Thr Lys Gln
            725                 730                 735

Leu Gly Ser Leu Met Thr Gln Leu Arg Asn Ala Glu Gly Val Phe Asp
        740                 745                 750

Val Tyr Arg Val Thr Ser Gly Gly
        755                 760

<210> SEQ ID NO 23
<211> LENGTH: 20

-continued

```
<212> TYPE: DNA
<213> ORGANISM: Artificial sequence
<220> FEATURE:
<223> OTHER INFORMATION: Synthetic primer rel-2

<400> SEQUENCE: 23
ccgtcattgt ggtcagagat                                               20

<210> SEQ ID NO 24
<211> LENGTH: 5
<212> TYPE: PRT
<213> ORGANISM: Artificial sequence
<220> FEATURE:
<223> OTHER INFORMATION: A sequence motif of GTP-pyrophosphate kinase

<400> SEQUENCE: 24

Glu Pro Tyr Ile Thr
1               5

<210> SEQ ID NO 25
<211> LENGTH: 6
<212> TYPE: PRT
<213> ORGANISM: Artificial sequence
<220> FEATURE:
<223> OTHER INFORMATION: A sequence motif of GTP-pyrophosphate kinase

<400> SEQUENCE: 25

Ile His Pro Leu Ala Val
1               5

<210> SEQ ID NO 26
<211> LENGTH: 10
<212> TYPE: PRT
<213> ORGANISM: Artificial sequence
<220> FEATURE:
<223> OTHER INFORMATION: A sequence motif of GTP-pyrophosphate kinase

<400> SEQUENCE: 26

Gly Leu Leu His Asp Thr Val Glu Asp Thr
1               5                   10

<210> SEQ ID NO 27
<211> LENGTH: 16
<212> TYPE: PRT
<213> ORGANISM: Artificial sequence
<220> FEATURE:
<223> OTHER INFORMATION: A sequence motif of GTP-pyrophosphate kinase

<400> SEQUENCE: 27

Thr Pro Val Asp Phe Ala Tyr Ala Val His Thr Glu Val Gly His Arg
1               5                   10                  15
```

ALLELES OF THE REL GENE FROM CORYNEFORM BACTERIA

CROSS REFERENCE TO RELATED APPLICATIONS

This application is a divisional of U.S. patent application Ser. No. 11/873,073, filed Oct. 16, 2007, which is incorporated herein by reference.

BACKGROUND OF THE INVENTION

1. Field of the Invention

The invention relates to mutants and alleles of the rel gene of coryneform bacteria, which encode variants of GTP-pryophosphate kinase, and to processes for preparing amino acids, in particular L-lysine, L-tryptophan, L-proline, L-valine, L-isoleucine and L-homoserine, by using bacteria which harbor the alleles.

2. Discussion of the Background

All publications, patent applications, patents, and other references mentioned herein are incorporated by reference in their entirety. Further, the materials, methods, and examples are illustrative only and are not intended to be limiting, unless otherwise specified.

Amino acids are applied in human medicine, in the pharmaceutical industry, in the food industry and in animal nutrition.

Amino acids are known to be prepared by fermentation of strains of coryneform bacteria, in particular *Corynebacterium glutamicum*. Due to the great importance, continuous efforts are made to improve the production processes. The processes may be improved with respect to fermentation-related measures such as, for example, stirring and oxygen supply or the composition of the nutrient media, such as, for example, sugar concentration during the fermentation, or the working-up into product form, for example by means of ion exchange chromatography, or the intrinsic performance characteristics of the microorganism itself.

The performance characteristics of said microorganisms are improved by applying methods of mutagenesis, selection and mutant choice. This enables strains to be obtained which are resistant to antimetabolites or auxotrophic for metabolites which are of regulatory importance, and produce amino acids. A known antimetabolite is the lysine analog S-(2-aminoethyl)-L-cysteine (AEC).

For some years now, methods of recombinant DNA technology have likewise been employed in order to improve L-amino acid-producing *Corynebacterium* strains, by amplifying individual amino acid biosynthesis genes and studying the effect on amino acid production.

The *Corynebacterium glutamicum* chromosome was sequenced completely some time ago (Kalinowski et al., Journal of Biotechnology 104, 5-25 (2003)). The *Corynebacterium efficiens* chromosome has likewise been sequenced previously (Nishio et al., Genome Res. 13 (7), 1572-1579 (2003)).

Corresponding sequence information can be found in the public databases. Suitable databases are, for example, the database of the European Molecular Biologies Laboratories (EMBL, Heidelberg, Germany and Cambridge, UK), the database of the National Center for Biotechnology Information (NCBI, Bethesda, Md., USA), that of the Swiss Institute of Bioinformatics (Swissprot, Geneva, Switzerland), the protein Information Resource Database (PIR, Washington, D.C., USA) and the DNA Data Bank of Japan (DDBJ, 1111 Yata, Mishima, 411-8540, Japan).

Overviews on the genetics, the metabolism and the technical industrial importance of *Corynebacterium* can be found in the papers by Ikeda, by Pfefferle et al. and Mueller and Huebner in the book "Microbial Production of L-Amino Acids" (Advances in Biochemical Engineering 79, (2003), Springer Verlag, Berlin, Germany, Editor: T. Scheper), in the special edition "A New Era in *Corynebacterium glutamicum* Biotechnology" of the Journal of Biotechnology (Volume 104 (1-3), 2003, Editor: A. Pühler and T. Tauch), and in the "Handbook of *Corynebacterium glutamicum*" (Editors: L. Eggeling and M. Bott, CRC Press, Taylor & Francis Group, Boca Raton, Fla., USA, 2005).

The nucleotide sequence of the rel gene coding for GTP-pyrophosphate kinase of *Corynebacterium glutamicum* is accessible, inter alia in the database of the National Center for Biotechnology Information (NCBI) of the National Library of Medicine (Bethesda, Md., USA) under the access number AF038651. It can furthermore be found as sequence no. 1824 in the patent application EP 1 108 790.

Wehmeier et al. (Microbiology 144, 1853-1862 (1998)) report, inter alia, genetic, microbiological and biochemical studies on a mutant of *Corynebacterium glutamicum* ATCC 13032 which carries a deletion in the rel gene.

For reasons of better clarity, SEQ ID NO:1 depicts the nucleotide sequence of the rel gene coding for GTP-pyrophosphate kinase of the wild type of *Corynebacterium glutamicum* ("wild type gene"), according to the information of the NCBI database, and SEQ ID NO:2 or 4 depict the amino acid sequence derived therefrom of the encoded GTP-pyrophosphate kinase. In addition, SEQ ID NO:3 indicates nucleotide sequences located upstream and downstream. The amino acid sequence according to SEQ ID NO: 2 and 4 comprises glycine in position 262. The amino acid sequence of wildtype GTP-pyrophosphate kinase, disclosed in EP 1 108 790 comprises L-glutamic acid in position 262. The nucleotide sequence of the wildtype rel gene according to EP 1 108 790 is depicted in sequence SEQ ID NO:21. SEQ ID NO:22 represents the encoded amino acid sequence.

SUMMARY OF THE INVENTION

It was an object of the present invention to provide novel measures for improving the production of amino acids, in particular L-lysine, L-tryptophan, L-proline, L-valine, L-isoleucine and L-homoserine.

This and other objects have been achieved by the present invention the first embodiment of which includes an isolated mutant of a coryneform bacterium comprising a gene coding for a polypeptide having GTP-pyrophosphate kinase activity, wherein said polypeptide comprises an amino acid sequence in which one of the proteinogenic amino acids other than L-proline is present in position 38 or a corresponding or comparable position.

The invention further provides an isolated polynucleotide encoding a polypeptide having GTP-pyrophosphate kinase enzyme activity, a vector comprising the isolated polynucleotide, a recombinant microorganism comprising the vector, and a process for preparing the recombinant coryneform bacterium is described.

The invention also provides a method for over-expressing a GTP-pyrophosphate kinase, a method of preparing an L-amino acid, an L-lysine-comprising and L-tryptophan-comprising feed is also described.

BRIEF DESCRIPTION OF THE DRAWINGS

The FIGURE represents a map of the plasmid pK18moBsacB_rel_P38L.

DESCRIPTION OF THE INVENTION

The invention relates to generated or isolated mutants of coryneform bacteria which preferably secrete amino acids, and which comprise a gene or allele encoding a polypeptide having GTP-pyrophosphate kinase activity, wherein said polypeptide comprises an amino acid sequence in which one of the proteinogenic amino acids other than L-proline is present in position 38 or a corresponding or comparable position of the amino acid sequence, preferably, L-proline is substituted with L-leucine.

Among the coryneform bacteria, preference is given to the genus *Corynebacterium*. Among the genus *Corynebacterium*, preference is given to the following species:
  *Corynebacterium efficiens* (strain type DSM44549),
  *Corynebacterium glutamicum* (strain type ATCC13032),
  *Corynebacterium thermoaminogenes* (for example the strain FERM BP-1539), and
  *Corynebacterium ammoniagenes* (strain type ATCC6871), more preferably, to the species *Corynebacterium glutamicum*.

Some representatives of the species *Corynebacterium glutamicum* are also known under different species names in the prior art. These include, for example:
  *Corynebacterium acetoacidophilum* ATCC13870,
  *Corynebacterium lilium* DSM20137,
  *Corynebacterium melassecola* ATCC17965,
  *Brevibacterium flavum* ATCC14067,
  *Brevibacterium lactofermentum* ATCC13869,
  *Brevibacterium divaricatum* ATCC14020, and
  *Microbacterium ammoniaphilum* ATCC15354.

The term "*Micrococcus glutamicus*" has also been used for *Corynebacterium glutamicum*.

The strains of coryneform bacteria employed for the purposes of the invention preferably already have the ability to concentrate the desired amino acid in the cell or to secrete and accumulate it in the surrounding nutrient medium. This is also referred to by the term "to produce" hereinbelow. Specifically, the strains of coryneform bacteria employed have the ability to concentrate or accumulate=(at least) 0.25 g/l, =0.5 g/l, =1.0 g/l, =1.5 g/l, =2.0 g/l, =4 g/l or =10 g/l of the desired amino acid in the cell or in the nutrient medium within=(no more than) 120 hours, =96 hours, =48 hours, =36 hours, =24 hours or =12 hours. The strains may be those which have been prepared by mutagenesis and selection, by recombinant DNA techniques or by a combination of both methods.

Examples of known representatives of L-lysine-producing or -secreting strains of coryneform bacteria are:
  *Corynebacterium glutamicum* DM58-1/pDM6 (=DSM4697) described in EP 0 358 940,
  *Corynebacterium glutamicum* MH20-22B (=DSM16835) described in Menkel et al. (Applied and Environmental Microbiology 55(3), 684-688 (1989)),
  *Corynebacterium glutamicum* AHP-3 (=Ferm BP-7382) described in EP 1 108 790,
  *Corynebacterium glutamicum* NRRL B-11474 described in U.S. Pat. No. 4,275,157, and
  *Corynebacterium thermoaminogenes* AJ12521 (=FERM BP-3304) described in U.S. Pat. No. 5,250,423.

Examples of known representatives of L-tryptophan-producing or -secreting strains of coryneform bacteria are:
  *Corynebacterium glutamicum* K76 (=Ferm BP-1847) described in U.S. Pat. No. 5,563,052,
  *Corynebacterium glutamicum* BPS13 (=Ferm BP-1777) described in U.S. Pat. No. 5,605,818, and
  *Corynebacterium glutamicum* Ferm BP-3055 described in U.S. Pat. No. 5,235,940.

Examples of known representatives of L-proline-producing or -secreting strains of coryneform bacteria are:
  *Brevibacterium lactofermentum* NRRL B-11421 described in U.S. Pat. No. 4,224,409,
  *Brevibacterium flavum* NRRL B-11422 described in U.S. Pat. No. 4,224,409,
  *Brevibacterium flavum* FERM BP-2214 described in U.S. Pat. No. 5,294,547,
  *Corynebacterium glutamicum* NRRL B-11423 described in U.S. Pat. No. 4,224,409,
  *Corynebacterium glutamicum* ATCC 21157 described in U.S. Pat. No. 4,444,885,
  *Corynebacterium glutamicum* ATCC 21158 described in U.S. Pat. No. 4,444,885,
  *Corynebacterium glutamicum* ATCC 21159 described in U.S. Pat. No. 4,444,885,
  *Corynebacterium glutamicum* ATCC 21355 described in U.S. Pat. No. 4,444,885, and
  *Macrobacterium ammoniaphilum* NRRL B-11424 described in U.S. Pat. No. 4,224,409.

Examples of known representatives of L-valine-producing or -secreting strains of coryneform bacteria are:
  *Brevibacterium lactofermentum* FERM BP-1763 described in U.S. Pat. No. 5,188,948,
  *Brevibacterium lactofermentum* FERM BP-3007 described in U.S. Pat. No. 5,521,074,
  *Corynebacterium glutamicum* FERM BP-3006 described in U.S. Pat. No. 5,521,074, and
  *Corynebacterium glutamicum* FERM BP-1764 described in U.S. Pat. No. 5,188,948.

Examples of known representatives of L-isoleucine-producing or -secreting strains of coryneform bacteria are:
  *Brevibacterium flavum* FERM BP-760 described in U.S. Pat. No. 4,656,135,
  *Brevibacterium flavum* FERM BP-2215 described in U.S. Pat. No. 5,294,547, and
  *Corynebacterium glutamicum* FERM BP-758 described in U.S. Pat. No. 4,656,135.

Examples of known representatives of L-homoserine-producing or -secreting strains of coryneform bacteria are:
  *Micrococcus glutamicus* ATCC 14296 described in U.S. Pat. No. 3,189,526 and
  *Micrococcus glutamicus* ATCC 14297 described in U.S. Pat. No. 3,189,526.

Information on the taxonomic classification of strains of this group of bacteria can be found, inter alia, in Seiler (Journal of General Microbiology 129, 1433-1477 (1983)), Kinoshita (1985, Glutamic Acid Bacteria, p115-142. In: Demain and Solomon (ed), Biology of Industrial Microorganisms. The Benjamin/Cummins Publishing Co., London, UK), Kämpfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains denoted "ATCC" may be obtained from the American Type Culture Collection (Manassas, Va., USA). Strains denoted "DSM" may be obtained from the Deutsche Sammlung von Mikroorganismen and Zellkulturen (DSMZ, Brunswick, Germany). Strains denoted "NRRL" may be obtained from the Agricultural Research Service patent Culture Collection (ARS, Peoria, Ill., US). Strains denoted "FERM" may be obtained from the National Institute of Advanced Industrial Science and Technology (AIST Tsukuba Central 6, 1-1-1 Higashi, Tsukuba Ibaraki, Japan).

A gene is chemically a polynucleotide. Another term for this is nucleic acid. The polypeptide with GTP-pyrophosphate kinase activity, encoded by the rel gene, is also referred to in the prior art as "GTP diphosphokinase", "guanosine 3',5'-polyphosphate synthase" or "stringent factor" (see, for example, KEGG database (Kyoto Encyclopedia of Genes and Genomes) of Kanehisa Laboratory, Bioinformatics Center, Institute for Chemical Research, Kyoto University, Japan).

Its EC number is 2.7.6.5. according to the IUPAC (International Union of Pure and Applied Chemistry) nomenclature.

It catalyzes the following reaction:

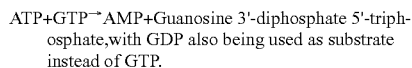
ATP+GTP→AMP+Guanosine 3'-diphosphate 5'-triphosphate, with GDP also being used as substrate instead of GTP.

The term "proteinogenic amino acids" means the amino acids occurring in natural proteins, i.e. in proteins of microorganisms, plants, animals and humans. However, in the context of the present invention, the term "proteinogenic amino acids" means the group of L-amino acids consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine. L-Amino acids also include L-homoserine.

The mutants of the invention preferably secrete said proteinogenic amino acids, more preferably L-lysine, L-tryptophan, L-proline, L-valine, L-isoleucine or L-homoserine. The term "amino acids" also comprises their salts such as, for example, lysine monohydrochloride or lysine sulfate in the case of the amino acid L-lysine.

The invention further relates to mutants of coryneform bacteria, which comprise a rel allele encoding a polypeptide having a GTP-pyrophosphate kinase enzyme activity, which polypeptide comprises the amino acid sequence of SEQ ID NO: 2, with one of the aforementioned proteinogenic amino acids other than L-proline being present in position 38, preferably L-proline is replaced with L-leucine.

The invention furthermore relates to mutants of coryneform bacteria, which comprise a rel allele encoding a polypeptide having GTP-pyrophosphate kinase enzyme activity, which polypeptide comprises one of the proteinogenic amino acids other than L-proline, preferably, L-leucine, in the position corresponding to position 38 of the amino acid sequence of SEQ ID NO:2, the gene comprising a nucleotide sequence identical to the nucleotide sequence of a polynucleotide which is obtainable by a polymerase chain reaction (PCR) using a primer pair whose nucleotide sequences comprise in each case at least 15 contiguous nucleotides selected from the nucleotide sequence between positions 1 and 750 of SEQ ID NO:3 or SEQ ID NO:7 and from the complementary nucleotide sequence between positions 3800 and 3031 of SEQ ID NO:3 or SEQ ID NO:7. One example of a suitable primer pair is depicted in SEQ ID NO:19 and SEQ ID NO:20. The preferred starting material (template DNA) is chromosomal DNA of coryneform bacteria which have been treated in particular with a mutagen, preferably, the chromosomal DNA of the genus *Corynebacterium*, and more preferably, the species *Corynebacterium glutamicum*.

The invention furthermore relates to mutants of coryneform bacteria, which comprise a rel allele encoding a polypeptide having GTP-pyrophosphate kinase enzyme activity, which polypeptide comprises an amino acid sequence having a length corresponding to 760 L-amino acids, with one of the proteinogenic amino acids other than L-proline, preferably L-leucine, being present in position 38.

The invention furthermore relates to mutants of coryneform bacteria, which comprise a rel allele encoding a polypeptide having GTP-pyrophosphate kinase enzyme activity, which polypeptide comprises the amino acid sequence corresponding to positions 19 to 57 of SEQ ID NO:6 or 8 in positions 19 to 57 of the amino acid sequence. Preferably, the amino acid sequence of the encoded polypeptide comprises an amino acid sequence corresponding to positions 9 to 107 of SEQ ID NO:6 or 8 or to positions 9 to 207 of SEQ ID NO:6 or 8 or to positions 9 to 407 of SEQ ID NO:6 or 8 or to positions 9 to 607 of SEQ ID NO:6 or 8 or to positions 9 to 707 of SEQ ID NO:6 or 8 or to positions 2 to 707 of SEQ ID NO:6 or 8 or to positions 9 to 757 of SEQ ID NO:6 or 8 or to positions 2 to 757 of SEQ ID NO:6 or 8 or to positions 2 to 758 of SEQ ID NO:6 or 8 or to positions 2 to 759 of SEQ ID NO:6 or 8, L-glutamic acid being optionally present in position 262, preferably the encoded polypeptide comprises 760 amino acids.

The invention furthermore relates to mutants of coryneform bacteria, which comprise a rel allele encoding a polypeptide having GTP-pyrophosphate kinase enzyme activity, which polypeptide comprises one of the proteinogenic amino acids other than L-proline in position 38 or in the corresponding position of the amino acid sequence, preference being given to the substitution with L-leucine, and whose amino acid sequence is moreover at least 90%, preferably at least 92% or at least 94% or at least 96%, and more preferably at least 97% or at least 98% or at least 99%, identical to the amino acid sequence of SEQ ID NO:6 or SEQ ID NO:8. L-Glutamic acid is optionally contained in position 262 of SEQ ID NO:6 or SEQ ID NO:8.

The invention furthermore relates to mutants of coryneform bacteria, which comprise a rel allele encoding a polypeptide having GTP-pyrophosphate kinase enzyme activity, which polypeptide comprises one of the proteinogenic amino acids other than L-proline in position 38 or in the corresponding position of the amino acid sequence, with preference being given to the substitution with L-leucine, and whose nucleotide sequence is moreover at least 90%, preferably at least 92% or at least 94% or at least 96%, and more preferably at least 97% or at least 98% or at least 99%, identical to the nucleotide sequence of SEQ ID NO:5. Adenine is optionally present in position 785.

Conservative amino acid substitutions are known to alter the enzyme activity only insignificantly. Accordingly, the rel allele which is present in the mutants of the invention and which encodes a polypeptide having GTP-pyrophosphate kinase enzyme activity may comprise one (1) or more conservative amino acid substitution(s), in addition to the amino acid sequence depicted in SEQ ID NO:6 and SEQ ID NO:8, preferably, the polypeptide comprising no more than two (2), no more than three (3), no more than four (4) or no more than five (5), conservative amino acid substitutions. L-Glutamic acid is optionally present in position 262 of SEQ ID NO:6 or SEQ ID NO:8.

In the case of the aromatic amino acids, the substitutions are said to be conservative when phenylalanine, tryptophan and tyrosine are substituted for one another. In the case of the hydrophobic amino acids, the substitutions are said to be conservative when leucine, isoleucine and valine are substituted for one another. In the case of the polar amino acids, the substitutions are said to be conservative when glutamine and asparagine are substituted for one another. In the case of the basic amino acids, the substitutions are said to be conservative when arginine, lysine and histidine are substituted for one another. In the case of the acidic amino acids, the substitutions are said to be conservative when aspartic acid and glutamic acid are substituted for one another. In the case of the hydroxyl group-containing amino acids, the substitutions are said to be conservative when serine and threonine are substituted for one another.

During work on the present invention, comparison of the amino acid sequence using the Clustal program (Thompson et al., Nucleic Acids Research 22, 4637-4680 (1994)) revealed that the amino acid sequences of GTP-pyrophosphate kinase of various bacteria such as, for example, *Escherichia coli, Bacillus subtilis, Mycobacterium tuberculosis, Mycobacterium bovis, Streptomyces coeliclor, Streptomyces avermitilis, Corynebacterium efficiens* and *Corynebacterium glutamicum*, comprise a sequence motif consisting of the sequence Ser-Gly-Asp/Glu-Pro-Tyr-Ile-Thr/Ile-His-Pro-Leu-Ala-Val, a sequence motif consisting of the sequence Ala-Ala/Gly-Leu-Leu-His-Asp-Thr-Val-Glu-Asp-Thr, and also a sequence motif consisting of the sequence Thr-Pro-Val-Asp-Phe-Ala-Tyr-Ala-Val-His-Thr-Glu-Val-Gly-His-Arg. The terms "Asp/Glu", "Thr/Ile" and "Ala/Gly" mean that "Asp or Glu" or "Thr or Ile" or "Ala or Gly" are present in the corresponding position.

Accordingly, those mutants of coryneform bacteria, which comprise a rel allele encoding a polypeptide having GTP-pyrophosphate kinase enzyme activity, which polypeptide comprises at least one amino acid sequence selected from the group consisting of Ser-Gly-Asp/Glu-Pro-Tyr-Ile-Thr/Ile-His-Pro-Leu-Ala-Val, Ala-Ala/Gly-Leu-Leu-His-Asp-Thr-Val-Glu-Asp-Thr and Thr-Pro-Val-Asp-Phe-Ala-Tyr-Ala-Val-His-Thr-Glu-Val-Gly-His-Arg and which comprises one of the proteinogenic amino acids other than L-proline, preferably L-leucine, in position 38 or in the corresponding or comparable position of the amino acid sequence are preferred.

The amino acid sequence motif Ser-Gly-Asp/Glu-Pro-Tyr-Ile-Thr (SEQ ID NO:24)/Ile-His-Pro-Leu-Ala-Val (SEQ ID NO:25) is present, for example, in SEQ ID NO:2 or 4, respectively, or 6 or 8, respectively, from positions 73 to 84. The amino acid sequence motif Ala-Ala/Gly-Leu-Leu-His-Asp-Thr-Val-Glu-Asp-Thr (SEQ ID NO:26) is present, for example, in SEQ ID NO:2 or 4, respectively, or 6 or 8, respectively, from position 100 to 110. The amino acid sequence motif Thr-Pro-Val-Asp-Phe-Ala-Tyr-Ala-Val-His-Thr-Glu-Val-Gly-His-Arg (SEQ ID NO:27) is present, for example, in SEQ ID NO:2 or 4, respectively, or 6 or 8, respectively, from positions 437 to 452.

The invention relates to mutants of coryneform bacteria, which comprise a rel allele encoding a polypeptide having GTP-pyrophosphate kinase enzyme activity, which polypeptide comprises the amino acid sequence of SEQ ID NO:6 or SEQ ID NO:8, respectively, L-glutamic acid being optionally present in position 262.

Enzymes intrinsic to the host, called aminopeptidases, are known to remove the terminal methionine during protein synthesis.

The term "a position corresponding to position 38 of the amino acid sequence" or "a position comparable to position 38 of the amino acid sequence" means that an insertion or deletion of a codon coding for an amino acid in the N-terminal region (based on position 38 of SEQ ID NO:6 or 8) of the encoded polypeptide formally increases, in the case of an insertion, or decreases, in the case of a deletion, the indicated position and indicated length, in each case by one unit. For example, deletion of the GAG codon coding for the amino acid L-glutamic acid in position 4 of SEQ ID NO:6 or 8 moves the L-leucine from position 38 to position 37. The indicated length would then be: 759 amino acids. In the same way, insertion or deletion of a codon coding for an amino acid in the C-terminal region (based on position 38) of the encoded polypeptide formally increases, in the case of an insertion, or decreases, in the case of a deletion, the indicated length by one unit. Such comparable positions can readily be identified by comparing the amino acid sequences in the form of an alignment, for example, with the aid of the Clustal program or the MAFFT program.

Insertions and deletions of this kind essentially do not affect the enzymic activity. "Essentially do not affect" means that the enzymic activity of the variants mentioned differs from the activity of the polypeptide having the amino acid sequence of SEQ ID NO:6 or 8, respectively, by no more than 10%, no more than 7.5%, no more than 5%, no more than 2.5% or no more than 1%, L-glutamic acid being optionally present in position 262.

Accordingly, the invention also relates to rel alleles encoding polypeptide variants of SEQ ID NO:6 or 8, respectively, which variants comprise one or more insertion(s) or deletion(s), L-glutamic acid being optionally present in position 262. The polypeptide preferably comprises no more than 5, no more than 4, no more than 3 or no more than 2 amino acid insertions or deletions.

The abovementioned sequence motifs Ser-Gly-Asp/Glu-Pro-Tyr-Ile-Thr (SEQ ID NO:24)/Ile-His-Pro-Leu-Ala-Val (SEQ ID NO:25), Ala-Ala/Gly-Leu-Leu-His-Asp-Thr-Val-Glu-Asp-Thr (SEQ ID NO:26) and Thr-Pro-Val-Asp-Phe-Ala-Tyr-Ala-Val-His-Thr-Glu-Val-Gly-His-Arg (SEQ ID NO:27) are preferably not disrupted by such insertions/deletions.

The mutants of the invention may be prepared by classical in-vivo mutagenesis methods with cell populations of coryneform bacteria by using mutagenic substances such as, for example, N-methyl-N'-nitro-N-nitrosoguanidine (MNNG), ethyl methanesulfonate (EMS), 5-bromouracil, or ultraviolet light. Mutagenesis methods are described, for example, in Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)). Typical mutageneses using MNNG comprise concentrations of from 50 to 500 mg/l or else higher concentrations of up to a maximum of 1 g/l, an incubation time of from 1 to 30 minutes at a pH of from 5.5 to 7.5. Under these conditions, the number of viable cells is reduced by a proportion of from approx. 50% to 90% or approx. 50% to 99% or approx. 50% to 99.9% or more.

Mutants or cells are removed from the mutagenized cell population and propagated. In a further step, the ability of the mutants or cells to secrete amino acids, preferably L-lysine, L-tryptophan, L-proline, L-valine, L-isoleucine or L-homoserine in a batch culture using a suitable nutrient medium is investigated. Suitable nutrient media and assay conditions are described, inter alia, in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409. When suitable robots are used, such as, for example, in Zimmermann et al. (VDI Berichte No. 1841, VDI-Verlag, Dusseldorf, Germany 2004, 439-443) or Zimmermann (Chemie Ingenenieur Technik 77 (4), 426-428 (2005)), it is possible to study numerous mutants within a short period of time. Usually no more than 3000, no more than 10 000, no more than 30 000 or else no more than 60 000, where appropriate also more, mutants are studied. In this way, mutants are identified which, compared to the parent strain or non-mutagenized starting strain, secrete an increased amount of amino acids into the nutrient medium or the cell interior. These include, for example, those mutants whose amino acid secretion has increased by at least 0.5%.

Subsequently, DNA of the mutants is provided or isolated from the latter and the corresponding polynucleotide is synthesized with the aid of the polymerase chain reaction using primer pairs which allow amplification of the rel gene or of the rel allele of the invention or of the mutation of the invention in position 38. Preferably, the DNA from those mutants which secrete an increased amount of amino acids is isolated.

It is possible to select any primer pairs from the nucleotide sequence located upstream and downstream of the mutation of the invention and from the nucleotide sequence complementary thereto. A primer of a primer pair here preferably comprises at least 15, at least 18, at least 20, at least 21 or at least 24, contiguous nucleotides selected from the nucleotide sequence between positions 1 and 861 of SEQ ID NO:3 or SEQ ID NO:7. The corresponding second primer of a primer pair comprises at least 15, at least 18, at least 20, at least 21 or at least 24, contiguous nucleotides selected from the complementary nucleotide sequence of positions 3800 and 865 of SEQ ID NO:3 or SEQ ID NO:7. If it is desired to amplify the coding region, then the primer pair is preferably selected from the nucleotide sequence between positions 1 and 750 of SEQ ID NO:3 or SEQ ID NO:7 and from the complementary nucleotide sequence between positions 3800 and 3031 of SEQ ID NO:3 or SEQ ID NO:7.

If it is desired to amplify part of the coding region, as indicated, for example, in SEQ ID NO:11 and 13, then the primer pair is preferably selected from the nucleotide sequence between positions 751 and 804 or between positions 1 and 804 of SEQ ID NO:3 or SEQ ID NO:7 and from the complementary nucleotide sequence between positions 3030 and 922 or 3800 and 922 of SEQ ID NO:3 or SEQ ID NO:7. An example of a suitable primer pair is the rel_XL_A1 and rel_X_E1 primer pair depicted under SEQ ID NO:19 and SEQ ID NO:20. In addition, the primer may be provided with recognition sites for restriction enzymes, with a biotin group or further accessories as described in the prior art. The total length of the primer is no more than 30, 40, 50 or 60 nucleotides.

Thermostable DNA polymerases are employed in the preparation of polynucleotides by amplification of selected sequences such as the rel allele of the invention from initially introduced DNA, for example chromosomal DNA (template DNA), via amplification by means of PCR. Examples of DNA polymerases of this kind are Taq polymerase of *Thermus aquaticus*, which is sold, inter alia, by Qiagen (Hilden, Germany), Vent polymerase of *Thermococcus litoralis*, sold, inter alia, by New England Biolabs (Frankfurt, Germany), or Pfu polymerase of *Pyrococcus furiosus*, sold, inter alia, by Stratagene (La Jolla, USA). Preference is given to polymerases having proof-reading activity. Proof-reading activity means that these polymerases are capable of recognizing wrongly incorporated nucleotides and rectifying the error by renewed polymerization (Lottspeich and Zorbas, Bioanalytik, Spektrum Akademischer Verlag, Heidelberg, Germany (1998)). Examples of polymerases having proof-reading activity are Vent polymerase and Pfu polymerase.

The conditions in the reaction mixture are set according to the information provided by the manufacturer. The polymerases are usually supplied by the manufacturer together with the customary buffer which usually has concentrations of 10-100 mM Tris/HCl and 6-55 mM KCl at pH 7.5-9.3. Magnesium chloride is added in a concentration of 0.5-10 mM, if not present in the buffer supplied by the manufacturer. Furthermore, deoxynucleoside triphosphates are added in a concentration of 0.1-16.6 mM to the reaction mixture. The primers, in a final concentration of 0.1-3 µM, and template DNA, in the optimal case from $10^2$ to $10^5$ copies, are initially introduced into the reaction mixture. $10^6$ to $10^7$ copies may also be used. An amount of 2-5 units of the appropriate polymerase is added to the reaction mixture. A typical reaction mixture has a volume of 20-100 µl.

Further additives which may be added to the reaction are bovine serum albumin, Tween-20, gelatin, glycerol, formamide or DMSO (Dieffenbach and Dveksler, PCR Primer—A Laboratory Manual, Cold Spring Harbor Laboratory Press, USA 1995).

A typical PCR profile consists of three different, successively repeated temperature stages. Initially, the reaction is started by increasing the temperature to 92° C.-98° C. for 4 to 10 minutes in order to denature the initially introduced DNA. This is followed repeatedly by first a step of denaturing the initially introduced DNA at approximately 92-98° C. for 10-60 seconds, then a step of 10-60 seconds of binding the primers to the initially introduced DNA at a particular temperature dependent on said primers (annealing temperature), which from experience is from 50° C. to 60° C. and can be calculated for each primer pair individually. Detailed information on this can be found by the skilled worker in Rychlik et al. (Nucleic Acids Research 18 (21): 6409-6412). Subsequently, a synthesis step of extending the initially introduced primers (extension) at the activity optimum of the polymerase, indicated in each case and usually in the range from 73° C. to 67° C., preferably 72° C. to 68° C., depending on the polymerase. The duration of this extension step depends on the performance of the polymerase and on the length of the PCR product to be amplified. In a typical PCR, this step lasts 0.5-8 minutes, preferably 2-4 minutes. These three steps are repeated 30 to 35 times, where appropriate up to 50 times. A final "extension" step of 4-10 minutes ends the reaction. The polynucleotides prepared in this manner are also referred to as amplicons; the term nucleic acid fragment is likewise common.

Further instructions and information regarding PCR can be found by the skilled worker, for example, in the manual "PCR-Strategies" (Innis, Felfand and Sninsky, Academic Press, Inc., 1995), in the manual by Diefenbach and Dveksler "PCR Primer—a laboratory manual" (Cold Spring Harbor Laboratory Press, 1995), in the manual by Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is subsequently determined, for example by the chain termination method of Sanger et al. (Proceedings of the National Academies of Sciences, U.S.A., 74, 5463-5467 (1977)) with the modifications indicated by Zimmermann et al. (Nucleic Acids Research 18, 1067pp (1990)), and the polypeptide encoded by said nucleotide sequence is analyzed, in particular with respect to the amino acid sequence. For this purpose, the nucleotide sequence is entered into a program for translating DNA sequence into an amino acid sequence. Examples of suitable programs are the program "Patentin" which is available from patent offices, for example the US Patent and Trademark Office (USPTO), or "Translate Tool" which is available on the ExPASy Proteomics Server on the World Wide Web (Gasteiger et al., Nucleic Acids Research 31, 3784-3788 (2003)).

In this way, mutants are identified whose rel alleles encode polypeptides having GTP-pyrophosphate kinase enzyme activity, which polypeptides comprise one of the proteinogenic amino acids other than L-proline in position 38 of the amino acid sequence or in the corresponding or comparable position, preferably, the substitution with L-leucine.

Where appropriate, the entire chromosome of the mutant is determined. This may involve using the method described by margulies et al. (Nature, 437(7057): 376-380 (2005) and Velicer et al. (Proceedings of the National Academy of Sciences, USA., 103(21), 8107-8112 (2006)), which is known under the keyword "pyro-sequencing" in the art and enables complete genomes to be sequenced rapidly.

Accordingly, the invention relates to a mutant of a coryneform bacterium, which is obtainable by a method comprising:
a) treating a coryneform bacterium capable of secreting amino acids with a mutagenic agent,
b) isolating and propagating the mutant generated in a),
c) preferably determining the ability of said mutant to secrete in a medium or to accumulate in the cell interior at least 0.5% more amino acid than the coryneform bacterium employed in a),
d) providing nucleic acid of the mutant obtained in b),
e) preparing a nucleic acid molecule (amplicon or nucleic acid fragment, respectively) using the polymerase chain reaction, of the nucleic acid from d) and of a primer pair consisting of a first primer comprising at least 15 contiguous nucleotides selected from the nucleotide sequence between positions 1 and 861, preferably 1, and 750 of SEQ ID NO:3 or SEQ ID NO:7 and a second primer comprising at least 15 contiguous nucleotides selected from the complementary nucleotide sequence between positions 3800 and 865, preferably 3800, and 3031 of SEQ ID NO:3 or 7,
f) determining the nucleotide sequence of the nucleic acid molecule obtained in e) and determining the encoded amino acid sequence,
g) comparing, where appropriate, the amino acid sequence determined in f) with SEQ ID NO:6 or 8 L-glutamic acid being optionally present in position 262, and
h) identifying a mutant comprising a polynucleotide which encodes a polypeptide comprising one of the proteinogenic amino acids other than L-proline, preferably L-leucine, in position 38 or a comparable position.

The mutants generated in this way typically comprise one (1) copy of the rel allele described.

SEQ ID NO:5 depicts, by way of example, the coding region of rel allele of a mutant of the invention. The coding region of the wild type gene is depicted as SEQ ID NO:1. SEQ ID NO:1 comprises the nucleobase cytosine in position 112, the nucleobase cytosine in position 113 and the nucleobase guanine in position 114. SEQ ID NO:1 thus comprises the CCG codon, coding for the amino acid L-proline, from positions 112 to 114. SEQ ID NO:5 comprises the nucleobase thymine in position 113. This cytosine-thymine transition results in the CTG codon, coding for the amino acid L-leucine, in positions 112 to 114.

In addition, the nucleotide sequences depicted in SEQ ID NO: 5 and 7, respectively, may comprise further base substitutions which have resulted from the mutagenesis treatment but which do not manifest themselves in an altered amino acid sequence. Such mutations are referred to in the art also as silent or neutral mutations. These silent mutations may likewise already be present in the coryneform bacterium used for the mutagenesis treatment.

The coryneform bacteria used for the mutagenesis preferably already have the ability to secrete the desired amino acid into the surrounding nutrient medium or fermentation broth or to accumulate it in the cell interior.

L-Lysine-producing coryneform bacteria typically possess a feedback-resistant or desensibilized aspartate kinase. Feedback-resistant aspartate kinases mean aspartate kinases (LysC) which, compared to the wild type, have a lower sensitivity to the inhibition by mixtures of lysine and threonine or mixtures of AEC (aminoethylcysteine) and threonine or lysine alone or AEC alone. The genes or alleles encoding these desensibilized aspartate kinases are also referred to as $lysC^{FBR}$ alleles. The prior art describes numerous $lysC^{FBR}$ alleles encoding aspartate kinase variants which have amino acid substitutions in comparison with the wild type protein. SEQ ID NO:9 depicts the coding region of the wild type lysC gene of *Corynebacterium glutamicum* according to accession number AX756575 of the NCBI database, and SEQ ID NO:10 depicts the polypeptide encoded by said gene.

The L-lysine-producing coryneform bacteria employed for the purposes of the invention have preferably an lysC allele encoding an aspartate kinase variant whose amino acid sequence is that of SEQ ID NO:10 comprising one or more of the amino acid substitutions selected from the group consisting of:

LysC A279T (replacing L-alanine in position 279 of the encoded aspartate kinase protein according to sequence SEQ ID NO:10 with L-threonine; see U.S. Pat. No. 5,688,671 and Accession numbers E06825, E06826, E08178 and I74588 to I74597), LysC A279V (replacing L-alanine in position 279 of the encoded aspartate kinase protein according to sequence SEQ ID NO:10 with L-valine, see JP 6-261766 and Accession number E08179), LysC L297Q (replacing L-leucine in position 297 of the encoded aspartate kinase protein according to sequence SEQ ID NO:10 with L-glutamine; see DE 102006026328, LysC S301F (replacing L-serine in position 301 of the encoded aspartate kinase protein according to sequence SEQ ID NO:10 with L-phenylalanine; see U.S. Pat. No. 6,844,176 and Accession number E08180), LysC S301Y (replacing L-serine in position 301 of the encoded aspartate kinase protein according to sequence SEQ ID NO:10 with L-tyrosine, see Kalinowski et al. (Molecular and General Genetics 224, 317-324 (1990)) and Accession number X57226), LysC T308I (replacing L-threonine in position 308 of the encoded aspartate kinase protein according to sequence SEQ ID NO:10 with L-isoleucine; see JP 6-261766 and Accession number E08181).

LysC T311I (replacing L-threonine in position 311 of the encoded aspartate kinase protein according to sequence SEQ ID NO:10 with L-isoleucine; see WO 00/63388 and U.S. Pat. No. 6,893,848), LysC S317A (replacing L-serine in position 317 of the encoded aspartate kinase protein according to sequence SEQ ID NO:10 with L-alanine; see U.S. Pat. No. 5,688,671 and Accession number I74589), LysC R320G (replacing L-arginine in position 320 of the encoded aspartate kinase protein according to sequence SEQ ID NO:10 with glycine; see Jetten et al. (Applied Microbiology and Biotechnology 43, 76-82 (995)) and Accession number L27125), LysC G345D (replacing glycine in position 345 of the encoded aspartate kinase protein according to sequence SEQ ID NO:10 with L-aspartic acid; see Jetten et al. (Applied Microbiology and Biotechnology 43, 76-82 (995)) and Accession number L16848), LysC T380I (replacing L-threonine in position 380 of the encoded aspartate kinase protein according to sequence SEQ ID NO:10 with L-isoleucine; see WO 01/49854 and Accession number AX192358), and LysC S381F (replacing L-serine in position 381 of the encoded aspartate kinase protein according to sequence SEQ ID NO:10 with L-phenylalanine; see EP 0435132).

The lysC$^{FBR}$ allele, lysC T311I (replacing threonine in position 311 of the encoded aspartate kinase protein according to SEQ ID NO:10 with isoleucine) and a lysC$^{FBR}$ allele comprising at least one substitution selected from the group consisting of A279T (replacing alanine in position 279 of the encoded aspartate kinase proteins according to SEQ ID NO:10 with threonine), S381F (replacing serine in position 381 of the encoded aspartate kinase protein according to SEQ ID NO:10 with phenyl alanine) and S317A (replacing serine in position 317 of the encoded aspartate kinase protein according to SEQ ID NO:10 with alanine) are preferred. More preferable is the lysC$^{FBR}$ allele lysC T311I (replacing threonine in position 311 of the encoded aspartate kinase protein according to SEQ ID NO:10 with isoleucine).

The strain DSM 16833 (WO 06/063660) has a lysC$^{FBR}$ allele which encodes an aspartate kinase protein comprising the amino acid substitution T311I.

The strain NRRL B-11474 (U.S. Pat. No. 4,275,157) has a lysC$^{FBR}$ allele which encodes an aspartate kinase protein comprising the amino acid substitutions A279T and S381F.

Starting from strain DSM 16833, a mutant referred to as DM1915, which harbors a rel allele encoding a polypeptide in which L-leucine is present in position 38 of the amino acid sequence, was isolated in the manner described above. The nucleotide sequence of the coding region of the rel allele of the DM1915 mutant is depicted as SEQ ID NO:5 and the amino acid sequence of the encoded polypeptide is depicted as SEQ ID NO:6 and 8, respectively.

In addition, it is possible to use L-lysine-secreting coryneform bacteria which possess properties as known from the prior art.

L-Tryptophan-producing coryneform bacteria typically possess a feedback-resistant or desensibilized anthranilate synthase. The term feedback-resistant anthranilate synthase (TrpE) means anthranilate synthases which, compared to the wild type, have a lower sensitivity of at least 5% to 10%, or at least 10% to 15% or at least 10% to 20% to inhibition by tryptophan or 5-fluorotryptophan (Matsui et al., Journal of Bacteriology 169 (11): 5330-5332 (1987)) or similar analogs. The genes or alleles encoding these desensibilized anthranilate synthases are also referred to as trpE$^{FBR}$ alleles.

Examples of mutants or alleles of this kind are described, for example, in U.S. Pat. No. 6,180,373 and EP0338474.

L-Proline-producing coryneform bacteria have inter alia a γ-glutamyl kinase (ProB) which has a proteinogenic amino acid other than glycine in amino acid position 149 or a comparable position, preferably L-aspartic acid (WO06066758).

L-Valine-producing coryneform bacteria typically have a "feedback"-resistant or desensitized acetolactate synthase (acetohydroxy acid synthase; EC No. 2.2.1.6).

"Feedback"-resistant acetolactate synthase means an acetolactate synthase which, in comparison with the wild type, has lower sensitivity to inhibition by one or more of the amino acids selected from the group consisting of L-valine, L-isoleucine and L-leucine, preferably L-valine.

The acetolactate synthase (IlvB, IlvN) of *Corynebacterium* consists of a "large" subunit encoded by the ilvB gene and a "small" subunit encoded by the ilvN gene (Keilhauer et al., Journal of Bacteriology 175(17), 5595-5603 (1993)). WO 05/003357 and Elisakova et al. (Applied and Environmental Microbiology 71(1):207-13 (2005)) report on variants of the IlvN subunit which convey the acetolactate synthase resistance to L-valine, L-isoleucine and L-leucine. The amino acid sequence of one variant comprises L-aspartic acid instead of L-isoleucine in position 21 (IlvN I21D) and L-phenylalanine instead of L-isoleucine in position 22 (IlvN I22F). The amino acid sequence of the second variant comprises L-aspartic acid instead of glycine in position 20 (IlvN G20D), L-aspartic acid instead of L-isoleucine in position 21 (IlvN I21D) and L-phenylalanine instead of L-isoleucine in position 22 (IlvN I22F).

L-Isoleucine-producing coryneform bacteria typically have a "feedback"-resistant or -desensitized threonine dehydratase (=threonine deaminase).

"Feedback"-resistant threonine dehydratase means a threonine dehydratase (EC No. 4.3.1.19) which, in comparison with the wild type, has lower sensitivity to inhibition by L-isoleucine. The genes or alleles coding for this desensitized threonine dehydratase are also referred to as ilvA$^{FBR}$ alleles.

SEQ ID NO:17 depicts the coding region of the *Corynebacterium glutamicum* Wildtype ilvA gene according to the Accession numbers L01508 and NC_006958 of the NCBI database and SEQ ID NO:18 depicts the polypeptide encoded by this gene.

The threonine dehydratase variants described in U.S. Pat. No. 6,107,063 and in Morback et al. (Applied and Environmental Microbiology 61 (12), 4315-4320 (1995)) comprise one or more of the amino acid substitutions selected from the group consisting of:

IlvA M199V (replacing L-methionine in position 199 of the encoded threonine dehydratase protein according to SEQ ID NO:18 with L-valine; see U.S. Pat. No. 6,107,063), IlvA A257G (replacing L-alanine in position 257 of the encoded threonine dehydratase protein according to SEQ ID NO:18 with L-arginine; see U.S. Pat. No. 6,107,063), IlvA H278R (replacing L-histidine in position 278 of the encoded threonine dehydratase protein according to SEQ ID NO:18 with L-arginine; see U.S. Pat. No. 6,107,063), IlvA V323A (replacing L-valine in position 323 of the encoded threonine dehydratase protein according to SEQ ID NO:18 with L-alanine; see Morbach et al.), IlvA L351S (replacing L-leucine in position 351 of the encoded threonine dehydratase protein according to SEQ ID NO:18 with L-serine; see U.S. Pat. No. 6,107,063), IlvA D378G (replacing L-aspartic acid in position 378 of the encoded threonine dehydratase protein according to SEQ ID NO:18 with glycine; see Morbach et al.), The mutants obtained show increased secretion or production of the desired amino acid in a fermentation process, in comparison with the starting strain or parent strain employed.

The invention likewise relates to an isolated polynucleotide encoding a polypeptide having GTP-pyrophosphate kinase enzyme activity, which polypeptide comprises one of the proteinogenic amino acids other than L-proline in position 38 or in a corresponding or comparable position of the amino acid sequence, with preference being given to the substitution with L-leucine.

The polynucleotide of the invention may be isolated from a mutant of the invention.

It is furthermore possible to use in-vitro methods for the mutagenesis of the rel gene. The use of in-vitro methods involves subjecting isolated polynucleotides which comprise a rel gene of a coryneform bacterium, preferably the *Corynebacterium glutamicum* wild type gene described in the prior art, to a mutagenic treatment.

The isolated polynucleotides may be, for example, isolated total DNA or chromosomal DNA or else amplicons of the rel gene, which have been prepared with the aid of the polymerase chain reaction (PCR). Such amplicons are also referred to as PCR products. Instructions for the amplification of DNA sequences with the aid of the polymerase chain reaction can be found by the skilled worker, inter alia, in the manual by Gait: Oligonucleotide Synthesis: A Practical Approach (IRL Press, Oxford, UK, 1984) and Newton and Graham: PCR (Spektrum Akademischer Verlag, Heidelberg, Germany, 1994). It is likewise possible to incorporate the rel gene to be mutagenized first into a vector, for example into a bacteriophage or into a plasmid.

Suitable methods of in-vitro mutagenesis are, inter alia, the treatment with hydroxylamine according to Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992), the use of mutagenic oligonucleotides (T. A. Brown: Gentechnologie für Einsteiger [Genetic engineering for beginners], Spektrum Akademischer Verlag, Heidelberg, 1993 and R. M. Horton: PCR-Mediated Recombination and Mutagenesis, Molecular Biotechnology 3, 93-99 (1995)) and the use of a polymerase chain reaction using a DNA polymerase with a high error rate. An example of such a DNA polymerase is the Mutazyme DNA Polymerase (GeneMorph PCR Mutagenesis Kit, No. 600550) from Stratagene (La Jolla, Calif., USA).

Further instructions and reviews on the generation of mutations in vivo or in vitro can be found in the prior art and in known textbooks of genetics and molecular biology, such as, for example, the textbook by Knippers ("Molekulare Genetik", 6th edition, Georg Thieme Verlag, Stuttgart, Germany, 1995), that by Winnacker ("Gene and Klone", VCH Verlagsgesellschaft, Weinheim, Germany, 1990) or that by Hagemann ("Allgemeine Genetik", Gustav Fischer Verlag, Stuttgart, 1986).

The invention furthermore relates to an isolated polynucleotide encoding a polypeptide having GTP-pyrophosphate kinase enzyme activity, which polypeptide comprises the amino acid sequence of SEQ ID NO:2, with one of the proteinogenic amino acids other than L-proline being present in position 38 of said amino acid sequence, preferably the substitution with L-leucine. L-Glutamic acid is optionally contained in position 262 of SEQ ID NO:2.

The invention furthermore relates to an isolated polynucleotide encoding a polypeptide having GTP-pyrophosphate kinase enzyme activity, which polypeptide comprises an amino acid sequence having a length of 760 amino acids, with one of the proteinogenic L-amino acids other than L-proline, preferably L-leucine, being present in position 38.

The invention furthermore relates to an isolated polynucleotide encoding a polypeptide having GTP-pyrophosphate kinase enzyme activity, which polypeptide comprises, in positions 19 to 57 of the amino acid sequence, the amino acid sequence corresponding to positions 19 to 57 of SEQ ID NO:6 or 8 respectively. The amino acid sequence of the encoded polypeptide preferably comprises an amino acid sequence corresponding to positions 9 to 107 of SEQ ID NO:6 or 8, respectively, or to positions 9 to 207 of SEQ ID NO:6 or 8, respectively, or to positions 9 to 407 of SEQ ID NO:6 or 8, respectively, or to positions 9 to 607 of SEQ ID NO:6 or 8, respectively, or to positions 9 to 707 of SEQ ID NO:6 or 8, respectively, or to positions 2 to 707 of SEQ ID NO:6 or 8, respectively, or to positions 9 to 757 of SEQ ID NO:6 or 8, respectively, or to positions 2 to 757 of SEQ ID NO:6 or 8, respectively, or to positions 2 to 758 of SEQ ID NO:6 or 8, respectively, or to positions 2 to 759 of SEQ ID NO:6 or 8, respectively, L-glutamic acid being optionally present in position 262. The length of the encoded polypeptide comprises very particularly preferably 760 amino acids.

The invention furthermore relates to an isolated polynucleotide encoding a polypeptide having GTP-pyrophosphate kinase enzyme activity, which polypeptide comprises one of the proteinogenic amino acids other than L-proline, preferably L-leucine, in position 38 of the amino acid sequence or in a corresponding or comparable position, and comprising a nucleotide sequence identical to the nucleotide sequence of a polynucleotide which is obtainable by a polymerase chain reaction (PCR) using the primer pair whose nucleotide sequences comprise in each case at least 15 contiguous nucleotides selected from the nucleotide sequence between positions 1 and 861, preferably between positions 1 and 750 of SEQ ID NO:3 or SEQ ID NO:7 and from the complementary nucleotide sequence between positions 3800 and 865, preferably between positions 3800 and 3031 of SEQ ID NO:3 or SEQ ID NO:7. One example of a suitable primer pair of this kind is depicted in SEQ ID NO:19 and SEQ ID NO:20. The preferred starting material (template DNA) is chromosomal DNA of coryneform bacteria, in particular of those which have been treated with a mutagen, preferably, the chromosomal DNA of the genus *Corynebacterium*, and more preferably, the species *Corynebacterium glutamicum*.

The invention furthermore relates to an isolated polynucleotide which hybridizes with the nucleotide sequence complementary to SEQ ID NO:5 under stringent conditions and which encodes a polypeptide having GTP-pyrophosphate kinase enzyme activity, which polypeptide comprises one of the proteinogenic amino acids other than L-proline, preferably L-leucine, in position 38 of the amino acid sequence or in a corresponding or comparable position.

Instructions regarding the hybridization of nucleic acids or polynucleotides can be found by the skilled worker, inter alia, in the manual "The DIG System User's Guide for Filter Hybridization" from Boehringer Mannheim GmbH (Mannheim, Germany, 1993) and in Liebl et al. (International Journal of Systematic Bacteriology 41: 255-260 (1991)). The hybridization is carried out under stringent conditions, i.e. only hybrids in which the probe, i.e. a polynucleotide comprising the nucleotide sequence complementary to SEQ ID NO:5, and the target sequence, i.e. the polynucleotides treated or identified with the probe, are at least 90% identical, are formed. The stringency of the hybridization, including that of the washing steps, is known to be influenced or determined by varying the buffer composition, the temperature and the salt concentration. The hybridization reaction is carried out at relatively low stringency compared to the washing steps (Hybaid Hybridisation Guide, Hybaid Limited, Teddington, UK, 1996).

For example, a buffer corresponding to 5×SSC buffer at a temperature of approx. 50° C.-68° C. may be used for the hybridization reaction. In this case, probes may also hybridize with polynucleotides which are less than 90% identical to the nucleotide sequence of the probe employed. Such hybrids are less stable and are removed by washing under stringent conditions. This may be achieved, for example, by lowering the salt concentration to 2×SSC and, where appropriate, subsequently to 0.5×SSC (The DIG System User's Guide for Filter Hybridisation, Boehringer Mannheim, Mannheim, Germany, 1995), with the temperature being set to approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. Temperature ranges of approx. 64° C.-68° C. or approx. 66° C.-68° C. are preferred. It is possible, where appropriate, to lower the salt concentration down to a concentration corresponding to 0.2×SSC or 0.1×SSC. The SSC buffer comprises, where appropriate, sodium dodecyl sulfate (SDS) in a concentration of 0.1%. By gradually increasing the hybridization temperature in steps of approx. 1-2° C. from 50° C. to 68° C., it is possible to isolate polynucleotide fragments which have at least 90% or at least 91%, preferably at least 92% or at least 93% or at least 94% or at least 95% or at least 96%, and more preferably at least 97% or at least 98% or at least 99%, identity to the sequence or complementary sequence of the probe employed and which encode a polypeptide which has GTP-pyrophosphate kinase enzyme activity and comprises the amino acid substitution of the invention. The nucleotide sequence of the polynucleotide obtained in this way is determined by known methods. Further instructions regarding hybridization are commercially available in the form of "kits" (e.g. DIG Easy Hyb from Roche Diagnostics GmbH, Mannheim, Germany, Catalog No. 1603558). The nucleotide sequences thus obtained encode polypeptides having GTP-pyrophosphate kinase enzyme activity, which polypeptides are at least 90%, preferably at least 92% or at least 94% or at least 96%, and very particularly preferably at least 97% or at least 98% or at least 99%, identical to the amino acid sequence of SEQ ID NO:6 or SEQ ID NO:8, respectively, and which comprise the amino acid substitution of the invention, L-glutamic acid being optionally present in position 262.

The invention furthermore relates to an isolated polynucleotide encoding a polypeptide having GTP-pyrophosphate kinase enzyme activity, which polypeptide comprises one of the proteinogenic amino acids other than L-proline in position 38 or in a corresponding or comparable position of the amino acid sequence, the substitution with L-leucine being preferred, and which comprises an amino acid sequence which moreover is at least 90%, preferably at least 92% or at least 94% or at least 96%, and very particularly preferably at least 97% or at least 98% or at least 99%, identical to the amino acid sequence of SEQ ID NO:6 or SEQ ID NO:8, respectively, L-glutamic acid being optionally present in position 262.

The invention furthermore relates to an isolated polynucleotide encoding a polypeptide having GTP-pyrophosphate kinase enzyme activity, which polypeptide comprises one of the proteinogenic amino acids other than L-proline in position 38 or in a corresponding or comparable position of the amino acid sequence, the substitution with L-leucine being preferred, and comprising a nucleotide sequence which moreover is at least 90%, preferably at least 92% or at least 94% or at least 96%, and very particularly preferably at least 97% or at least 98% or at least 99%, identical to the nucleotide sequence of SEQ ID NO:5, adenine being optionally present in position 785.

In addition, preference is given to those isolated polynucleotides encoding a polypeptide having GTP-pyrophosphate kinase enzyme activity, which polypeptide comprises one of the proteinogenic amino acids other than L-proline, preferably L-leucine, in position 38 of the amino acid sequence or in a corresponding or comparable position, and comprising at least one sequence motif or an amino acid sequence selected from the group consisting of Ser-Gly-Asp/Glu-Pro-Tyr-Ile-Thr (SEQ ID NO:24)/Ile-His-Pro-Leu-Ala-Val (SEQ ID NO:25), Ala-Ala/Gly-Leu-Leu-His-Asp-Thr-Val-Glu-Asp-Thr (SEQ ID NO:26) and Thr-Val-Asp-Phe-Ala-Tyr-Ala-Val-His-Thr-Glu-Val-Gly-His-Arg (SEQ ID NO:27).

The terms "Asp/Glu", "Thr/Ile" and "Ala/Gly" mean that "Asp or Glu" or "Thr or Ile" or "Ala or Gly" are present in the corresponding position.

The invention furthermore relates to an isolated polynucleotide encoding a polypeptide having GTP-pyrophosphate kinase enzyme activity, which polypeptide comprises the amino acid sequence of SEQ ID NO:6 or 8, respectively, L-glutamic acid being optionally present in position 262. The encoded polypeptide comprises, where appropriate, one (1) or more conservative amino acid substitution(s). Preferably, the polypeptide comprises no more than two (2), no more than three (3), no more than four (4) or no more than five (5), conservative amino acid substitutions.

The invention furthermore relates to an isolated polynucleotide encoding a polypeptide having GTP-pyrophosphate kinase enzyme activity, which polypeptide comprises the amino acid sequence of SEQ ID NO:6 or 8, respectively, including an extension at the N- or C-terminus by at least one (1) amino acid. This extension has no more than 50, 40, 30, 20, 10, 5, 3 or 2 amino acids or amino acid residues. L-Glutamic acid being optionally contained in position 262 of SEQ ID NO:6 or 8, respectively.

The invention relates to rel alleles encoding polypeptide variants of SEQ ID NO:6 or 8, respectively, L-glutamic acid being optionally present in position 262, which comprise one or more insertions or deletions. These preferably comprise no more than 5, no more than 4, no more than 3 or no more than 2 insertions or deletions of amino acids. Preferably, the sequence motifs Ser-Gly-Asp/Glu-Pro-Tyr-Ile-Thr (SEQ ID NO:24)/Ile-His-Pro-Leu-Ala-Val (SEQ ID NO:25) and/or Ala-Ala/Gly-Leu-Leu-His-Asp-Thr-Val-Glu-Asp-Thr (SEQ ID NO:26) and/or Thr-Pro-Val-Asp-Phe-Ala-Tyr-Ala-Val-His-Thr-Glu-Val-Gly-His-Arg (SEQ ID NO:27) are not disrupted by such insertions/deletions.

The invention relates to an isolated polynucleotide comprising the nucleotide sequence according to SEQ ID NO:5 or 7, adenine being optionally present in position 785 of SEQ ID NO:5 or position 1535 of SEQ ID NO:7.

The invention relates to an isolated polynucleotide comprising the rel allele of the DM1915 mutant.

The invention relates to an isolated polynucleotide comprising part of the coding region of a rel allele of the invention, said isolated polynucleotide comprising in any case that part of the coding region which comprises the amino acid substitution in position 38 of the amino acid sequence of the encoded polypeptide.

A nucleic acid molecule or DNA fragment comprises a molecule or fragment which encodes at least one amino acid sequence corresponding to positions 19 to 57 of SEQ ID NO:2 or which encodes at least one amino acid sequence corresponding to positions 9 to 107 of SEQ ID NO:2 or which encodes at least one amino acid sequence corresponding to positions 9 to 207 of SEQ ID NO:2 or which encodes at least one amino acid sequence corresponding to positions 9 to 407 of SEQ ID NO:2 or which encodes at least one amino acid sequence corresponding to positions 9 to 607 of SEQ ID NO:2 or which encodes at least one amino acid sequence corresponding to positions 9 to 707 of SEQ ID NO:2 or which encodes at least one amino acid sequence corresponding to positions 2 to 707 of SEQ ID NO:2, or which encodes at least one amino acid sequence corresponding to positions 9 to 757 of SEQ ID NO:2 or which encodes at least one amino acid sequence corresponding to positions 2 to 757 of SEQ ID NO:2, or which encodes at least one amino acid sequence corresponding to positions 2 to 758 of SEQ ID NO:2, or which encodes at least one amino acid sequence corresponding to positions 2 to 759 of SEQ ID NO:2, with one of the proteinogenic amino acids other than L-proline, preferably L-leucine, being present in the position corresponding to 38 of SEQ ID NO:2. L-Glutamic acid is optionally present in position 262 of SEQ ID NO:2.

An example of a reading frame of the invention, comprising a polynucleotide encoding at least the amino acid sequence of positions 19 to 57 corresponding to SEQ ID NO:2, with one of the proteinogenic amino acids (Xaa) other than L-proline being present in the position corresponding to 38 of the amino acid sequence, is listed below:

```
gcc agg ctt gcc cgc agc ctc aca gga aac cgc gtt
Ala Arg Leu Ala Arg Ser Leu Thr Gly Asn Arg Val
    20                  25                  30 cgc acc aac cct gtg ctg gat nnn ctg ctg agc atc
Arg Thr Asn Pro Val Leu Asp Xaa Leu Leu Ser Ile
                35                  40 cac cgg caa ttt cac cca cgc gcc gac gta caa gtg
His Arg Gln Phe His Pro Arg Ala Asp Val Gln Val
        45                  50 ttg gaa cgt
Leu Glu Arg
55
```

It is likewise depicted as SEQ ID NO:11. The amino acid sequence encoded by this reading frame is depicted as SEQ ID NO:12. Position 20 in SEQ ID NO:12 corresponds to position 38 of SEQ ID NO:2, 4, 6 or 8, respectively.

Nucleic acid molecules encoding at least one amino acid sequence corresponding to positions 19 to 57 of SEQ ID NO:6 or 8, respectively, or at least corresponding to position 9 to 107 of SEQ ID NO:6 or 8, respectively, or at least corresponding to positions 9 to 207 of SEQ ID NO:6 or 8, respectively, or at least corresponding to positions 9 to 407 of SEQ ID NO:6 or 8, respectively, or at least corresponding to positions 9 to 607 of SEQ ID NO:6 or 8, respectively, or at least corresponding to positions 9 to 707 of SEQ ID NO:6 or 8, respectively, or at least corresponding to positions 2 to 707 of SEQ ID NO: 6 or 8, respectively, or at least corresponding to positions 9 to 757 of SEQ ID NO: 6 or 8, respectively, or at least corresponding to positions 2 to 757 of SEQ ID NO: 6 or 8, respectively, or at least corresponding to positions 2 to 758 of SEQ ID NO: 6 or 8, respectively, or at least corresponding to positions 2 to 759 of SEQ ID NO: 6 or 8, respectively, L-glutamic acid being optionally present in position 262 are preferred.

An example of a reading frame of the invention, comprising a polynucleotide encoding at least the amino acid sequence corresponding to positions 19 to 57 of SEQ ID NO:6 or 8, respectively, is listed below:

```
gcc agg ctt gcc cgc agc ctc aca gga aac cgc gtt
Ala Arg Leu Ala Arg Ser Leu Thr Gly Asn Arg Val
    20                  25                  30 cgc acc aac cct gtg ctg gat ctg ctg ctg agc atc
Arg Thr Asn Pro Val Leu Asp Leu Leu Leu Ser Ile
                35                  40 cac cgg caa ttt cac cca cgc gcc gac gta caa gtg
His Arg Gln Phe His Pro Arg Ala Asp Val Gln Val
        45                  50 ttg gaa cgt
Leu Glu Arg
55
```

The reading frame is likewise depicted as SEQ ID NO:13. SEQ ID NO:14 depicts the amino acid sequence encoded by said reading frame. Position 20 in SEQ ID NO:14 corresponds to position 38 of SEQ ID NO:2, 4, 6 or 8, respectively.

Very particular preference is given to nucleic acid molecules comprising at least one nucleotide sequence corresponding to positions 805 to 921 of SEQ ID NO:7, or at least one nucleotide sequence corresponding to positions 655 to 1071 of SEQ ID NO:7, or at least one nucleotide sequence corresponding to positions 355 to 1371 of SEQ ID NO:7, or at least one nucleotide sequence corresponding to positions 55 to 2671 of SEQ ID NO:7, or at least one nucleotide sequence corresponding to positions 1 to 2725 of SEQ ID NO:7, adenine being optionally present in position 1535.

In addition, the reading frames of the invention, as shown by way of example in SEQ ID NO:11 and 13 as nucleotide sequence and in SEQ ID NO:12 and SEQ ID NO:14 in the form of the encoded amino acid sequence, may comprise one or more mutations resulting in one or more conservative amino acid substitutions. The mutations preferably result in no more than 4%, no more than 2% or no more than 1%, conservative amino acid substitutions. The reading frames of the invention may furthermore comprise one more silent mutations. The reading frames of the invention comprise preferably no more than 4%, and more preferably no more than 2% to no more than 1%, silent mutations.

The isolated polynucleotides of the invention may be used in order to produce recombinant strains of microorganisms, which release amino acids into the surrounding medium or accumulate them in the cell interior in an improved manner, compared to the starting or parent strain.

A widespread method of incorporating mutations into genes of coryneform bacteria is that of allele substitution which is also referred to as gene replacement. This process involves transferring a DNA fragment comprising the mutation of interest into the desired strain of a coryneform bacterium and incorporating said mutation into the chromosome of the desired strain by at least two recombination events or cross-over events or replacing the sequence of a gene in the strain in question with the mutated sequence.

Schwarzer and Pühler (Bio/Technology 9, 84-87 (1991)) used this method in order to incorporate a lysA allele carrying a deletion and a lysA allele carrying an insertion into the *C. glutamicum* chromosome, instead of the wild type gene. Schäfer et al. (Gene 145, 69-73 (1994)) employed said method, in order to incorporate a deletion into the *C. glutamicum* hom-thrB operon. Nakagawa et al. (EP 1108790) and Ohnishi et al. (Applied Microbiology and Biotechnology 58(2), 217-223 (2002)) employed said method in order to incorporate various mutations, starting from the isolated alleles, into the *C. glutamicum* chromosome. In this way, Nakagawa et al. succeeded in incorporating a mutation referred to as Val59Ala into the homoserine dehydrogenase gene (hom), a mutation referred to as Thr311Ile into the aspartate kinase gene (lysC and ask, respectively), a mutation referred to as Pro458Ser into the pyruvate carboxylase gene (pyc) and a mutation referred to as Ala213Thr into the glucose 6-phosphate dehydrogenase gene (zwf) of *C. glutamicum* strains.

A process of the invention may use a polynucleotide of the invention, which comprises the entire coding region, as depicted, for example, in SEQ ID NO:5, or which comprises part of the coding region, such as, for example, the nucleotide sequence encoding at least the amino acid sequence corresponding to positions 19 to 57 of SEQ ID NO:6 or 8, respectively, and depicted as SEQ ID NO:11 and 13. The part of the coding region corresponding to SEQ ID NO:11 and 13 has a length of 117 nucleobases. Preference is given to those parts of SEQ ID No:7 which encompass at least the sequence between positions 1071 and 665, or at least between positions 1371 and 355 and accordingly have a length of 407 or 1017 nucleotides.

SEQ ID NO:15 shows an example of a polynucleotide of the invention which encompasses a part of the coding region.

In said method, the DNA fragment comprising the mutation of interest is typically present in a vector, in particular a plasmid which preferably is replicated only to a limited extent, if at all, by the strain to be provided with the mutation. The auxiliary or intermediate host used, in which the vector can be replicated, may be a bacterium of the genus *Escherichia*, preferably of the species *Escherichia coli*.

Examples of plasmid vectors of this kind are the pK*mob and pK*mobsacB vectors described by Schäfer et al. (Gene 145, 69-73 (1994)), such as, for example, pK18mobsacB, and the vectors described in WO 02/070685 and WO 03/014362. These are replicative in *Escherichia coli* but not in coryneform bacteria. Suitable are vectors comprising a gene with a conditionally negative-dominant action, such as, for example, the sacB gene (levansucrase gene) of *Bacillus*, for example, or the galK gene (galactose kinase gene) of *Escherichia coli*, for example. (A gene with conditionally negative-dominant action means a gene which, under certain conditions, is disadvantageous, for example toxic, to the host but which has, under different conditions, no adverse effects on the host carrying the gene.) Said vectors make possible the selection for recombination events in which the vector is eliminated from the chromosome. Nakamura et al. (U.S. Pat. No. 6,303,383) furthermore described a temperature-sensitive plasmid for coryneform bacteria, which can replicate only at temperatures below 31° C.

The vector is subsequently transferred to the coryneform bacterium by way of conjugation, for example by the method of Schäfer (Journal of Bacteriology 172, 1663-1666 (1990)), or transformation, for example by the method of Dunican and Shivnan (Bio/Technology 7, 1067-1070 (1989)) or the method of Thierbach et al. (Applied Microbiology and Biotechnology 29, 356-362 (1988)). The DNA may also be transferred, where appropriate, by particle bombardment.

Incorporation of the mutation is achieved after homologous recombination by means of a first cross-over event causing integration and of a suitable second cross-over event causing excision in the target gene or in the target sequence, resulting in a recombinant bacterium.

The strains obtained may be identified and characterized by using, inter alia, the methods of Southern blotting hybridization, polymerase chain reaction, sequence determination, the method of fluorescence resonance energy transfer (FRET) (Lay et al. Clinical Chemistry 43, 2262-2267 (1997)) or methods of enzymology.

Accordingly, the invention further relates to a process for preparing a coryneform bacterium, which comprises
   a) transferring a polynucleotide of the invention to a coryneform bacterium,
   b) replacing the GTP-pyrophosphate kinase gene which encodes an amino acid sequence with L-proline in position 38 or in a comparable position of said amino acid sequence and which is present in the chromosome of said coryneform bacterium with the polynucleotide of a), which encodes an amino acid sequence having a different proteinogenic L-amino acid, preferably L-leucine, in position 38 or in a comparable position of said amino acid sequence, and
   c) propagating the coryneform bacterium obtained by steps a) and b).

In this way a recombinant coryneform bacterium is obtained which comprises one (1) rel allele of the invention, instead of the wild type rel gene.

Another process of the invention for preparing a microorganism comprises
   a) transferring a polynucleotide of the invention, which encodes a polypeptide having GTP-pyrophosphate kinase enzyme activity, to a microrganism,
   b) replicating said polynucleotide in said microorganism, and
   c) propagating the microorganism obtained by steps a) and b).

In this way, a recombinant microorganism is obtained, which comprises at least one (1) copy or several copies of a polynucleotide of the invention, which polynucleotide encodes a GTP-pyrophosphate kinase comprising one of the proteinogenic amino acids other than L-proline in position 38 or a comparable position of the amino acid sequence of the encoded polypeptide, the substitution with L-leucine being preferred.

The invention further relates to hosts or host cells, preferably microorganisms, more preferably coryneform bacteria and bacteria of the genus *Escherichia*, which comprise the polynucleotides of the invention. The invention likewise relates to microorganisms prepared by using the isolated polynucleotides. Such microorganisms or bacteria are also referred to as recombinant microorganisms or recombinant bacteria. In the same way, the invention relates to vectors comprising the polynucleotides of the invention. Finally, the invention likewise relates to hosts harboring said vectors.

The isolated polynucleotides of the invention may likewise be used for achieving overexpression of the polypeptides encoded by them.

Overexpression means an increase in the intracellular concentration or activity of a ribonucleic acid, a protein or an enzyme. In this invention, rel alleles or polynucleotides which encode GTP-pyrophosphate kinases comprising one of the proteinogenic amino acids other than L-proline in position 38 of the amino acid sequence of the encoded polypeptide, with the substitution with L-leucine being preferred, are overexpressed. Enzymes endogenous to the host—"aminopeptidases"—are known to be able to cleave N-terminal amino acids, in particular the N-terminal methionine, off the polypeptide produced. Said increase in the concentration or activity of a gene product can be achieved, for example, by increasing the copy number of the corresponding polynucleotides by at least one copy.

A method of increasing the copy number comprises incorporating the appropriate gene or allele into a vector, preferably a plasmid, which is replicated by a coryneform bacterium. Examples of suitable plasmid vectors are pZ1 (Menkel et al., Applied and Environmental Microbiology (1989) 64: 549-554) or the pSELF vectors described by Tauch et al. (Journal of Biotechnology 99, 79-91 (2002)). A review article on plasmids in *Corynebacterium glutamicum* can be found in Tauch et al. (Journal of Biotechnology 104, 27-40 (2003)).

Another common method of achieving overexpression is the process of chromosomal gene amplification. This method involves inserting at least one additional copy of the gene or allele of interest into the chromosome of a coryneform bacterium.

For the hom-thrB operon in Reinscheid et al. (Applied and Environmental Microbiology 60, 126-132 (1994)), a plasmid which is non-replicative in *C. glutamicum* and which comprises the gene of interest is transferred to a coryneform bacterium. After homologous recombination by means of a cross-over event, the resulting strain comprises at least two copies of the gene or allele in question.

WO 03/040373 and US-2003-0219881-A1 describe that one or more copies of the gene of interest are inserted at a desired side of the *C. glutamicum* chromosome by means of at least two recombination events. In this way, for example, a copy of a lysC allele encoding a L-lysine-insensitive aspartate kinase was incorporated into the *C. glutamicum* gluB gene.

WO 03/014330 and US-2004-0043458-A1 describe that at least one further copy, preferably in tandem arrangement to the gene or allele already present, of the gene of interest is incorporated by means of at least two recombinantion events at the natural locus. In this way it was possible, for example, to achieve a tandem duplication of a lysC$^{FBR}$ allele at the natural lysC gene locus.

Another method of achieving overexpression comprises linking the appropriate gene or allele functionally (operably linked) to a promoter or an expression cassette. Examples of suitable promotors for *Corynebacterium glutamicum* are described in the review article by Patek et al. (Journal of Biotechnology 104(1-3), 311-323 (2003)). In a similar manner, the variants of the dapA promotor described by Vasicova et al (Journal of Bacteriology 181, 6188-6191 (1999)) may be used, for example the promotor A25. The gap promotor of *Corynebacterium glutamicum* (EP 06007373) may also be used. It is finally possible to use the well-known promotors T3, T7, SP6, M13, lac, tac and trc described by Amann et al. (Gene 69(2), 301-315 (1988)) and Amann and Brosius (Gene 40(2-3), 183-190 (1985)). Such a promotor may be inserted, for example, upstream of the rel allele, at a distance of approximately 1-500 nucleotides from the start codon, of a recombinant coryneform bacterium, which allele encodes a protein, which comprises, instead of the amino acid L-proline naturally present in position 38, a different proteinogenic amino acid. A promotor of this kind may naturally likewise be inserted upstream of the coding region of the rel allele of a mutant of the invention. It is furthermore possible to link an isolated polynucleotide of the invention, which encodes a variant of the invention of GTP-pyrophosphate kinase, to a promoter and to incorporate the expression unit obtained into an extrachromosomally replicating plasmid or into the chromosome of a coryneform bacterium.

In addition, it is possible to mutate the promoter and regulatory regions or the ribosomal binding site which is located upstream of the structural gene. Measures of extending the mRNA lifetime likewise improve expression. Preventing the degradation of the enzyme protein furthermore likewise enhances enzyme activity. Alternatively, the gene or allele in question may furthermore be overexpressed by altering the media composition and the culturing process.

The overexpression measures increase the activity or concentration of the protein in question by at least 10%, 25%, 50%, 75%, 100%, 150%, 200%, 300%, 400% or 500%, up to no more than 1000% or 2000%, based on the activity or concentration of the protein in the starting microorganism or parent strain. A starting microorganism or parent strain means a microorganism which is subjected to the measures of the invention.

The concentration of the protein may be determined via 1- and 2-dimensional protein gel fractionation and subsequent optical identification of the protein concentration in the gel, using appropriate evaluation software. A common method of preparing the protein gels in the case of coryneform bacteria and of identifying the proteins is the procedure described by Hermann et al. (Electrophoresis, 22:1712-23 (2001)). The protein concentration may likewise be determined by Western blot hybridization using an antibody specific for the protein to be detected (Sambrook et al., Molecular cloning: a laboratory manual. 2$^{nd}$ Ed. Cold Spring Harbor Laboratory Press, Cold Spring Harbor, N.Y., 1989) and subsequent optical evaluation using appropriate concentration determination software (Lohaus and Meyer (1998) Biospektrum 5:32-39; Lottspeich, Angewandte Chemie 38: 2630-2647 (1999)).

The invention relates to processes for overexpressing the GTP-pyrophosphate kinases of the invention. A process of the invention for overexpression comprises, inter alia, increasing the copy number of a polynucleotide of the invention, which polynucleotide encodes a GTP-pyrophosphate-kinase variant comprising one of the proteinogenic amino acids other than L-proline in position 38 or the corresponding position of the encoded amino acid sequence, by at least one (1) or several copies. Another process of the invention comprises functionally linking a promotor to the polynucleotide.

The invention furthermore relates to microorganisms having an increased concentration or activity of the GTP-pyrophosphate kinase variants of the invention in their cell interior.

For improved production of L-amino acids different genes in the mutants or recombinant strains of the invention may be overexpressed, preferably endogenous genes.

"Endogenous genes" or "endogenous nucleotide sequences" means the genes or the nucleotide sequences or alleles present in the population of a species.

Thus it is possible to overexpress for the preparation of L-lysine one or more of the genes selected from the group consisting of a dapA gene encoding a dihydrodipicolinate synthase (DapA, EC No. 4.2.1.52), such as, for example, the *Corynebacterium glutamicum* wild-type dapA gene described in EP 0 197 335, a lysA gene encoding a diaminopimelate decarboxylase (LysA, EC No. 4.1.1.20), such as, for example, the *Corynebacterium glutamicum* lysA gene ATCC13869, described in U.S. Pat. No. 6,090,597, a zwf gene encoding a glucose-6-phosphate dehydrogenase (Zwf, EC No. 1.1.1.49) such as, for example, the *Corynebacterium glutamicum* wild-type zwf gene described in JP-A-09224661 and EP-A-1108790, the *Corynebacterium glutamicum* zwf alleles described in US-2003-0175911-A1, which encode a protein having glucose 6-phosphate dehydrogenase activity in which, for example, the L-alanine in position 243 of the amino acid sequence has been replaced with L-threonine or in which the L-aspartic acid in position 245 has been replaced with L-serine, a pyc gene encoding a pyruvate carboxylase (Pyc, EC No. 6.4.1.1), such as, for example, the *Corynebacterium glutamicum* wild-type pyc gene described in DE-A-198 31 609 and EP 1108790, the *Corynebacterium glutamicum* pyc allele described in EP 1 108 790, which encodes a protein having pyruvate carboxylase activity in which L-proline in position 458 of the amino acid sequence has been replaced by L-serine, the *Corynebacterium glutamicum* pyc alleles described in WO 02/31158 and in particular EP1325135B1, which encode proteins having pyruvate carboxylate activity which carry one or more of the amino acid substitutions selected from the group consisting of L-valine in position 1 replaced with L-methionine, L-glutamic acid in position 153 replaced with L-aspartic acid, L-alanine in position 182 replaced with L-serine, L-alanine in position 206 replaced with L-serine, L-histidine in position 227 replaced with L-arginine, L-alanine in position 455 replaced with glycine and L-aspartic acid in position 1120 replaced with L-glutamic acid, a lysC gene encoding an aspartate kinase (LysC, EC No. 2.7.2.4), such as, for example, that of *Corynebacterium glutamicum* wild-type lysC gene described as SEQ ID NO:281 in EP-A-1108790 (see also accession numbers AX120085 and 120365) and that of *Corynebacterium glutamicum* wild-type lysC gene, described as SEQ ID NO:25 in WO 01/00843 (see accession number AX063743), a lysC$^{FBR}$ allele, in particular according to Table 1, which encodes a feedback-resistant aspartate kinase variant, a lysE gene encoding a lysine export protein (LysE), such as, for example, the *Corynebacterium glutamicum* wild-type lysE gene described in DE-A-195 48 222, the aat gene encoding an aspartate amino transferase (Aat, EC No. 2.6.1.1) (the aat gene of *Corynebacterium glutamicum* ATCC13032 is described, for example, in Kalinowski et al (Journal of Biotechnology 104 (1-3), 5-25 (2003); see also Accession number NC_006958). It is referred to there as aspB gene. U.S. Pat. No. 6,004,773 refers to a gene encoding an aspartate amino transferase as aspC. Marienhagen et al (Journal of Bacteriology 187 (22), 7693-7646 (2005) refer to the aat gene as aspT gene.)), the *Corynebacterium glutamicum* wild-type zwa1 gene encoding the Zwa1 protein (U.S. Pat. No. 6,632,644).

In addition to using the alleles of the invention of the rel gene, for the purpose of producing L-lysine, to simultaneously attenuation or eliminate, where appropriate, may be obtained with simultaneous overexpression of at least one of the genes selected from the abovementioned group of genes, one or more of the endogenous genes selected from the group consisting of a pgi gene encoding glucose 6-phosphate isomerase (Pgi, EC No. 5.3.1.9), such as, for example, the *Corynebacterium glutamicum* pgi gene described in U.S. Pat. No. 6,586,214 and U.S. Pat. No. 6,465,238, a hom gene encoding homoserine dehydrogenase (Horn, EC No. 1.1.1.3), such as, for example, the *Corynebacterium glutamicum* hom gene described in EP-A-0131171, a thrB gene encoding homoserine kinase (ThrB, EC No. 2.7.1.3.9), such as, for example, the *Corynebacterium glutamicum* thrB gene described by Peoples et al. (Molecular Microbiology 2 (1988): 63-72)), and a pfkB gene encoding phosphofructokinase (PfkB, EC No. 2.7.1.56), such as, for example, the *Corynebacterium glutamicum* pfkB gene described in WO 01/00844 (sequence no. 57), an mdh gene encoding malate dehydrogenase (Mdh, EC No. 1.1.1.37), as described, for example, in WO 02/02778, an mqo gene coding for malate-quinone oxidoreductase (Mqo, EC No. 1.1.99.16), as described, for example, in U.S. Pat. No. 7,094,106 and PCT/EP2005/057216.

In this connection, the term "attenuation" describes the reduction or elimination of the intracellular activity of one or more enzymes (proteins) which are encoded by the corresponding DNA in a microorganism which is achieved, for example, by using a weak promoter or using a gene or allele which encodes a corresponding enzyme having low activity, or inactivating the corresponding gene or enzyme (protein), and, where appropriate, combining these measures.

As a result of using the measures for achieving attenuation, the activity or concentration of the corresponding protein is lowered to from 0 to 75%, from 0 to 50%, from 0 to 25%, from 0 to 10%, or from 0 to 5%, of the activity or concentration of the wild-type protein or of the activity or concentration of the protein in the starting microorganism.

Mutations which come into consideration for generating an attenuation are transitions, transversions, insertions and deletions of at least one (1) base pair or nucleotide. Depending on the effect which the amino acid substitution elicited by the mutation has on the enzyme activity, reference is made to missense mutations or nonsense mutations. A missense mutation leads to the replacement of a given amino acid in a protein with another amino acid, with the amino acid replacement constituting, in particular, a nonconservative amino acid substitution. This substitution impairs the efficiency or activity of the protein and reduces it down to a value of from 0 to 75%, from 0 to 50%, from 0 to 25%, from 0 to 10%, or from 0 to 5%. A nonsense mutation leads to a stop codon being located in the coding region of the gene and consequently to translation being terminated prematurely. Insertions or deletions of at least one base pair in a gene lead to frame shift mutations which result in incorrect amino acids being incorporated or in the translation being terminated prematurely. If a stop codon is formed in the coding region as a consequence of mutation, this then also leads to translation being terminated prematurely. Said measures are preferably carried out in the 5'-terminal part of the coding region, which encodes the N terminus of the polypeptide. If the overall length of a polypeptide (measured as the number of chemically linked L-amino acids) is set to 100%, then that part of the amino acid sequence, which, counted from the start amino acid L-formyl methionine, comprises 80% of the subsequent L-amino acids, belongs to the N terminus of the polypeptide.

Further directions for generating such mutations belong to the prior art and are contained in known textbooks of genetics and molecular biology such as the textbook by Knippers ("Molekulare Genetik [Molecular Genetics]", 6$^{th}$ edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986). Further measures are described in the prior art.

One method of reducing gene expression involves putting the gene to be attenuated under the control of a promotor inducible by addition of metered amounts of IPTG (isopropyl-β-D-thiogalactopyranoside), such as, for example, the trc promotor or the tac promotor. Examples of suitable vectors here are the *Escherichia coli* expression vector pXK99E (WO0226787; deposited in accordance with the Budapest Treaty in DH5alpha/pXK99E as DSM14440 with the Deutschen Sammlung für Mikroorganismen und Zellkulturen [German collection of microorganisms and cell cultures] (DSMZ, Braunschweig, Germany) on 31 Jul. 2001) and pVWEx2 (Wendisch, pH. D. thesis, Berichte des Forschungszentrums Jülich, Jül-3397, ISSN 0994-2952, Jëlich, Germany (1997)), which vectors enable the cloned gene to be expressed in *Corynebacterium glutamicum* in an IPTG-dependent manner.

This method was employed, for example, in the patent WO0226787 for regulated expression of the deaD gene by integrating the pXK99EdeaD vector into the *Corynebacterium glutamicum* genome, and by Simic et al. (Applied and Environmental Microbiology 68: 3321-3327 (2002)) for regulated expression of the glyA gene by integrating the pK18mobglyA' vector in *Corynebacterium glutamicum*.

Another method of specifically reducing gene expression is the antisense technique which involves delivering oligodeoxynucleotides or vectors to the target cells in order to synthesize relatively long antisense RNA. Said antisense RNA may bind there to complementary sections of specific mRNAs and reduce their stability or block translatability. An example of this can be found by the skilled worker in Srivastava et al. (Applied Environmental Microbiology 2000 October; 66 (10): 4366-4371).

The isolated coryneform bacteria which are obtained by the measures of the invention exhibit a secretion or production of the desired amino acid, in a fermentation process, which is increased as compared with that of the starting strain or parent strain which was initially employed.

"Isolated bacteria" are to be understood as being the mutants and recombinant bacteria, in particular coryneform bacteria, according to the invention which are isolated or generated and which comprise a rel allele which encodes a GTP-pyrophosphate kinase which comprises the described amino acid substitution in position 38 of the amino acid sequence.

The performance of the isolated bacteria, or of the fermentation process when using these bacteria, in regard to one or more of the parameters selected from the group comprising the product concentration (product per volume), the product yield (product formed per carbon source consumed) and the product formation (product formed per volume and time), or else of other process parameters and combinations, is improved by at least 0.5%, at least 1%, at least 1.5%, or at least 2%, based on the starting strain or parent strain or the fermentation process when using these strains.

The isolated coryneform bacteria according to the invention can be cultured continuously, as described, for example, in PCT/EP2004/008882, or discontinuously, in a batch process or a fed-batch process or a repeated fed-batch process, for the purpose of producing L-amino acids. A general summary of known culturing methods can be found in the textbook by Chmiel (Bioprozesstechnik 1. Einführung in die Bioverfahrenstechnik [Bioprocess Technology 1. Introduction to Bioprocess Technology] (Gustav Fischer Verlag, Stuttgart, 1991)) or in the textbook by Storhas (Bioreaktoren and periphere Einrichtungen [Bioreactors and Peripheral Equipment] (Vieweg Verlag, Brunswick/Wiesbaden, 1994)).

The culture medium or fermentation medium to be used must suitably satisfy the requirements of the given strains. Descriptions of media for culturing different microorganisms are given in the manual "Manual of Methods for General Bacteriology" published by the American Society for Bacteriology (Washington D.C., USA, 1981). The terms culture medium, fermentation medium and feed medium or medium are mutually interchangeable.

The carbon source employed can be sugars and carbohydrates, such as glucose, sucrose, lactose, fructose, maltose, molasses, sucrose-containing solutions derived from sugar beet or sugar cane production, starch, starch hydrolysate and cellulose, oils and fats, such as soybean oil, sunflower oil, peanut oil and coconut oil, fatty acids, such as palmitic acid, stearic acid and linoleic acid, alcohols, such as glycerol, methanol and ethanol, and organic acids, such as acetic acid. These substances can be used individually or as mixtures.

The nitrogen source employed can be organic nitrogen-containing compounds, such as peptones, yeast extract, meat extract, malt extract, cornsteep liquor, soybean flour and urea, or inorganic compounds, such as ammonium sulfate, ammonium chloride, ammonium phosphate, ammonium carbonate and ammonium nitrate. The nitrogen sources can be used individually or as mixtures.

The phosphorus source employed can be phosphoric acid, potassium dihydrogen phosphate or dipotassium hydrogen phosphate or the corresponding sodium-containing salts.

The culture medium must furthermore contain salts, for example in the form of chlorides or sulfates of metals such as sodium, potassium, magnesium, calcium and iron, for example magnesium sulfate or iron sulfate, which are necessary for growth. Finally, growth substances, such as amino acids, for example homoserine, and vitamins, for example thiamine, biotin or pantothenic acid, can be used in addition to the abovementioned substances. In addition to this, suitable precursors of the respective amino acid can be added to the culture medium.

The abovementioned added substances can be added to the culture in the form of a once-only mixture or fed in a suitable manner during the culture.

Basic compounds such as sodium hydroxide, potassium hydroxide, ammonia or ammonia water, or acidic compounds such as phosphoric acid or sulfuric acid, are employed in a suitable manner for controlling the pH of the culture. In general, the pH is adjusted to a value of from 6.0 to 9.0, preferably of from 6.5 to 8. It is possible to use antifoamants, such as fatty acid polyglycol esters, for controlling foam formation. Suitable substances which act selectively, such as antibiotics, can be added to the medium in order to maintain the stability of plasmids. In order to maintain aerobic conditions, oxygen or oxygen-containing gas mixtures, such as air, are passed into the culture. It is also possible to use liquids which are enriched with hydrogen peroxide. Where appropriate, the fermentation is conducted under positive pressure, for example under a pressure of 0.03 to 0.2 MPa. The temperature of the culture is normally from 20° C. to 45° C., and preferably from 25° C. to 40° C. In the case of batch processes, the culture is continued until a maximum of the desired amino acid has been formed. This objective may be achieved within from 10 hours to 160 hours. Longer culturing times are possible in the case of continuous processes.

Suitable fermentation media are described, inter alia, in U.S. Pat. No. 6,221,636, U.S. Pat. No. 5,840,551, U.S. Pat. No. 5,770,409, U.S. Pat. No. 5,605,818, U.S. Pat. No. 5,275,940, U.S. Pat. No. 4,275,157 and U.S. Pat. No. 4,224,409.

Methods for determining L-amino acids are disclosed in the prior art. The analysis can, for example, take place by means of anion exchange chromatography, followed by ninhydrin derivatization, as described in Spackman et al. (Analytical Chemistry, 30 (1958), 1190), or it can take place by reversed phase HPLC, as described in Lindroth et al. (Analytical Chemistry (1979) 51: 1167-1174).

The invention accordingly relates to a process for preparing an L-amino acid, which comprises a) fermenting an isolated coryneform bacterium in a suitable medium, said bacterium comprising a gene encoding a polypeptide having GTP-pyrophosphate kinase enzyme activity, with the L-proline in position 38 or the corresponding position in the amino acid sequences of said polypeptide having been replaced by a different proteinogenic amino acid, preferably L-leucine, and b) the L-amino acid being accumulated in the fermentation broth or in the cells of the isolated coryneform bacterium.

For this purpose, the L-amino acid accumulated in the nutrient medium or in the fermentation broth and/or in the bacterial cells are usually collected in order to obtain a solid or liquid product.

A fermentation broth is understood as being a fermentation medium in which a microorganism is cultured for a certain time and at a certain temperature. The fermentation medium, and/or the medium employed during the fermentation, contains/contain all the substances or components which ensure propagation of the microorganism and the formation of the desired amino acid.

At the conclusion of the fermentation, the resulting fermentation broth accordingly contains a) the biomass (cell mass) of the microorganism which has been formed as a consequence of the propagation of the cells of the microorganism, b) the desired amino acid which has been formed during the fermentation, c) the organic by-products which have been formed during the fermentation, and d) the constituents of the fermentation medium/fermentation media employed, or the added substances, for example vitamins, such as biotin, amino acids, such as homoserine, or salts, such as magnesium sulfate, which were not consumed by the fermentation.

The organic by-products include substances which are produced by the microorganisms employed in the fermentation, where appropriate in addition to the given desired L-amino acid, and are secreted, where appropriate. These by-products include L-amino acids which amount to less than 30%, 20% or 10% compared with the desired amino acid. They also include organic acids which carry from one to three carboxyl groups, such as acetic acid, lactic acid, citric acid, malic acid or fumaric acid. They also include sugars, such as trehalose.

Fermentation broths which are suitable for industrial purposes may have an amino acid content of from 30 g/kg to 200 g kg or of from 40 g/kg to 175 g/kg or of from 50 g/kg to 150 g/kg. The content of biomass (as dry biomass) may be from 20 to 50 g/kg.

In the case of the amino acid L-lysine, four different product forms have been disclosed in the prior art.

One group of L-lysine-containing products comprises concentrated, aqueous, alkaline solutions of purified L-lysine (EP-B-0534865). Another group, as described, for example, in U.S. Pat. No. 6,340,486 and U.S. Pat. No. 6,465,025, comprises aqueous, acidic, biomass-containing concentrates of L-lysine-containing fermentation broths. The best-known group of solid products comprises pulverulent or crystalline forms of purified or pure L-lysine, which is present in the form of a salt such as L-lysine monohydrochloride. Another group of solid product forms is described, for example, in EP-B-0533039. The product form which is described in this document contains, in addition to L-lysine, the major portion of the added substances which were used during the fermentative preparation, and which were not consumed, and, where appropriate, from >0% to 100% of the biomass of the microorganism employed.

In the case of the amino acids L-valine, L-isoleucine, L-proline, L-tryptophan and L-homoserine, product form containing the amino acids in question in purified or pure form (=95% by weight of =98% by weight) are known in the art.

In correspondence with the different product forms, a very wide variety of methods are known for collecting, isolating or purifying the L-amino acid from the fermentation broth for the purpose of preparing the L-amino acid-containing product or the purified L-amino acid.

Ion exchange chromatography methods, using active charcoal, and crystallization methods are used for preparing solid, pure L-amino acids. In the case of lysine, using these methods results in the corresponding base or a corresponding salt such as the monohydrochloride (Lys-HCl) or the lysine sulfate ($Lys_2$-$H_2SO_4$).

As far as lysine is concerned, EP-B-0534865 describes a method for preparing aqueous, basic L-lysine-containing solutions from fermentation broths. In this document, the biomass is separated off from the fermentation broth and discarded. A base such as sodium hydroxide, potassium hydroxide or ammonium hydroxide is used to adjust the pH to between 9 and 11. Following concentration and cooling, the mineral constituents (inorganic salts) are separated off from the broth by crystallization and either used as fertilizer or discarded.

In the case of processes for preparing lysine using the bacteria according to the invention, use is also made of those processes which result in products which contain constituents of the fermentation broth. These products are, in particular, used as animal feed additives.

Depending on the requirement, the biomass can be entirely or partially removed from the fermentation broth by means of separation methods such as centrifugation, filtration or decanting, or a combination of these methods, or all the biomass can be left in the fermentation broth. Where appropriate, the biomass, or the biomass-containing fermentation broth, is inactivated during a suitable process step, for example by means of thermal treatment (heating) or by means of adding acid.

The chemical components of the biomass are inter alia the cell envelope, for example peptidoglycan and arabinogalactane, the protein or polypeptides, for example the GTP-pyrophosphate kinase polypeptide, lipids and phospholipids and nucleic acids (DNA and RNA), for example polynucleotides comprising the mutation of the invention. As a consequence of the inactivation measures and/or the other steps (for example acidification, spray drying, granulation etc.), nucleic acids typically are fragments having a length of, inter alia, =40-60 bp, >60-80 bp, >80-100 bp, >100-200 bp, >200-300 bp, >300-400 bp, >400-500 bp, >500-750 bp, >750-1000 bp, >1000-1250 bp, >1250-1500 bp, >1500-1750 bp, >1750-2000 bp, >2000-2500 bp, >2500-3000 bp, >3000-4000 bp, >4000-5000 bp.

In one embodiment, the biomass is completely or virtually completely removed, such that no (0%) or at most 30%, at most 20%, at most 10%, at most 5%, at most 1% or at most 0.1%, of the biomass remains in the prepared product. In another embodiment, the biomass is not removed, or only removed in trivial amounts, such that all (100%) or more than 70%, 80%, 90%, 95%, 99% or 99.9% of the biomass remains in the prepared product. In one process according to the invention, the biomass is accordingly removed in proportions of from =0% to =100%.

The fermentation broth which is obtained after the fermentation can be adjusted, before or after the biomass has been completely or partially removed, to an acid pH using an inorganic acid, such as hydrochloric acid, sulfuric acid or phosphoric acid, or an organic acid, such as propionic acid (GB 1,439,728 or EP 1 331 220). It is likewise possible to acidify the fermentation broth when it contains the entire biomass (U.S. Pat. No. 6,340,486 or U.S. Pat. No. 6,465,025). The broth can also be stabilized by adding sodium bisulfite ($NaHSO_3$, GB 1,439,728) or another salt, for example an ammonium, alkali metal or alkaline earth metal salt of sulfurous acid.

Organic or inorganic solids which may be present in the fermentation broth are partially or entirely removed when the biomass is separated off. At least some (>0%), preferably at least 25%, preferably at least 50%, and more preferably at least 75%, of the organic by-products which are dissolved in the fermentation broth and the constituents of the fermentation medium (added substances), which are dissolved and not consumed remain in the product. Where appropriate, these by-products and constituents also remain completely (100%) or virtually completely, that is >95% or >98%, in the product. In this sense, the term "fermentation broth basis" means that a product comprises at least a part of the constituents of the fermentation broth.

Subsequently, water is extracted from the broth, or the broth is thickened or concentrated, using known methods, for example using a rotary evaporator, a thin-film evaporator or a falling-film evaporator, or by means of reverse osmosis or nanofiltration. This concentrated fermentation broth can then be worked up into flowable products, in particular into a finely divided powder or, preferably, a coarse-grained granulate, using methods of freeze drying, of spray drying or of spray granulation, or using other methods, for example in a circulating fluidized bed as described in PCT/EP2004/006655. Where appropriate, a desired product is isolated from the resulting granulate by means of screening or dust separation.

It is possible to dry the fermentation broth directly, i.e. by spray drying or spray granulation without any prior concentration.

"Flowable" is understood as meaning powders which discharge unhindered from a series of glass discharge vessels having discharge apertures of different sizes, i.e. which discharge unhindered at least from the vessel having a 5 mm (millimeter) aperture (Klein: Seifen, Öle, Fette, Wachse [Soaps, Oils, Fats and Waxes] 94, 12 (1968)).

"Finely divided" means a powder the majority (>50%) of which has a particle size which is from 20 to 200 μm in diameter.

"Coarse-grained" means a product the majority (>50%) of which has a particle size of from 200 to 2000 μm in diameter.

The particle size can be determined using methods of laser diffraction spectrometry. The corresponding methods are described in the textbook "Teilchengrößenmessung in der Laborpraxis [Particle Size Measurement in Laboratory Practice]" by R. H. Müller and R. Schuhmann, Wissenschaftliche Verlagsgesellschaft Stuttgart (1996) or in the textbook "Introduction to Particle Technology" by M. Rhodes, Wiley & Sons (1998).

The flowable, finely divided powder can in turn be converted, by means of suitable compacting or granulating methods, into a coarse-grained, readily flowable, storable, and to a large extent dust-free, product.

The term "dust-free" means that the product only contains small proportions (<5%) of particle sizes of less than 100 μm in diameter.

Within the meaning of this invention, "storable" means a product which can be stored for at least one (1) year or longer, preferably at least 1.5 years or longer, particularly preferably two (2) years or longer, in a dry and cool environment without there being any significant loss (<5%) of the given amino acid.

The invention also relates to a process for preparing an L-amino acid-, preferably L-lysine- or L-tryptophan-, containing product, preferably an animal feed additive, from fermentation broths, which process is characterized by the steps of
a) culturing and fermenting an L-amino acid-secreting coryneform bacterium, which comprises at least one rel allele encoding a polypeptide having GTP-pyrophosphate kinase activity, which polypeptide comprises an amino acid sequence in which one of the proteinogenic amino acids other than L-proline, preferably L-leucine, is present in position 38 or the comparable position, in a fermentation medium,
b) removing from 0 to 100% by weight of the biomass which is formed during the fermentation, and
c) drying the fermentation broth which is obtained in accordance with a) and/or b) in order to obtain the product in the desired powder form or granulate form,
with, where appropriate, an acid selected from the group sulfuric acid, phosphoric acid or hydrochloric acid being added prior to step b) or c). Preferably, water is being removed (concentration) from the L-amino acid-containing fermentation broth after step a) or b).

The invention further relates to a process for preparing a lysine sulfate-containing product, which process is outlined in DE 102006016158 and which involves processing the fermentation broth obtained using the microorganisms of the invention, from which broth the biomass has optionally been removed, either completely or partially, by carrying out a process comprising at least the following steps:
a) lowering the pH by adding sulfuric acid to from 4.0 to 5.2, in particular 4.9 to 5.1, and establishing in the broth a molar sulfate/L-lysine ratio from 0.85 to 1.2, preferably 0.9 to 1.0, more preferably >0.9 to <0.95, where appropriate by adding another or a plurality of sulfate-containing compounds, and
b) concentrating and, where appropriate, granulating the mixture obtained in this way by removing water,
where appropriate carrying out, prior to step a), either or both of the following measures:
c) measuring the molar ratio of sulfate/L-lysine in order to determine the required amount of sulfate-containing compounds
d) adding a sulfate-containing compound selected from the group consisting of ammonium sulfate, ammonium hydrogen sulfate and sulfuric acid in appropriate ratios.

Where appropriate, a salt of sulfurous acid, preferably alkali metal hydrogen sulfite, more preferably sodium hydrogen sulfite, is added in a concentration of from 0.01 to 0.5% by weight, preferably 0.1 to 0.3% by weight, more preferably 0.1 to 0.2% by weight, based on the fermentation broth, prior to step b).

Preferred sulfate-containing compounds are ammonium sulfate and/or ammonium hydrogen sulfate or corresponding mixtures of ammoniac and sulfuric acid and sulfuric acid itself.

The molar sulfate/L-lysine ratio V is calculated according to the formula: $V=2\times[SO_4^{2-}]/[L\text{-lysine}]$. This formula takes into account the fact that the $SO_4^{2-}$ anion is divalent. A ratio of $V=1$ means that $Lys_2(SO_4)$ has a stoichiometric composition, while a 10% sulfate shortfall is found at a ratio of $V=0.9$ and a 10% sulfate excess is found at a ratio of $V=1.1$.

Customary organic or inorganic auxiliary substances, or carrier substances such as starch, gelatin, cellulose derivatives or similar substances, may be used as binders, gelatinizers or thickeners in foodstuff or feedstuff processing, or other substances, such as silicic acids, silicates (EP0743016A) or stearates, in connection with the granulation or compacting.

The surface of the resulting granulates are provided with oils, as described in WO 04/054381. The oils which can be used are mineral oils, vegetable oils or mixtures of vegetable oils. Examples of these oils are soybean oil, olive oil and soybean oil/lecithin mixtures. In the same way, silicone oils, polyethylene glycols or hydroxyethyl cellulose also can be used. Treating the surfaces with said oils increases the abrasion resistance of the product and reduces the dust content. The content of oil in the product is from 0.02 to 2.0% by weight, preferably from 0.02 to 1.0% by weight, and more preferably from 0.2 to 1.0% by weight, based on the total quantity of the feedstuff additives.

Products having a content of =97% by weight of a particle size of from 100 to 1800 μm, or a content of =95% by weight of a particle size of from 300 to 1800 μm, in diameter are preferred. The content of dust, i.e. particles having a particle size of <100 μm, is preferably from >0 to 1% by weight, more preferably at most 0.5% by weight.

Alternatively, the product can also be absorbed onto an organic or inorganic carrier substance which is known in feedstuff processing, for example silicic acids, silicates, grists, brans, meals, starches, sugars etc., and/or be mixed and stabilized with thickeners or binders. Application examples and methods in this regard are described in the literature (Die Mühle+Mischfuttertechnik [The Grinding Mill+Mixed Feed Technology] 132 (1995) 49, page 817).

The product can also be brought, by means of coating methods using film formers such as metal carbonates, silicic acids, silicates, alginates, stearates, starches, rubbers and cellulose ethers, as described in DE-C-4100920, into a state in which it is stable towards digestion by animal stomachs, in particular the ruminant stomach.

In order to set a desired amino acid concentration in the product, the appropriate amino acid can, depending on the requirement, be added during the process in the form of a concentrate or, where appropriate, of a largely pure substance or its salt in liquid or solid form. The latter can be added individually, or as mixtures, to the resulting fermentation broth, or to the concentrated fermentation broth, or else be added during the drying process or granulation process.

The invention further relates to a process for preparing a solid lysine-containing product (see US 20050220933), which process comprises processing the fermentation broth obtained using the microorganisms of the invention in the following steps:
a) filtering the fermentation broth, preferably with a membrane filter so as to obtain a biomass-containing sludge and a filtrate,
b) concentrating the filtrate, preferably so as to obtain a solids content of from 48 to 52% by weight,
c) granulating the concentrate obtained in step b), preferably at a temperature of from 50° C. to 62° C., and
d) coating the granules obtained in c) with one or more of the coating agents).

Preferably, coating agents in step d) are selected from the group consisting of
d1) the biomass obtained in step a),
d2) an L-lysine-containing compound, preferably selected from the group consisting of L-lysine hydrochloride or L-lysine sulfate,
d3) an essentially L-lysine-free substance with an L-lysine content of <1% by weight, preferably <0.5% by weight, preferably selected from the group consisting of starch, carrageenan, agar, silicic acids, silicates, grains, bran and meals, and
d4) a water-repellent substance, preferably selected from the group consisting of oils, polyethylene glycols and liquid paraffins.

In the case of lysine, the ratio of the ions is preferably adjusted during the preparation of lysine-containing products such that the equivalent ion ratio in accordance with the following formula

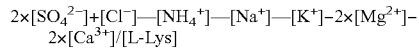

has a value of from 0.68 to 0.95, preferably of from 0.68 to 0.90, as described by Kushiki et al. in US 20030152633 (The molar concentrations are to be given in the "[ ]").

In the case of lysine, the solid fermentation broth-based product which has been prepared in this way has a lysine content (as lysine base) of from 10% by weight to 70% by weight or of from 20% by weight to 70% by weight, preferably of from 30% by weight to 70% by weight and more preferably of from 40% by weight to 70% by weight, based on the dry mass of the product. It is also possible to achieve maximum contents of lysine base of 71% by weight, 72% by weight or 73% by weight.

In the case of an electrically neutral amino acid such as L-tryptophan, the solid fermentation broth-based product which has been prepared in this way has an amino acid content of at least 5% by weight, 10% by weight, 20% by weight or 30% by weight and maximally 50% by weight, 60% by weight, 70% by weight, 80% by weight, 90% by weight or up to 95% by weight.

The water content of the solid product is up to 5% by weight, preferably up to 4% by weight, and more preferably less than 3% by weight.

The invention therefore also relates to an L-lysine-containing feed additive based on a fermentation broth, which has the following features
a) a lysine content (as base) of at least 10% by weight to no more than 73% by weight,
b) a water content of no more than 5% by weight, and
c) a biomass content corresponding to at least 0.1% of the biomass present in the fermentation broth, wherein the optionally inactivated biomass is formed by coryneform bacteria of the invention.

The invention therefore also relates to an L-tryptophan-containing feed additive based on a fermentation broth, which has the following features
a) a tryptophan content of at least 5% by weight to no more than 95% by weight,
b) a water content of no more than 5% by weight, and
c) a biomass content corresponding to at least 0.1% of the biomass present in the fermentation broth, wherein the optionally inactivated biomass is formed by coryneform bacteria of the invention.

The strain MH20-22B was deposited on Oct. 28, 2004 with the Deutsche Sammlung für Mikroorganismen und Zellkulturen [German Collection of Microorganisms and Cell Cultures] (DSMZ, Brunswick, Germany) as DSM 16833.

The *Corynebacterium glutamicum* mutant DM1915 of the invention, which comprises L-leucine in position 38 in the amino acid sequence of the Rel polypeptide, was deposited on May 15, 2006 at the Deutsche Sammlung für Mikroorganismen und Zellkulturen [German Collection of Microorganisms and Cell Cultures] (DSMZ, Brunswick, Germany) as DSM 18257.

The present invention is illustrated in more detail below on the basis of exemplary embodiments.

Example 1

Mutagenesis of the L-Lysine-Producing Strain DM1797

The *Corynebacterium glutamicum* strain DM1787 was used as parent strain for mutagenesis with N-methyl-N'-nitro-N-nitrosoguanidine (MNNG). Strain DM1797 is an aminoethyl cysteine-resistant mutant of *Corynebacterium glutamicum* ATCC13032 and has been deposited under DSM16833 with the Deutschen Sammlung für Mikroorganismen und Zellkulturen (DSMZ, Braunschweig, Germany).

The strain DM1797 was grown in 10 ml of LB broth (Merck, Darmstadt, Germany) in a 100 ml conical flask on a rotary shaker, type Certomat BS-1 (B. Braun Biotech International, Melsungen, Germany), at 33° C. and 200 rpm for 24 hours. The culture was then removed by centrifugation, the pellet was resuspended in 10 ml of 0.9% NaCl solution, the suspension obtained was again removed by centrifugation and the pellet obtained was taken up in 10 ml of 0.9% NaCl solution. 5 ml of this cell suspension were treated with 400 µg/ml MNNG at 30° C. and 200 rpm on shaker (see above) for 15 minutes. The mutagenesis mixture was then centrifuged and the pellet was taken up in 10 ml of 2% sodium thiosulfate in 0.9% NaCl buffer (pH=6.0). The cell suspension was then diluted with 0.9% NaCl solution in a ratio of 1:1000, 1:10 000 and 1:100 000, and aliquots were plated on brain heart agar (Merck, Darmstadt, Germany). Approximately 4500 mutants were isolated in this way.

Example 2

Performance Assay of the DM1797 Strain Mutants

The mutants obtained in example 1 were grown in a nutrient medium suitable for producing lysine, and the lysine content in the culture supernatant was determined.

For this purpose, the clones were firstly propagated on brain heart agar plates (Merck, Darmstadt, Germany) at 33° C. for 24 hours. Starting from these agar plate cultures, in each case a preculture was inoculated (10 ml of medium in a 100 ml conical flask). The medium used for the preculture was MM. The preculture was incubated on a shaker at 33° C. and 240 rpm for 24 hours. This preculture was used to inoculate a main culture, so that the starting OD (660 nm) of the main culture was 0.1. The medium MM was also used for the main culture.

| Medium MM | |
|---|---|
| CSL | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| $CaCO_3$ | 25 g/l |

CSL (Corn Steep Liquor), MOPS (morpholinopropanesulfonic acid) and the salt solution were adjusted to pH 7 with aqueous ammonia and autoclaved. The sterile substrate and vitamin solutions and the $CaCO_3$ autoclaved in the dry state are added.

Culturing was carried out in volumes of 10 ml each in 100 ml conical flasks with baffles. The temperature was 33° C., the number of revolutions was 250 rpm and the atmospheric humidity was 80%.

After 24 hours, the optical density (OD) was determined at a measurement wavelength of 660 nm with a Biomek 1000 (Beckmann Instruments GmbH, Munich, Germany). The amount of lysine produced was determined using an amino acid analyzer from Eppendorf-BioTronik (Hamburg, Germany) by ion exchange chromatography and post-column derivatization with ninhydrin detection. One mutant distinguished by increased lysine production was referred to as DM1915.

TABLE 1

| Strain | OD(660) | Lysine-HCl (g/l) |
|---|---|---|
| DM1797 | 9.3 | 2.2 |
| DM1915 | 9.2 | 2.4 |

Example 3

Sequencing of the Rel Allele of the DM1915 Mutant

Chromosomal DNA was isolated from the DM1915 clone by the method of Eikmanns et al. (Microbiology 140: 1817-1828 (1994)). A DNA section carrying the rel gene or allele was amplified with the aid of the polymerase chain reaction. Owing to the known sequence of the C. glutamicum rel gene (sequence No. 1824 from EP 1108790), the following primer oligonucleotides were selected for the PCR:

```
rel_XL_A1 (SEQ ID NO: 19):
5' gcgaattcta tcggatggaa catgaccg 3' rel_XL_A2 (SEQ ID NO: 20):
5' gcgaattcat gcggatgcca acaagatc 3'
```

The primers shown were synthesized by MWG Biotech (Ebersberg, Germany) and the PCR reaction was carried out following the standard PCR method by Innis et al. (PCR Protocols. A Guide to Methods and Applications, 1990, Academic Press). The primers enabled an approx. 1.53 kb DNA section carrying the rel gene or allele to be amplified. Moreover, the primers comprised the sequence for a restriction site of the EcoRI restriction endonuclease, which site is underlined in the nucleotide sequence depicted above.

The approx. 1.53 kb amplified DNA fragment carrying the rel allele of the DM1915 strain was identified by electrophoresis in a 0.8% strength agarose gel, isolated from said gel and purified using the usual methods (QIAquick Gel Extraction Kit, Qiagen, Hilden).

The nucleotide sequence of the amplified DNA fragment or PCR product was determined by sequencing by the company Agowa (Berlin, Germany). The sequence of the PCR product is depicted in SEQ ID NO:15. The sequence of the coding region is also depicted in SEQ ID NO:5. The amino acid sequence of the corresponding GTP-pyrophosphate kinase protein, which was produced with the aid of the Patentin program is depicted in SEQ ID NO:6.

Position 113 of the nucleotide sequence of the coding region of the rel allele of strain DM1915 has the base thymine (SEQ ID NO:5). The corresponding position of the wild-type gene has the base cytosine (SEQ ID NO:1).

Position 38 of the amino acid sequence of the GTP-pyrophosphate kinase protein of strain DM1915 has the amino acid leucine (SEQ ID NO:6). The corresponding position of the wild-type protein has the amino acid proline (SEQ ID NO:2).

The rel allele which comprises the base thymine in position 113 of the coding region and correspondingly encodes a GTP-pyrophosphate kinase protein whose amino acid sequence comprises the amino acid leucine in position 38 is referred to below as rel_P38L allele. In the term "rel_P38L", P is L-proline, L is L-leucine, and 38 indicates the position of the amino acid substitution (see SEQ ID NO:2 and 6).

The *Corynebacterium glutamicum* mutant DM1915 which harbors L-leucine in position 38 of the amino acid sequence of the Rel polypeptide was deposited as DSM 18257 with the Deutschen Sammlung für Mikroorganismen and Zellkulturen (DSMZ, Braunschweig, Germany) on 15 May 2006.

Example 4

Substitution of the Rel_P38L Allele for the Rel Wild-Type Gene of Strain DM1797

4.1 Construction of the Replacement Vector pK18mobsacB_rel_P38L

The approx. 1.53 kb DNA fragment described in example 3 and prepared by means of PCR, which carries the rel_P38L allele was incorporated into the chromosome of the *C. glutamicum* strain DM1797 described in example 1 by means of substitution mutagenesis with the aid of the sacB system described in Schäfer et al. (Gene, 14, 69-73 (1994)). This system enables allele substitutions occurring by way of homologous recombination to be produced and selected.

For this purpose, the approx. 1.53 kb rel_P38L fragment was cleaved by the restriction endonuclease EcoRI, identified by electrophoresis in a 0.8% strength agarose gel and subsequently isolated from the gel and purified using the usual methods (QIAquick Gel Extraction Kit, Qiagen, Hilden).

The mobilizable pK18mobsacB cloning vector was digested with the EcoRI restriction enzyme and the ends were dephosphorylated with alkaline phosphatase (Alkaline Phosphatase, Boehringer Mannheim, Germany). The vector prepared in this way was mixed with the approx. 1.53 kb rel_P38L fragment and the mixture was treated with T4 DNA ligase (Amersham-Pharmacia, Freiburg, Germany).

Subsequently, the *E. coli* strain S17-1 (Simon et al., Bio/Technology 1: 784-791, 1993) was transformed with the ligation mixture (Hanahan, In. DNA Cloning. A Practical Approach. Vol. 1, ILR Press, Cold Spring Harbor, New York, 1989). The plasmid-carrying cells were selected by plating the transformation mixture on LB agar (Sambrook et al., Molecular Cloning: A laboratory Manual. 2nd Ed., Cold Spring Harbor, N.Y., 1989), supplemented with 25 mg/l kanamycin.

Plasmid DNA was isolated from a transformant with the aid of the QIAprep Spin Miniprep Kit from Quiagen and examined by restriction cleavage with the enzyme PstI and subsequent agarose gel electrophoresis. The plasmid is named pK18mobsacB_rel_P38L and is depicted in FIG. 1.

4.2 Allele Substitution

The vector pK18mobsacB_rel_P38L mentioned in example 4.1 was transferred by conjugation into the *C. glutamicum* strain DM1797 following a protocol by Schäfer et al. (Journal of Microbiology 172: 1663-1666 (1990)). Said vector cannot self-replicate in DM1797 and is maintained in the cell only when integrated in the chromosome as a consequence of a recombinant event. The selection of transconjugants, i.e. of clones containing integrated pK18mobsacB_rel_Pe8L, was carried out by plating the conjugation mixture on LB agar (Sambrook et al., Molecular Cloning: A Laboratory Manual, 2nd Ed. Cold Spring Harbor, N.Y., 1989) supplemented with 15 mg/l, kanamycin and 50 mg/l nalidixic acid. Kanamycin-resistant transconjugants were streaked on LB agar plates containing 25 mg/l kanamycin and incubated at 33° C. for 24 hours. Mutants in which the plasmid had been excised as the result of a second recombinant event were selected by growing the clones without selection in LB liquid medium for 30 hours, then streaking them out on LB agar containing 10% sucrose and incubating for 16 hours.

Like the starting plasmid pK18mobsacB, the plasmid pK118mobsacB_rel_P38L comprises, in addition to the kanamycin resistance gene, a copy of the sacB gene encoding *Bacillus subtilis* levan sucrase. Sucrose-inducible expression results in the formation of levan sucrase which catalyzes the synthesis of the product levan which is toxic to *C. glutamicum*. Therefore only those clones in which the integrated pK18mobsacB_rel_P38L has been excised due to a second recombinant event grow on LB agar containing sucrose. Depending on the location of the second recombinant event with respect to the site of mutation, the excision results in allele substitution or incorporation of the mutation or the original copy remains in the chromosome of the host.

Approximately 40 to 50 colonies were tested for the phenotype "growth in the presence of sucrose" and "no growth in the presence of kanamycin". A region of the rel gene, which covers the P38L mutation, was sequenced in four colonies having the "growth in the presence of sucrose" and "no growth in the presence of kanamycin" phenotype, starting from the sequencing primer rel-2 (corresponding to the nucleotide sequence position 695-714 of the sequence upstream of the CDS of the rel gene from SEQ ID NO:3), by the company Agowa (Berlin, Germany), in order to verify the presence of the mutation of the rel_P38L allele in the chromosome. For this purpose, the primer used, rel-2, was synthesized by Agowa:

```
rel-2:
5' ccg tca ttg tgg tca gag at 3'.  (SEQ ID NO: 23)
```

In this way, a clone was identified which comprises the base thymine in position 113 of the coding region of the rel gene and therefore has the rel_P38L allele. This clone was referred to as DM1797rel_P38L strain.

Example 6

Comparison of the performance of the DM1797rel_P38L strain with that of the DM1797 parent strain The performance assay of the *C. glutamicum* DM1797rel_P38L strain obtained in example 5 was carried out as described in example 2. The result of the experiment is depicted in table 2.

TABLE 2

| Strain | OD (660 nm) | Lysine-HCl g/l |
|---|---|---|
| DM1797 | 9.3 | 2.2 |
| DM1797rel_P38L | 9.2 | 2.5 |

The abbreviations and designations used have the following meaning. The base pair numbers given are approximations obtained within the reproducibility of measurements.

| | |
|---|---|
| Kan: | kanamycin resistance gene |
| EcoRI: | EcoRI restriction enzyme cleavage site |
| PstI: | PstI restriction enzyme cleavage site |
| rel: | rel_P38L allele |
| sacB: | sacB gene |
| RP4-mob: | mob region with the origin of replication for transfer (oriT) |
| oriV: | origin of replication V |

German patent application 102006048882.2, filed Oct. 17, 2006, and U.S. provisional application 60/830,331, filed Jul. 13, 2006, are incorporated herein by reference.

Numerous modification and variations on the present invention are possible in light of the above teachings. It is therefore to be understood that within the scope of the appended claims, the invention may be practiced otherwise than as specifically described herein.

What is claimed is:

1. An isolated polynucleotide encoding an amino acid sequence comprising a polypeptide having GTP-pyrophosphate kinase enzyme activity, wherein the polypeptide is as set forth by SEQ ID NO: 2 in which L-proline in position 38 has been replaced by L-leucine.

2. The isolated polynucleotide as claimed in claim 1, wherein the encoded amino acid sequence is 760 amino acids in length.

3. The isolated polynucleotide as claimed in claim 1, which comprises nucleotides 751-3033 of SEQ ID NO: 7.

4. The isolated polynucleotide as claimed in claim 1, which hybridizes with the nucleotide sequence complementary to the full-length of SEQ ID NO: 5 under conditions of hybridization in 5×SSC at approximately 50° C.-68° C. followed by washing in 0.5×SSC at 66° C.-68° C.

5. A process for preparing a recombinant microorganism, comprising
   a) transferring the isolated polynucleotide as claimed in claim 1 to a microorganism,
   b) replicating said isolated polynucleotide in said microorganism, and
   c) propagating the microorganism obtained by a) and b).

6. A recombinant microorganism comprising the isolated polynucleotide as claimed in claim 1.

7. The recombinant microorganism as claimed in claim 6, which is a coryneform bacterium or a bacterium of the genus *Escherichia*.

8. The recombinant microorganism as claimed in claim 7, wherein the coryneform bacterium is the genus *Corynebacterium*.

9. The recombinant microorganism as claimed in claim 8, wherein the bacterium of the genus *Corynebacterium* is the species *Corynebacterium glutamicum*.

10. A vector comprising the isolated polynucleotide as claimed in claim 1.

11. A recombinant microorganism comprising the vector as claimed in claim 10.

12. The recombinant microorganism as claimed in claim 11, which is a coryneform bacterium or a bacterium of the genus *Escherichia*.

13. The recombinant microorganism as claimed in claim 12, wherein the coryneform bacterium is the genus *Corynebacterium*.

14. The recombinant microorganism as claimed in claim 13, wherein the bacterium of the genus *Corynebacterium* is the species *Corynebacterium glutamicum*.

15. A process for overexpressing a GTP-pyrophosphate kinase in a microorganism comprising increasing the copy number of the polynucleotide as claimed in claim 1 in a microorganism by at least one (1) copy.

16. A process for overexpressing a GTP-pyrophosphate kinase in a microorganism, comprising functionally linking a promotor or an expression cassette to the polynucleotide of claim 1 and expressing the encoded polypeptide in a microorganism.

* * * * *